United States Patent
Zaltsman et al.

(10) Patent No.: US 11,134,676 B2
(45) Date of Patent: *Oct. 5, 2021

(54) ANTI-MICROBIAL PARTICLES AND METHODS OF USE THEREOF

(71) Applicant: NOBIO LTD., Kadima (IL)

(72) Inventors: Nathan Zaltsman, Hadera (IL); Ervin I. Weiss, Herzliya (IL)

(73) Assignee: NOBIO LTD., Kadima (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/117,693

(22) Filed: Aug. 30, 2018

(65) Prior Publication Data

US 2019/0059366 A1    Feb. 28, 2019

Related U.S. Application Data

(60) Provisional application No. 62/551,813, filed on Aug. 30, 2017, provisional application No. 62/551,806, (Continued)

(51) Int. Cl.
*A01N 25/26* (2006.01)
*A01N 33/02* (2006.01)
(Continued)

(52) U.S. Cl.
CPC .......... *A01N 25/26* (2013.01); *A01N 25/02* (2013.01); *A01N 25/10* (2013.01); *A01N 33/02* (2013.01); *A01N 33/04* (2013.01); *A01N 33/12* (2013.01); *A61K 6/69* (2020.01); *A61K 6/80* (2020.01); *A61K 8/0241* (2013.01); *A61K 8/25* (2013.01); *A61K 8/416* (2013.01); *A61L 15/44* (2013.01); *A61L 24/0015* (2013.01); *A61L 24/0089* (2013.01); *A61L 26/0066* (2013.01); *A61L 27/446* (2013.01); *A61L 27/54* (2013.01);
(Continued)

(58) Field of Classification Search
None
See application file for complete search history.

(56) References Cited

U.S. PATENT DOCUMENTS

| 3,972,855 A | 8/1976 | Martinsson et al. |
| 4,144,122 A | 3/1979 | Emanuelsson et al. |

(Continued)

FOREIGN PATENT DOCUMENTS

| CA | 2799833 C | 4/2016 |
| CN | 102698313 A | * 10/2012 |

(Continued)

OTHER PUBLICATIONS

S Farah, O Aviv, N Laout, S Ratner, N Beyth, AJ Domb. "Antimicrobial silica particles loaded with quaternary ammonium polyethyleneimine network." Polymers for Advanced TEchnologies, vol. 25, 2014, pp. 689-692. (Year: 2014).*

(Continued)

*Primary Examiner* — Isaac Shomer
(74) *Attorney, Agent, or Firm* — Pearl Cohen Zedek Latzer Baratz LLP

(57) ABSTRACT

This invention relates to anti-microbial active particles, compositions and uses thereof for inhibiting bacterial growth on surfaces or devices. This invention further discloses methods of making such anti-microbial active particles.

29 Claims, 20 Drawing Sheets

Related U.S. Application Data filed on Aug. 30, 2017, provisional application No. 62/644,604, filed on Mar. 19, 2018.

(51) Int. Cl.

| | | |
|---|---|---|
| A01N 33/04 | (2006.01) | |
| C08K 9/04 | (2006.01) | |
| C08F 292/00 | (2006.01) | |
| C08F 251/00 | (2006.01) | |
| C08F 265/04 | (2006.01) | |
| C08F 271/00 | (2006.01) | |
| A01N 25/02 | (2006.01) | |
| A01N 25/10 | (2006.01) | |
| C08F 257/02 | (2006.01) | |
| A61K 8/02 | (2006.01) | |
| A61L 26/00 | (2006.01) | |
| A61L 31/16 | (2006.01) | |
| A61L 15/44 | (2006.01) | |
| A61K 6/69 | (2020.01) | |
| A61K 6/80 | (2020.01) | |
| A01N 33/12 | (2006.01) | |
| A61K 8/25 | (2006.01) | |
| A61K 8/41 | (2006.01) | |
| A61L 24/00 | (2006.01) | |
| A61L 27/44 | (2006.01) | |
| A61L 27/54 | (2006.01) | |
| A61Q 11/00 | (2006.01) | |
| C01B 33/12 | (2006.01) | |
| C08K 3/22 | (2006.01) | |
| C08K 3/36 | (2006.01) | |
| B65D 81/28 | (2006.01) | |

(52) U.S. Cl.
CPC ............. *A61L 31/16* (2013.01); *A61Q 11/00* (2013.01); *C01B 33/126* (2013.01); *C08F 251/00* (2013.01); *C08F 257/02* (2013.01); *C08F 265/04* (2013.01); *C08F 271/00* (2013.01); *C08F 292/00* (2013.01); *C08K 3/22* (2013.01); *C08K 3/36* (2013.01); *C08K 9/04* (2013.01); *A61K 2800/57* (2013.01); *A61L 2300/404* (2013.01); *A61L 2300/62* (2013.01); *B65D 81/28* (2013.01); *C08F 2500/24* (2013.01); *C08K 2003/2275* (2013.01)

(56) References Cited

U.S. PATENT DOCUMENTS

| | | |
|---|---|---|
| 5,277,136 A | 1/1994 | Davis |
| 5,408,022 A | 4/1995 | Imazato et al. |
| 5,494,987 A | 2/1996 | Imazato et al. |
| 5,672,368 A | 9/1997 | Perkins |
| 5,672,638 A | 9/1997 | Verhoeven et al. |
| 5,733,949 A | 3/1998 | Imazato et al. |
| 5,798,117 A | 8/1998 | New et al. |
| 5,954,869 A | 9/1999 | Elfersy et al. |
| 5,980,868 A | 11/1999 | Homola et al. |
| 6,039,940 A | 3/2000 | Perrault et al. |
| 6,113,815 A | 9/2000 | Elfersy et al. |
| 6,120,587 A | 9/2000 | Elfersy et al. |
| 6,123,925 A * | 9/2000 | Barry ............. A61K 8/11 424/49 |
| 6,146,688 A | 11/2000 | Morgan et al. |
| 6,183,248 B1 | 2/2001 | Chishti et al. |
| 6,251,967 B1 * | 6/2001 | Perichaud ......... A01N 25/10 523/122 |
| 6,355,704 B1 | 3/2002 | Nakatsuka et al. |
| 6,482,402 B1 | 11/2002 | Kurtz et al. |
| 6,559,116 B1 | 5/2003 | Godfroid et al. |
| 6,562,330 B1 | 5/2003 | Stratford et al. |
| 6,572,926 B1 | 6/2003 | Morgan et al. |
| 6,607,382 B1 | 8/2003 | Kuo et al. |
| 6,762,172 B1 | 7/2004 | Elfersy et al. |
| 6,929,818 B2 | 8/2005 | Luthra et al. |
| 7,115,421 B2 | 10/2006 | Grzeda et al. |
| 7,709,694 B2 | 5/2010 | Batich et al. |
| 7,771,743 B1 | 8/2010 | Luthra et al. |
| 7,799,888 B2 | 9/2010 | Arkles et al. |
| 7,851,653 B2 | 12/2010 | Getman et al. |
| 7,858,141 B2 | 12/2010 | Getman et al. |
| 8,389,021 B2 | 3/2013 | Baker |
| 8,439,674 B2 | 5/2013 | Li et al. |
| 8,455,599 B2 | 6/2013 | Arkles et al. |
| 8,535,645 B2 | 9/2013 | Domb et al. |
| 8,999,291 B2 | 4/2015 | Goodman et al. |
| 9,314,407 B2 | 4/2016 | Blizzard et al. |
| 9,624,384 B2 | 4/2017 | Mason et al. |
| 9,744,120 B2 | 8/2017 | Neigel |
| 10,010,080 B2 | 7/2018 | Neigel |
| 10,159,630 B2 | 12/2018 | Blizzard et al. |
| 10,328,020 B1 | 6/2019 | Neigel |
| 10,405,553 B1 | 9/2019 | Mason et al. |
| 10,531,664 B2 | 1/2020 | Mason et al. |
| 2004/0077892 A1 | 4/2004 | Arkles et al. |
| 2004/0180093 A1 | 9/2004 | Burton et al. |
| 2005/0277752 A1 | 12/2005 | Bringley |
| 2006/0018966 A1 | 1/2006 | Lin et al. |
| 2006/0115782 A1 | 6/2006 | Li et al. |
| 2006/0115785 A1 | 6/2006 | Li et al. |
| 2007/0258996 A1 | 11/2007 | Pradip et al. |
| 2007/0299538 A1 | 12/2007 | Roeber |
| 2008/0069887 A1 * | 3/2008 | Baran ............ B82Y 30/00 424/490 |
| 2008/0226728 A1 * | 9/2008 | Domb ............ A01N 37/12 424/489 |
| 2009/0285886 A1 | 11/2009 | Van Beek |
| 2010/0004202 A1 | 1/2010 | Chisholm et al. |
| 2014/0308330 A1 | 10/2014 | Santra et al. |
| 2014/0322287 A1 | 10/2014 | Onis et al. |
| 2016/0051450 A1 | 2/2016 | Kashiki et al. |
| 2016/0135470 A1 | 5/2016 | Agrawal et al. |
| 2016/0235631 A1 | 8/2016 | Nojiri |
| 2018/0362714 A1 | 12/2018 | Grubbs et al. |
| 2019/0053487 A1 | 2/2019 | Zaltsman et al. |

FOREIGN PATENT DOCUMENTS

| | | |
|---|---|---|
| CN | 103655452 A * | 3/2014 |
| CN | 102838085 B | 4/2014 |
| CN | 102549082 B | 1/2015 |
| CN | 106567259 A | 4/2017 |
| DE | 102012003117 A1 | 8/2013 |
| DE | 102009047589 | 1/2014 |
| EP | 0360962 A2 | 4/1990 |
| EP | 0537774 | 4/1993 |
| EP | 0688901 A2 | 12/1995 |
| EP | 0705590 A1 | 4/1996 |
| EP | 0607195 B1 | 4/1999 |
| EP | 0908189 A2 | 4/1999 |
| EP | 1042005 A2 | 10/2000 |
| EP | 0980682 B1 | 11/2003 |
| EP | 1863865 B1 | 5/2012 |
| EP | 2450058 A1 | 5/2012 |
| EP | 1841314 B1 | 3/2014 |
| EP | 3269771 A1 | 1/2018 |
| FR | 3071729 A1 | 4/2019 |
| JP | 53130428 | 11/1978 |
| JP | 02307913 | 12/1990 |
| JP | 05209020 | 8/1993 |
| JP | 05229975 | 9/1993 |
| JP | 06341013 | 12/1994 |
| JP | 07206621 | 8/1995 |
| JP | 07215814 | 8/1995 |
| JP | 08253637 | 10/1996 |
| JP | 1025218 | 1/1998 |
| JP | 10139797 | 5/1998 |
| JP | 10204727 | 8/1998 |
| JP | 10236914 | 9/1998 |
| JP | 10236915 | 9/1998 |

(56) References Cited

FOREIGN PATENT DOCUMENTS

| | | |
|---|---|---|
| JP | 2000063290 | 2/2000 |
| JP | 2002122827 | 4/2002 |
| JP | 2003104435 | 4/2003 |
| JP | 2003286151 | 10/2003 |
| JP | 2003301055 | 10/2003 |
| JP | 2005179238 | 7/2005 |
| JP | 2007269637 | 10/2007 |
| JP | 2008184431 | 8/2008 |
| JP | 2011038195 | 2/2011 |
| JP | 4783707 B2 | 9/2011 |
| JP | 2014001166 A | 1/2014 |
| JP | 2018002642 A | 1/2018 |
| KR | 20180006705 A | 1/2018 |
| WO | WO 1993/020775 A1 | 10/1993 |
| WO | WO 1995/010940 A1 | 4/1995 |
| WO | WO 2001/090251 | 11/2001 |
| WO | WO 2005/123612 A2 | 12/2005 |
| WO | WO 2008/049250 A1 | 5/2008 |
| WO | WO 2008/149505 | 12/2008 |
| WO | WO 2009/027971 A2 | 3/2009 |
| WO | WO 2009/091001 | 7/2009 |
| WO | WO 2010/091124 A2 | 8/2010 |
| WO | WO 2011/036031 A1 | 3/2011 |
| WO | WO 2011/097347 A2 | 8/2011 |
| WO | WO 2012/021754 A2 | 2/2012 |
| WO | WO 2014/058757 A2 | 8/2014 |
| WO | WO 2015/104894 | 7/2015 |
| WO | WO 2016/172436 A1 | 10/2016 |
| WO | WO 2017/078622 A1 | 5/2017 |
| WO | WO 2017/145142 A1 | 8/2017 |
| WO | WO 2017/145167 A1 | 8/2017 |
| WO | WO 2019/078198 A1 | 4/2019 |

OTHER PUBLICATIONS

J Song, H Kong, J Jang. "Bacterial adhesion inhibition of the quaternary ammonium functionalized silica nanoparticles." Colloids and Surfaces B: Biointerfaces, vol. 82, 2011, pp. 651-656. (Year: 2011).*

English Translation of CN 103655452 A. Obtained from https://patents.google.com/patent/CN103655452A/en?oq=aminobutyl+triethoxysilane+a61k on Feb. 19, 2020. Originally published in Chinese on Mar. 26, 2014. pp. 1-8. (Year: 2014).*

H-S Jung, D-S Moon, J-k Lee. "Quantitative Analysis and Efficient Surface Modification of Silica Nanoparticles." Journal of Nanomaterials, vol. 2012, Article ID 593471, pp. 1-8 and supplementary pp. 1-5, copyright 2012. (Year: 2012).*

M Zhu, Y Zhu, L Zhang, J Shi. "Preparation of chitosan/mesoporous silica nanoparticle composite hydrogels for sustained co-delivery of biomacromolecules and small chemical drugs." Science and Technology of Advanced Materials, vol. 14, 2013, pp. 1-9. (Year: 2013).*

J-H Lee, A El-Fiqi, J-K Jo, D-A Kim, S-C Kim, S-K Jun, H-W Kim, H-H Lee. "Development of long-term antimicrobial poly(methyl methacrylate) by incorporating mesoporous silica nanocarriers." Dental Materials, vol. 32, 2016, pp. 1564-1574. (Year: 2016).*

K Subramani, W Ahmed. "Emerging Nanotechnologies in Dentistry Materials, Processes and Applications." Elsvier, Copyright 2012, ISBN 978-1-4557-7862-1, p. 30, title page, and copyright page (3 sheets) included. (Year: 2012).*

Google Translate. English Translation of CN 102698313A. Obtained from https://patents.google.com/patent/CN102698313A/en?oq=alginate+hydrogel+antimicrobial on Jun. 11, 2020. 10 printed pages. Originally published in Chinese on Oct. 3, 2012. (Year: 2012).*

Shady Farah, Oren Aviv, Natalia Laout, Stanislav Ratner, Nurit Beythand Abraham J. Domb. "Antimicrobial silica particles loaded with quaternary ammonium polyethyleneimine network." Polymers for Advanced Technologies, vol. 25, 2014, pp. 689-692. (Year : 2014).*

Dmitri D. Iarikov, Mehdi Kargar, Ali Sahari, Lauren Russel, Katelyn T. Gause, Bahareh Behkam, and William A. Ducker. "Antimicrobial Surfaces Using Covalently Bound Polyallylamine." Biomacromolecules, vol. 15, 2014, pp. 169-176. (Year: 2014).*

Magdalena Wytrwal, Paulina Koczurkiewicz, Kinga Wojcik, Marta Michalik, Bartlomiej Kozik, Marek Zylewski, Maria Nowakowska, Mariusz Kepczynski. "Synthesis of strong polycations with improved biological properties." Journal of Biomedical Materials Research A, vol. 00A, Issue 00, 2013, pp. 1-11. (Year: 2013).*

P. Makvandi, M. Ghaemy, A.A. Ghadiri, and M. Mohseni. "Photocurable, Antimicrobial Quaternary Ammonium-modified Nanosilica." Journal of Dental Research, vol. 94(10), 2015, pp. 1401-1407. (Year: 2015).*

Abramovitz, I., et al. (2013). Antibacterial temporary restorative materials incorporating polyethyleneimine nanoparticles. Quintessence international, 44(3).

Beyth, N., et al. (2006). Antibacterial activity of dental composites containing quaternary ammonium polyethylenimine nanoparticles against Streptococcus mutans. Biomaterials, 27(21), 3995-4002.

Beyth, N., et al. (2010). Long-term antibacterial surface properties of composite resin incorporating polyethyleneimine nanoparticles. Quintessence international, 41(10).

Beyth, N., et al. (2010). Polyethyleneimine nanoparticles incorporated into resin composite cause cell death and trigger biofilm stress in vivo. Proceedings of the National Academy of Sciences, 107(51), 22038-22043.

Beyth, N., et al. (2012). Antibacterial activity of dental cements containing quaternary ammonium polyethylenimine nanoparticles. Journal of Nanomaterials, 2012, 58.

Beyth, N., et al. (2013). Rapid Kill—Novel Endodontic Sealer and Enterococcus faecalis. PloS one, 8(11), e78586.

Beyth, N., et al. (2014). Antibacterial dental resin composites. Reactive and Functional Polymers, 75, 81-88.

Beyth, N., et al. (2018). Antimicrobial nanoparticles in restorative composites. In Emerging Nanotechnologies in Dentistry (pp. 35-47). William Andrew Publishing.

Beyth, S.,et al. (2013). Antibacterial activity of bone cement containing quaternary ammonium polyethyleneimine nanoparticles. Journal of Antimicrobial Chemotherapy, 69(3), 854-855.

Busscher, H. J., et al. (2010). Biofilm formation on dental restorative and implant materials. Journal of dental research, 89(7), 657-665.

Carpenter, A. W., et al. (2012). Dual action antimicrobials: nitric oxide release from quaternary ammonium-functionalized silica nanoparticles. Biomacromolecules, 13(10), 3334-3342.

Domb, A. J., et al. (2013). Quaternary Ammonium Antimicrobial Polymers. MRS Online Proceedings Library Archive, 1569, 97-107.

Farah, S., et al. (2013). Crosslinked QA-PEI nanoparticles: synthesis reproducibility, chemical modifications, and stability study. Polymers for Advanced Technologies, 24(5), 446-452.

Farah, S., et al. (2014). Antimicrobial silica particles loaded with quaternary ammonium polyethyleneimine network. Polymers for Advanced Technologies, 25(6), 689-692.

Imazato et al., (2000). Cytotoxic effects of composite restorations employing self-etching primers or experimental antibacterial primers. Journal of dentistry, 28(1), 61-67. (Only abstract).

Imazato et al., (2002). Penetration of an antibacterial dentine-bonding system into demineralized human root dentine in vitro. European journal of oral sciences, 110(2), 168-174. (Only abstract).

Imazato et al., (2003). Antibacterial activity of bactericide-immobilized filler for resin-based restoratives. Biomaterials, 24(20), 3605-3609.

International Search Report issued for PCT Application No. PCT/IL2006/000005 dated Mar. 13, 2006.

International Search Report issued for PCT Application No. PCT/IL2016/050219 dated Jun. 16, 2016.

International Search Report issued for PCT Application No. PCT/IL2017/050240 dated Jun. 19, 2017.

International Search Report issued for PCT Application No. PCT/IL2018/050969 dated Nov. 12, 2018.

International Search Report issued for PCT Application No. PCT/IL2018/050970 dated Nov. 11, 2018.

(56) References Cited

OTHER PUBLICATIONS

Ionescu, A., et al. (2012). Influence of surface properties of resin-based composites on in vitro S treptococcus mutans biofilm development. European journal of oral sciences, 120(5), 458-465. (Only abstract).

Kawabata, N., et al. (1988). Antibacterial activity of soluble pyridinium-type polymers. Appl. Environ. Microbiol., 54(10), 2532-2535.

Kenawy, E. R., et al. (2006). Biologically active polymers: VII. Synthesis and antimicrobial activity of some crosslinked copolymers with quaternary ammonium and phosphonium groups. Reactive and Functional Polymers, 66(4), 419-429.

Kim, H. W., et al. (2010). Imparting durable antimicrobial properties to cotton fabrics using alginate-quaternary ammonium complex nanoparticles. Carbohydrate polymers, 79(4), 1057-1062.

Li, P., et al. (2005). Synergistic antibacterial effects of β-lactam antibiotic combined with silver nanoparticles. Nanotechnology, 16(9), 1912.

Li, P., et al. (2011). A polycationic antimicrobial and biocompatible hydrogel with microbe membrane suctioning ability. Nature materials, 10(2), 149.

Lin J., et al. (2002). Bactericidal properties of flat surfaces and nanoparticles derivatized with alkylated polyethylenimines. Biotechnology Progress, 18(5), 1082-1086. (Only the abstracts are provided).

Lin, J., et al. (2003). Mechanism of bactericidal and fungicidal activities of textiles covalently modified with alkylated polyethylenimine. Biotechnology and Bioengineering, 83(2), 168-172. (Only abstract).

Majumdar, P., et al. (2009). Synthesis and antimicrobial activity of quaternary ammonium-functionalized POSS (Q-POSS) and polysiloxane coatings containing Q-POSS. Polymer, 50(5), 1124-1133.

Matalon, S., et al. (2003). Surface antibacterial properties of fissure sealants. Pediatric dentistry, 25(1), 43-48.

Melo, L. D., et al. (2010). Antimicrobial particles from cationic lipid and polyelectrolytes. Langmuir, 26(14), 12300-12306.

Nohr, R. S. et al. (1994). New biomaterials through surface segregation phenomenon: new quaternary ammonium compounds as antibacterial agents. Journal of Biomaterials Science, Polymer Edition, 5(6), 607-619. (Only abstract).

Novotná, E., et al. (2014). Synthesis and Biological Activity of Quaternary Ammonium Salt-Type Agents Containing Cholesterol and Terpenes. Archiv der Pharmazie, 347(6), 381-386.

Ono, M., et al. (2007). Surface properties of resin composite materials relative to biofilm formation. Dental materials journal, 26(5), 613-622.

Reinhardt, N., et al. (2015). Quaternary ammonium groups exposed at the surface of silica nanoparticles suitable for DNA complexation in the presence of cationic lipids. The Journal of Physical Chemistry B, 119(21), 6401-6411.

Richter, A. P., et al. (2015). An environmentally benign antimicrobial nanoparticle based on a silver-infused lignin core. Nature nanotechnology, 10(9), 817.

Rumbaugh, K. P., & Ahmad, I. (2014). Antibiofilm Agents. Springer Series on Biofilms, 8.

Sbordone, L., et al. (2003). Oral microbial biofilms and plaque-related diseases: microbial communities and their role in the shift from oral health to disease. Clinical oral investigations, 7(4), 181-188. (Only abstract).

Shalhav, M., et al. (1997). In vitro antibacterial activity of a glass ionomer endodontic sealer. Journal of endodontics, 23(10), 616-619.

Shvero, D. K., et al. (2010). Antibacterial effect of polyethyleneimine nanoparticles incorporated in provisional cements against *Streptococcus mutans*. Journal of Biomedical Materials Research Part B: Applied Biomaterials, 94(2), 367-371.

Shvero, D. K., et al. (2013). Towards antibacterial endodontic sealers using quaternary ammonium nanoparticles. International endodontic journal, 46(8), 747-754.

Shvero, D. K., et al. (2015). Characterisation of the antibacterial effect of polyethyleneimine nanoparticles in relation to particle distribution in resin composite. Journal of dentistry, 43(2), 287-294.

Siedenbiedel, F., et al.(2012). Antimicrobial polymers in solution and on surfaces: overview and functional principles. Polymers, 4(1), 46-71.

Song, J., et al. (2011). Bacterial adhesion inhibition of the quaternary ammonium functionalized silica nanoparticles. Colloids and Surfaces B: Biointerfaces, 82(2), 651-656.

Supplementary Search Report issued for EP Application No. 17 75 5952 dated Sep. 25, 2019.

Weiss, E. I., et al. (1996). Assessment of antibacterial activity of endodontic sealers by a direct contact test. Dental Traumatology, 12(4), 179-184.

Yudovin-Farber, I.,et al. (2008). Surface characterization and biocompatibility of restorative resin containing nanoparticles. Biomacromolecules, 9(11), 3044-3050.

Yudovin-Farber, I., et al. (2010). Antibacterial effect of composite resins containing quaternary ammonium polyethyleneimine nanoparticles. Journal of Nanoparticle Research, 12(2), 591-603.

Yudovin-Farber, I., et al. (2010). Quaternary ammonium polyethyleneimine: antibacterial activity. Journal of nanomaterials, 2010, 46.

Zaltsman, N., et al. (2017). Surface-modified nanoparticles as anti-biofilm filler for dental polymers. PloS one, 12(12), e0189397.

Biosafe. Technical Guide for Performance and Regulatory Compliance—Organosilane Antimicrobials; Provides long-lasting surface protection. Downloaded on Feb. 2017.

Jung et al. "Quantitative Analysis and Efficient Surface Modification of Silica Nanoparticles." Journal of Nanomaterials, vol. 2012, Article ID 593471, pp. 1-8; and Supplementary Information, pp. 1-5. (Year: 2012).

Wytrwal et al. (2014). "Synthesis of strong polycations with improved biological properties". Journal of Biomaterials Research Part A, 102(3), 721-731.

Kataev et al. (2014). Quaternary ammonium derivatives of natural terpenoids. Synthesis and properties. Russian Chemical Bulletin, 63(9), 1884-1900.

Pu, Y., et al. (2016). Synthesis and antibacterial study of sulfobetaine/quaternary ammonium-modified star-shaped poly [2-(dimethylamino) ethyl methacrylate]-based copolymers with an inorganic core. Biomacromolecules, 18(1), 44-55.

Xu, Q., et al. (2015). Polyurethane-coated silica particles with broad-spectrum antibacterial properties. Polymer Chemistry, 6(11), 2011-2022.

Takei, et al. (1999). Investigation of the Structure of Surface Hydroxyl Groups on Silica Chemical Reaction and Molecular Adsorption Method. Journal of the Society of Powder Technology, Japan, 36(3), 179-184.

* cited by examiner

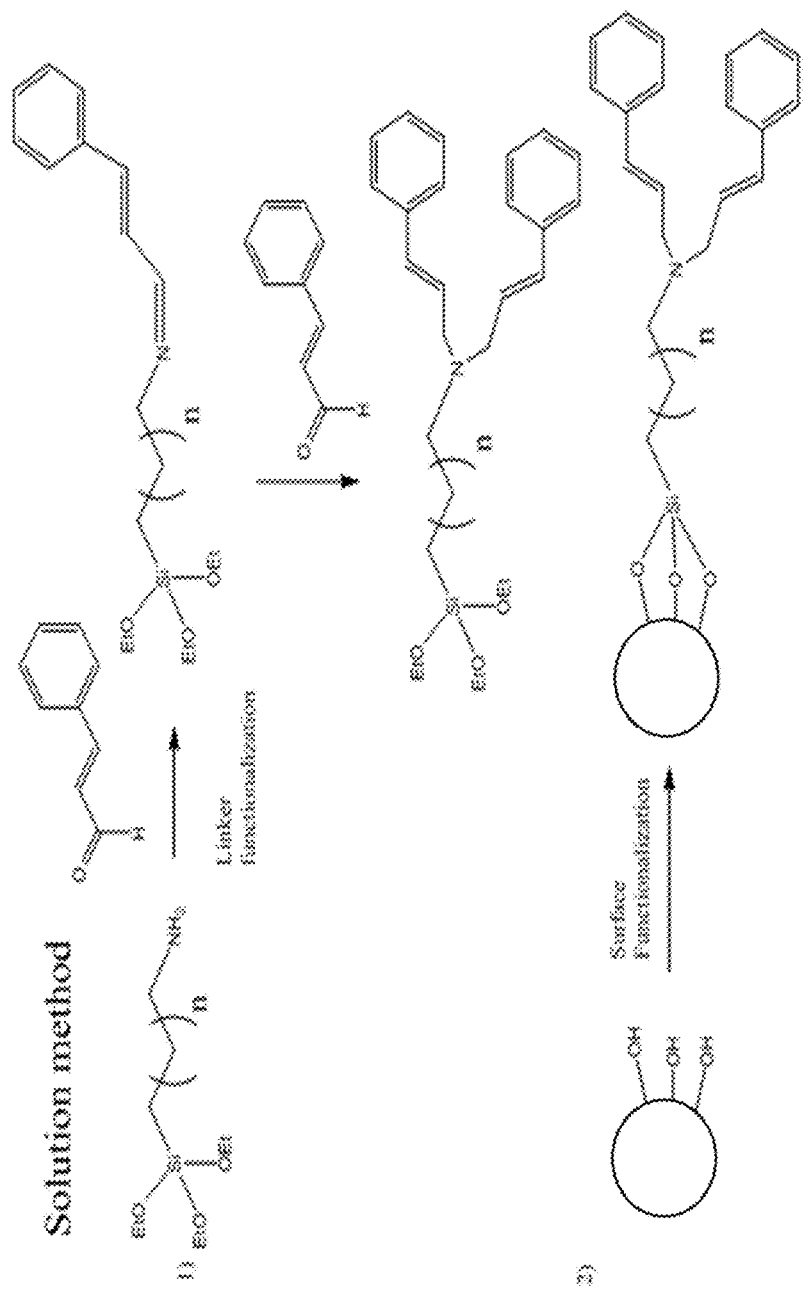
FIGURE 7 - continued

Step 1: linker attachment
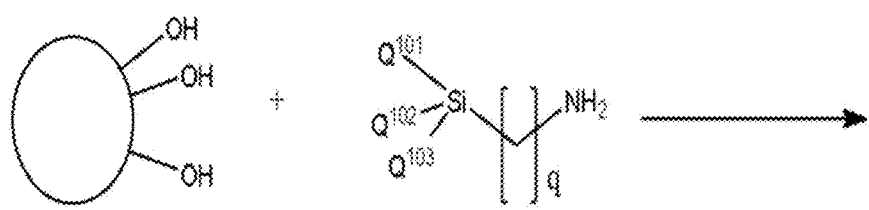
Step 2: elongation (I)
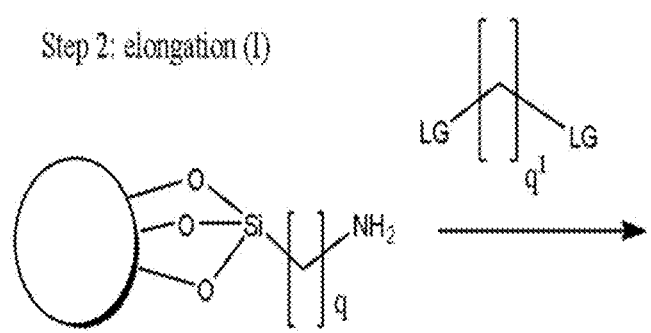
Step 3: elongation (II)
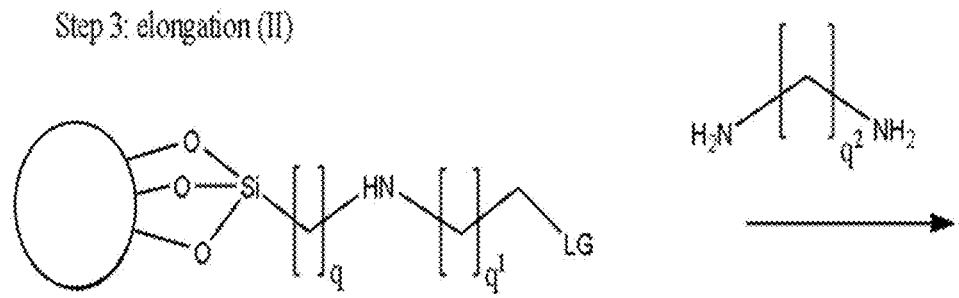
FIGURE 8

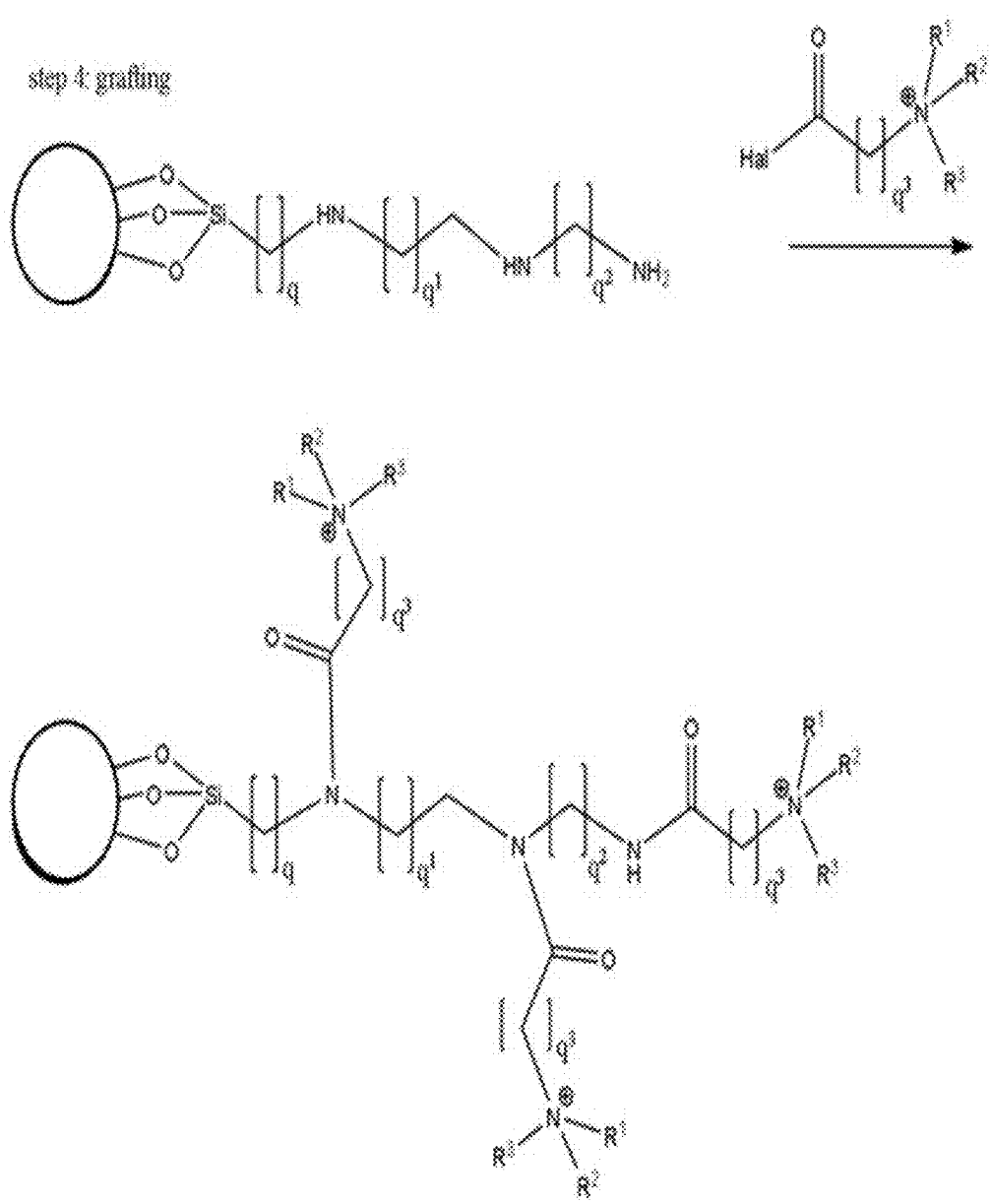
FIGURE 8 - continued

Step 1: linker elongation (I)
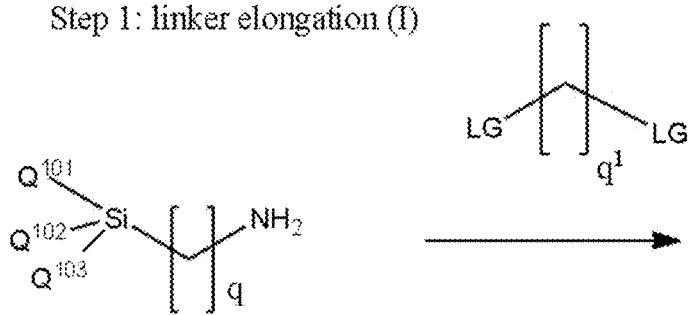
Step 2: linker elongation (II)
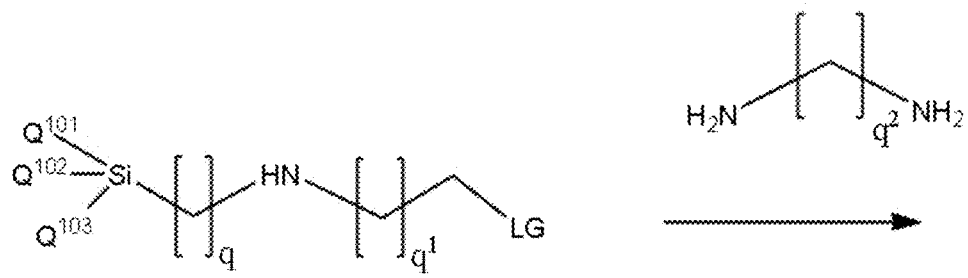
step 3: grafting
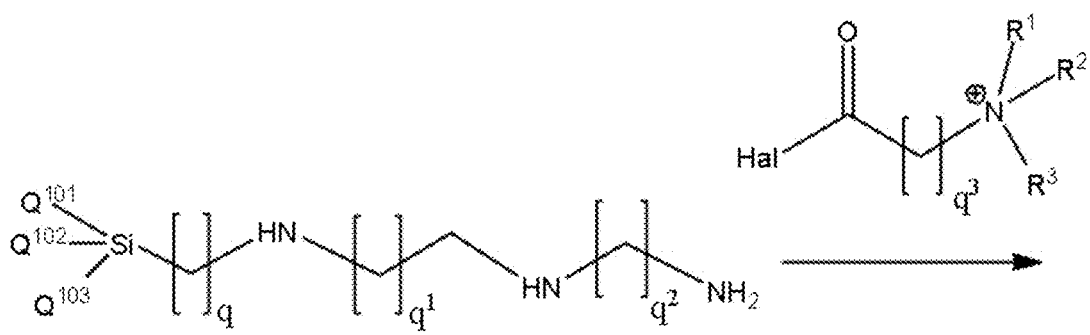
FIGURE 9

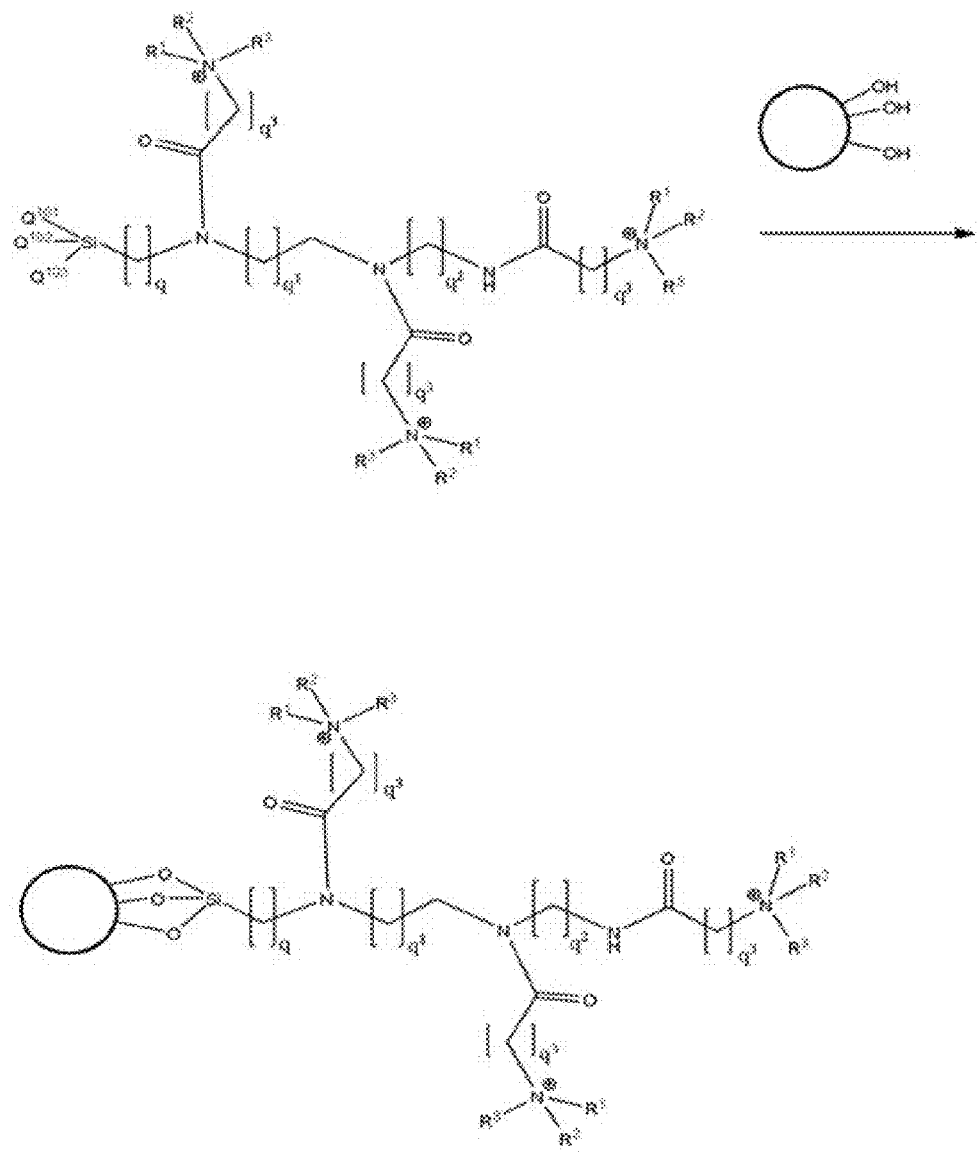
FIGURE 9 - continued

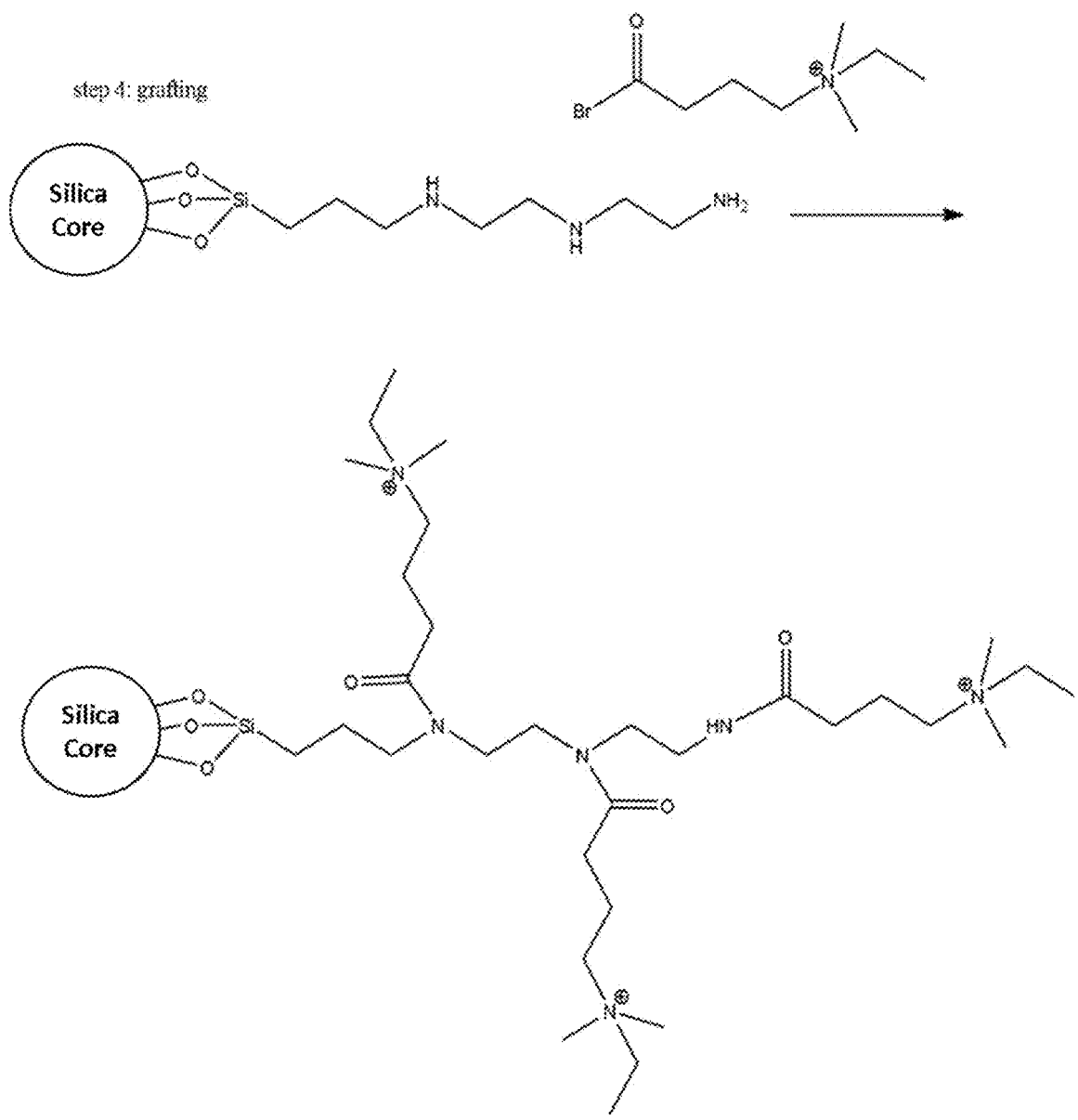
FIGURE 10 - continued

Step 1: linker elongation (I)
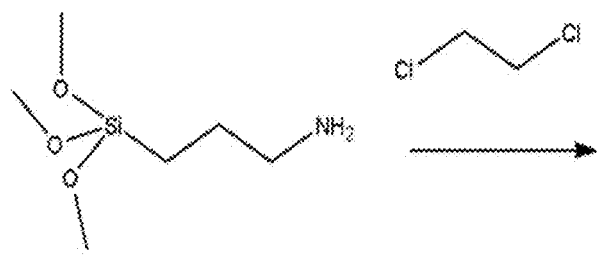
Step 2: linker elongation (II)
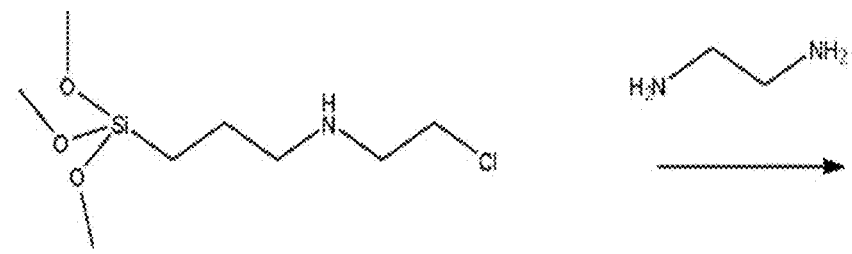
Step 3: grafting
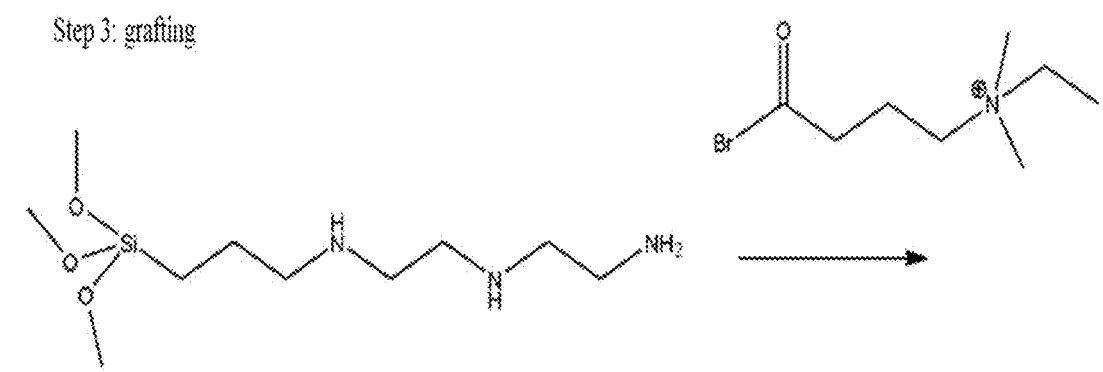
FIGURE 11

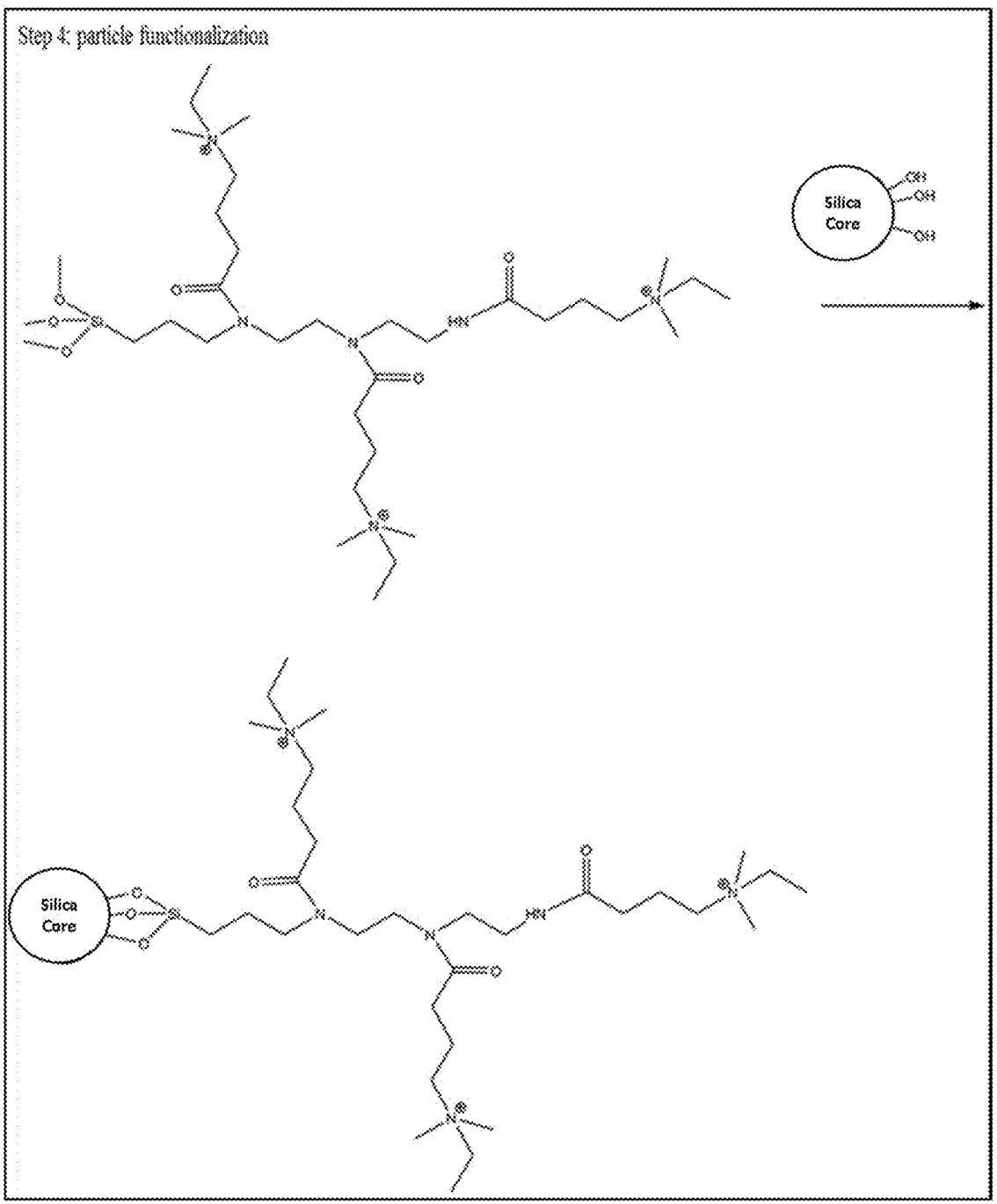
FIGURE 11-continued

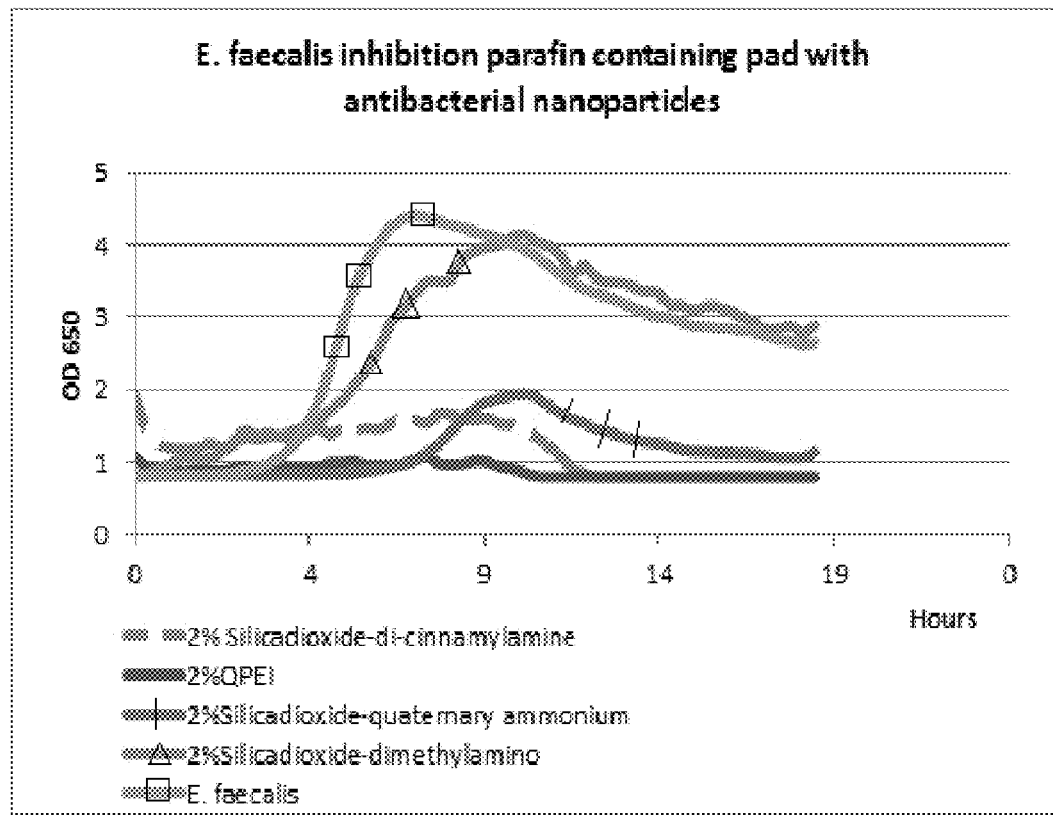
FIUGRE 13
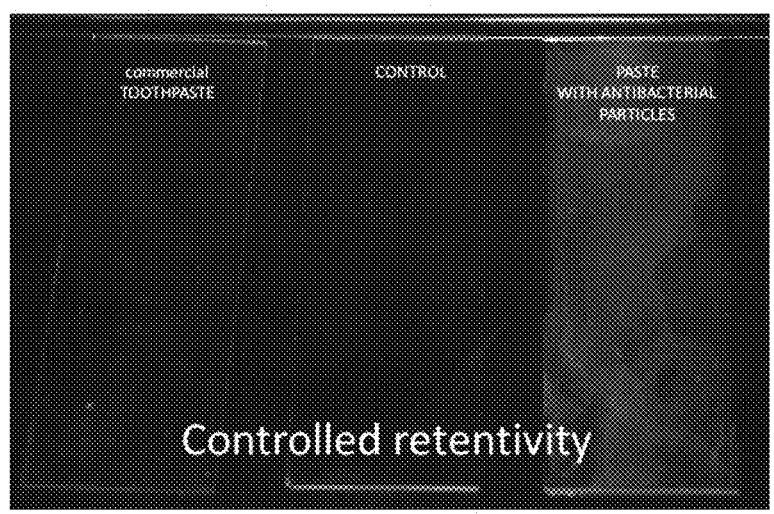
FIGURE 14

ANTI-MICROBIAL PARTICLES AND METHODS OF USE THEREOF

CROSS-REFERENCE TO RELATED APPLICATIONS

This application claims priority from U.S. Provisional Patent Application No. 62/551,813 filed Aug. 30, 2017, U.S. Provisional Patent Application No. 62/551,806 filed Aug. 30, 2017, and U.S. Provisional Patent Application No. 62/644,604 filed Mar. 19, 2018, which are hereby incorporated by reference by their entirety.

FIELD OF THE INVENTION

This invention relates to anti-microbial active particles, compositions and uses thereof for inhibiting bacterial growth on surfaces or devices. This invention further discloses methods of making such anti-microbial active particles.

BACKGROUND OF THE INVENTION

The overwhelming diversity of bacteria in one individual's skin, gastro intestinal tract and oral cavity is well documented, demonstrating a complex ecosystem anatomically and dynamically in which poly-microbial biofilms are the norm.

Bioalms formed on tissues outside and inside the organism are the major cause of infectious diseases. For example in the oral cavity, biofilm formed on dental hard or soft tissue are the major cause of caries and periodontal disease (Sbordone L., Bortolaia C., *Clin Oral Investig* 2003;7:181-8). Bacterial biofilm forms on both natural and artificial surfaces.

Special attention is paid in recent years to artificial surfaces contacting organisms, as these surfaces lack the epithelial shedding, a major natural mechanism to combat biofilms, thus biofilm accumulation is becoming a major source of medical problems that may result in life threatening complications. Two major factors influence the susceptibility of a surface to accumulate bacteria: surface roughness and the surface-free energy which is a property of the material used. Surface roughness has a higher influence on the adhesion of bacteria than surface-free energy. In this context, artificial restorative materials typically have a higher surface roughness than natural surfaces, and therefore are more prone to bacterial accumulation. Therefore, the development of new materials that diminishes biofilm formation is a critical topic.

The ultimate goal of the development of materials with anti-biofilm properties is to improve health and reduce disease occurrence. None of the existing medical devices can guarantee immediate and comprehensive elimination of biofilm or prevention of secondary infection.

For example, in order to sustain the oral defense, dental materials with the following-biofilm properties are sought after: (1) inhibition of initial binding of microorganisms (2) preventing biofilm growth, (3) affecting microbial metabolism in the biofilm, (4) killing biofilm bacteria, and (5) detaching biofilm (Busscher H J, Rinastiti M, Siswomihardjo W, van der Mei H C., J Dent Res, 2010;89:657-65; Marsh P D. *J Dent,* 2010; 38).

Resin-based dental composites are complex dental materials that consist of a hydrophobic resin matrix and less hydrophobic filler particles, which implies that a resin-based dental composite surface is never a homogeneous interface but rather one that produces matrix-rich and filler-poor areas, as well as matrix-poor and filler-rich areas (Ionescu A, Wutscher E, Brambilla E, Schneider-Feyrer S, Giessibl F J, Hahnel S.; *Ear Oral Sci* 2012;1.20:458-65).

Biofilms on composites can cause surface deterioration. Polishing, as well as differences in the composition of the resin-based composite, may have an impact on biofilm formation on the resin-based composite surface (Ono M. et al., *Dent Mater J,* 2007;26 :613-22). Surface degradation of resin composites driven by polishing leads to increased roughness, changes in micro hardness, and filler particle exposure upon exposure to biofilms in vitro. Furthermore, biofilms on composites can cause surface deterioration.

There still remains a need for anti-microbial active materials and it would be advantageous to have an extended variety of anti-microbial active materials which are cost-effective, non-toxic and easy to apply to contaminated surfaces and devices, especially in dental products.

SUMMARY OF THE INVENTION

This invention provides anti-microbial active functionalized particles, which can be coated on a surface, embedded in a matrix or embedded in raw materials to form compositions demonstrating a broad spectrum of anti-microbial activity. The compositions of the invention are preferably formulated for topical, on mucosal surfaces, skin surfaces, dental surfaces and/or wounds (chronic and acute) administration. The anti-microbial particles prevent the formation of biofilm on surfaces and devices and treat, break down or kill biofilm or bacteria within. Furthermore, this invention provides versatile and cost-effective methodology for the preparation of the anti-microbial active particles.

This invention is based on the surprising discovery that particles comprising an inorganic or organic inert core, and oligomeric or polymeric anti-microbial active group chemically bound to the core directly or via linker—at a surface density of at least one anti-microbial active group per 10 sq. nm, show a broad spectrum of anti-microbial activity when applied to or incorporated onto surfaces and devices on which the growth of such microbes may otherwise naturally take place. Such anti-microbial activity thus prevents biofilm formation and may treat, break down and/or kill biofilm or bacteria within. In some embodiments, the particles generally include an inert core which can be made of an organic polymeric material or inorganic materials, as described herein and an anti-microbial active group.

In some embodiments, this invention provides an anti-microbial active particle comprising:

(i) an inorganic or organic core; and (ii) polymeric or oligomeric anti-microbial active unit chemically bound to the core directly or indirectly (via a third linker) to the core;

wherein the polymeric or oligomeric anti-microbial active unit comprises more than one monomeric unit comprising an anti-microbial active group; and wherein the number of the anti-microbial active groups per each anti-microbial active unit is between 2-200.

In another embodiment, the particle is represented by structures (1)-(3):

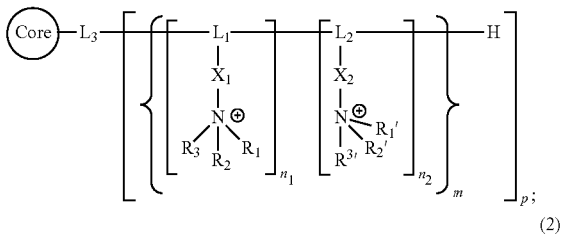
(1)

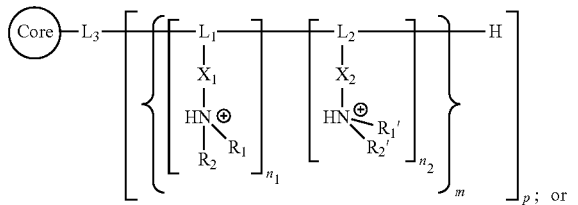
(2)

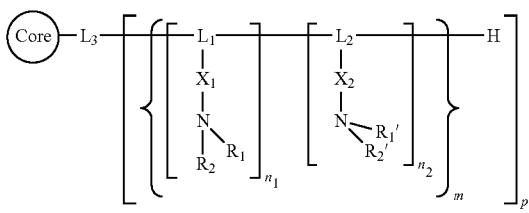
(3)

wherein
the core is an organic polymer or an inorganic material;
$L_1$ is a bond or a first linker;
$L_2$ is a second linker;
$L_3$ is a bond or a third linker;
$R_1$ and $R_1'$ are each independently alkyl, terpenoid, cycloalkyl, aryl, heterocycle, alkenyl, alkynyl or any combination thereof;
$R_2$ and $R_2'$ are each independently alkyl, terpenoid, cycloalkyl, aryl, heterocycle, alkenyl, alkynyl or any combination thereof;
$R_3$ and $R_3'$ are each independently not present, hydrogen, alkyl, terpenoid moiety, cycloalkyl, aryl, heterocycle, alkenyl, alkynyl or any combination thereof; wherein if $R_3$ or $R_3'$ is not present the nitrogen is not charged;
$X_1$ and $X_2$ is each independently a bond, alkylene, alkenylene, or alkynylene;
p defines the surface density of anti-microbial active units per one sq nm ($nm^2$) of the core surface, wherein said density is of between 0.01-30 anti-microbial active groups per one sq nm ($nm^2$) of the core surface of the particle;
$n_1$ is each independently an integer between 0 to 200;
$n_2$ is each independently an integer between 0 to 200;
wherein $n_1+n_2 \geq 2$;
m is an integer between 1 to 200 and the repeating unit is the same or different.

In one embodiment, this invention provides a composition comprising a liquid or solid matrix embedding a plurality of particles of this invention, wherein the particles are embedded in the matrix through covalent or non-covalent interactions.

In one embodiment, this invention provides raw materials comprising the particles of this invention for the preparation of medical devices such as stents or catheters, specifically catheters made of polymeric materials, wherein the particles are embedded in the raw material through covalent or non-covalent interactions.

In one embodiment, this invention provides a pharmaceutical composition comprising the particles of this invention.

In one embodiment, the invention is directed to a packaging composition comprising a thermoplastic polymer and/or hydrogel embedded with particles of this invention. In another embodiment, the thermoplastic polymer and/or hydrogel is embedded with a mixture of two or more different particles of this invention. In another embodiment, the packaging composition is used in the packaging of food, beverage, pharmaceutical ingredients, medical devices, surgical equipment before operation, preoperation equipment, cosmetics, and sterilized equipment/materials.

In one embodiment, this invention provides a method for inhibiting or preventing biofilm formation or growth, comprising applying onto a susceptible or infected surface or a medical device an anti-microbial particle, combination of particles or a composition comprising thereof.

In another embodiment, this invention provides a medical device of this invention for use in inhibiting or preventing biofilm formation or growth.

In one embodiment, this invention provides a method for treating, breaking down or killing biofilm or bacteria within, comprising applying onto a susceptible or infected surface or a medical device an anti-microbial particle, combination of particles or a composition comprising thereof.

In some embodiments, the anti-bacterial compositions of this invention affect annihilation of at least about 99% of the contacted bacteria, preferably, at least about 99.99% of the contacted bacteria.

It was further surprisingly discovered that the particles of this invention maintain high anti-microbial properties over time without leaching out and with no alteration of the properties of the hosting matrix.

The particles of this invention demonstrate enhanced anti-bacterial activity originating from the presence of closely packed anti-bacterial groups on a given particle's surface.

In one embodiment, this invention provides a packaging composition comprising a thermoplastic polymer and a particle of this invention embedded therein. In another embodiment, the packaging composition comprises a mixture of two or more different particles of this invention. In another embodiment, the packaging is for use for packaging of food, beverage, pharmaceutical ingredients, medical devices, surgical equipment before operation, pre-operation equipment, cosmetics, and sterilized equipment/materials.

In one embodiment, this invention provides a medical device comprising a particle of this invention embedded therein. In another embodiment, the medical device comprises a mixture of two or more different particles of this invention. In another embodiment, the medical device includes a stent or catheter.

It was further surprisingly discovered that the particles of this invention maintain high anti-microbial properties over time without leaching out and with no alteration of the properties of the hosting matrix.

BRIEF DESCRIPTION OF THE FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A: Overall scheme of the particles; and FIG. 1B: detailed scheme of a monomeric unit.

FIG. 2A: Self-polymerized linker attached to a core. FIG. 2B: Self-polymerized linker before attachment to a core. FIG. 2C: [Comparison of polymerization of the silane groups (mode B) versus simple silanization (mode A). Circles denote cores.

FIG. 5A: a pathway using reductive amination to achieve tertiary amine, followed by an alkylation reaction; FIG. 5B: a pathway using stepwise alkylation reactions; and FIG. 5C: a pathway of reacting a linker functionalized with a leaving group (e.g., Cl or other halogen) with tertiary amine $R^1$ and $R^2$ represent $C_1$-$C_4$ alkyls such as methyl, ethyl, propyl or isopropyl. $R^1$ and $R^2$ may be different or the same group. Y represents any leaving group, for example Cl, Br or I, or a sulfonate (e.g., mesyl, tosyl).

FIG. 8 depicts a representative scheme for the preparation of particles according to this invention by a solid support method, wherein the anti-microbial unit has an oligomeric or polymeric backbone (more than one monomeric unit). The circles represent a core. The starting material is a core terminated on the surface with hydroxyl groups; $^{101}Q$; $^{102}Q$ and $^{103}Q$ and independently alkoxy, alkyl or aryl; LG is Cl, Br, I, mesylate, tosylate or triflate; Hal is Cl, Br or I; q, $q^1$, $q^2$ and $q^3$ are independently an integer between 0-16; $R^1$ and $R^2$ are each independently alkyl, terpenoid, cycloalkyl, aryl, heterocycle, a conjugated alkyl, alkenyl or any combination thereof; and $R^3$ is nothing, hydrogen, alkyl, terpenoid moiety, cycloalkyl, aryl, heterocycle, alkenyl, alkynyl or any combination thereof.

FIG. 9 depicts a representative scheme for the preparation of particles according to this invention in a solution method, wherein the anti-microbial unit has more than one monomeric unit (i.e has an oligomeric or polymeric backbone). The circles represent a core. The starting material is a core terminated on the surface with hydroxyl groups; $Q^{101}$, $Q^{102}$ and $Q^{103}$ and independently alkoxy, alkyl or aryl; LG is Cl, Br, I, mesylate, tosylate or triflate; Hal is Cl, Br or I; q, $q^1$, $q^2$ and $q^3$ are independently an integer between 0-16; $R^1$ and $R^2$ are each independently alkyl, terpenoid, cycloalkyl, aryl, heterocycle, a conjugated alkyl, alkenyl or any combination thereof; and $R^3$ is nothing, hydrogen, alkyl, terpenoid moiety, cycloalkyl, aryl, heterocycle, alkenyl, alkynyl or any combination thereof.

FIG. 11 depicts a scheme for the preparation of silica based anti-microbial particles according to this invention comprising dimethylethylammonium as the anti-microbial active group, in a solution method, wherein the anti-microbial unit has more than one monomeric unit (i.e has an oligomeric or polymeric backbone).

FIG. 13 depicts *E. faecalis* inhibition parafin containing pad with antibacterial nanop articles.

FIG. 14 depicts particles retention onto glass slides with commercially available toothpaste (control); with toothpaste with $SiO_2$ particles (control); and with toothpaste with $SiO_2$ particles having tertiary amine with two cinnamyl groups.

Figure 1A:
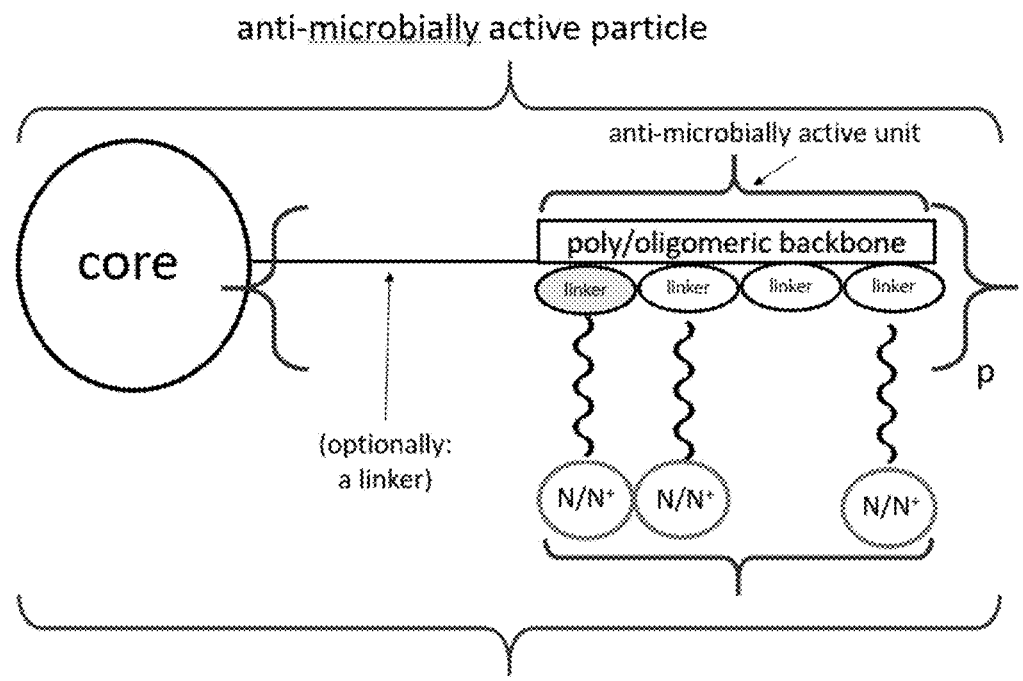
FIGS. 1A-1B depict a schematic illustration of the anti-microbial active particle of this invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that this invention may be practiced without these specific details. In other instances, well-known methods, procedures, and components have not been described in detail so as not to obscure this invention.

Particles

This invention provides anti-microbial active functionalized particles, and compositions comprising thereof demonstrating a broad spectrum of anti-microbial activity.

In some embodiments, this invention provides an anti-microbial active particle comprising:
(i) an inorganic or organic core; and
(ii) polymeric or oligomeric anti-microbial active unit chemically bound to the core directly or indirectly (via a third linker) to the core;
wherein the polymeric or oligomeric anti-microbial active unit comprises more than one monomeric unit comprising an anti-microbial active group; and
wherein the number of the anti-microbial active groups per each anti-microbial active unit is between 2-200.

Figure 1B:
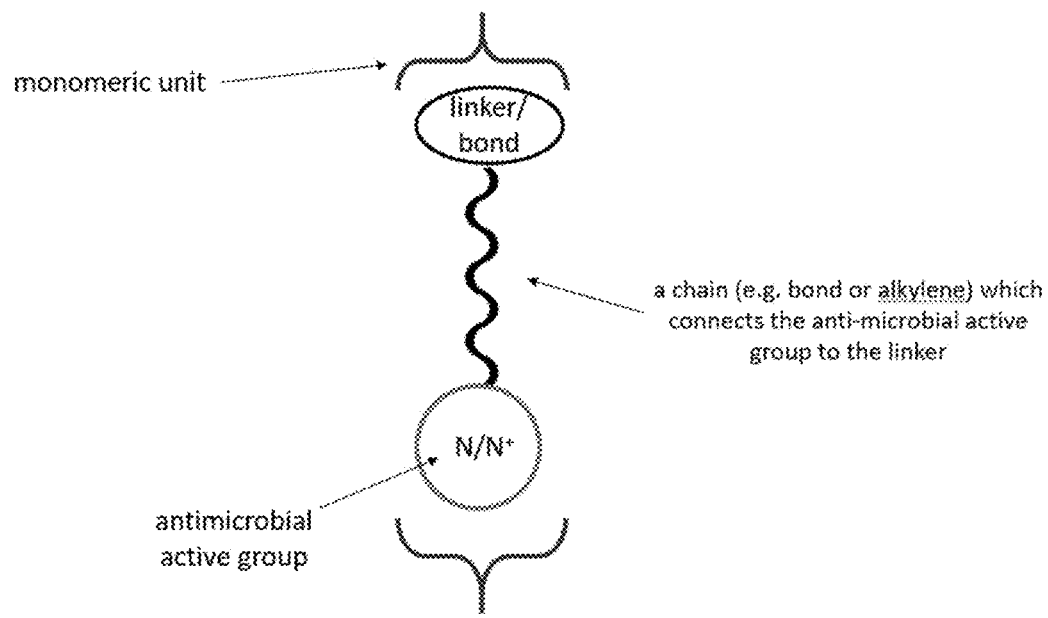

In another embodiment, the monomeric units are connected to each other via the second linker or a first linker or combination thereof. In another embodiment, each monomeric unit comprises an anti-microbial active group. In another embodiment, an oligomeric/polymeric anti-microbial active unit comprises at least two anti-microbial active groups. In another embodiment, FIGS. 1A-1B illustrate schematically the anti-microbial active particles of this invention.

In another embodiment, this invention provides a particle represented by structure (1):

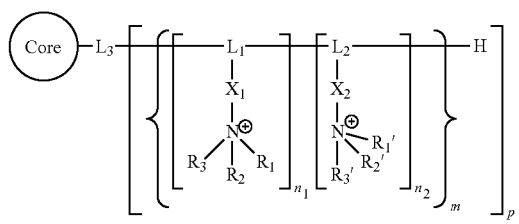

(1)

wherein
the core is an organic polymer or an inorganic material;
$L_1$ is a bond or a first linker;

$L_2$ is a second linker;
$L_3$ is a bond or a third linker;
$R_1$ and $R_1'$ are each independently alkyl, terpenoid, cycloalkyl, aryl, heterocycle, alkenyl, alkynyl or any combination thereof;
$R_2$ and $R_2'$ are each independently alkyl, terpenoid, cycloalkyl, aryl, heterocycle, alkenyl, alkynyl or any combination thereof;
$R_3$ and $R_3'$ are each independently not present, hydrogen, alkyl, terpenoid moiety, cycloalkyl, aryl, heterocycle, alkenyl, alkynyl or any combination thereof; wherein if $R_3$ or $R_3'$ is not present the nitrogen is not charged;
$X_1$ and $X_2$ is each independently a bond, alkylene, alkenylene, or alkynylene;
p defines the surface density of anti-microbial active units per one sq nm ($nm^2$) of the core surface, wherein said density is of between 0.01-30 anti-microbial active groups per one sq nm ($nm^2$) of the core surface of the particle;
$n_1$ is each independently an integer between 0 to 200;
$n_2$ is each independently an integer between 0 to 200;
wherein $n_1+n_2 \geq 2$;
m is an integer between 1 to 200 and the repeating unit is the same or different.

In another embodiment, at least one of $R_1$, $R_2$, $R_3$ and/or at least one of $R_1'$, $R_2'$, $R_3'$ are hydrophobic in structure 1.

In another embodiment, this invention provides particle represented by structure (2):

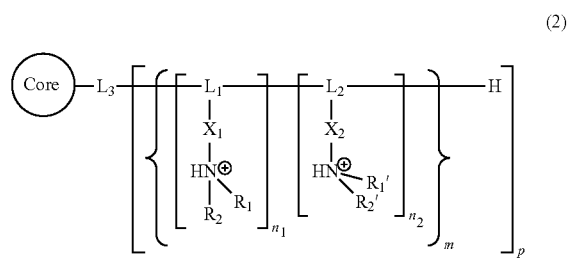

(2)

wherein,
the core is an organic polymer or an inorganic material;
$L_1$ is a bond or a first linker;
$L_2$ is a second linker;
$L_3$ is a bond or a third linker;
$R_1$ and $R_1'$ are each independently alkyl, terpenoid, cycloalkyl, aryl, heterocycle, alkenyl, alkynyl or any combination thereof;
$R_2$ and $R_2'$ are each independently alkyl, terpenoid, cycloalkyl, aryl, heterocycle, alkenyl, alkynyl or any combination thereof;
$X_1$ and $X_2$ is each independently a bond, alkylene, alkenylene, or alkynylene;
p defines the surface density of anti-microbial active units per one sq nm ($nm^2$) of the core surface, wherein said density is of between 0.01-30 anti-microbial active groups per one sq nm ($nm^2$) of the core surface of the particle;
$n_1$ is each independently an integer between 0 to 200;
$n_2$ is each independently an integer between 0 to 200;
wherein $n_1+n_2 \geq 2$;
m is an integer between 1 to 200 and the repeating unit is the same or different.

In another embodiment, at least one of $R_1$, $R_2$ and/or at least one of $R_1'$, $R_2'$ are hydrophobic in structure 2.

In another embodiment, this invention provides a particle represented by structure (3):

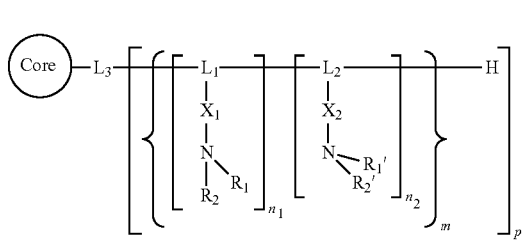

(3)

wherein
the core is an organic polymer or an inorganic material;
$L_1$ is a bond or a first linker;
$L_2$ is a second linker;
$L_3$ is a bond or a third linker;
$R_1$ and $R_1'$ are each independently alkyl, terpenoid, cycloalkyl, aryl, heterocycle, alkenyl, alkynyl or any combination thereof;
$R_2$ and $R_2'$ are each independently alkyl, terpenoid, cycloalkyl, aryl, heterocycle, alkenyl, alkynyl or any combination thereof;
$X_1$ and $X_2$ is each independently a bond, alkylene, alkenylene, or alkynylene;
p defines the surface density of anti-microbial active units per one sq nm ($nm^2$) of the core surface, wherein said density is of between 0.01-30 anti-microbial active groups per one sq nm ($nm^2$) of the core surface of the particle;
$n_1$ is each independently an integer between 0 to 200;
$n_2$ is each independently an integer between 0 to 200;
wherein $n_1+n_2 \geq 2$;
m is an integer between 1 to 200 and the repeating unit is the same or different.

In another embodiment, at least one of $R_1$, $R_2$ and/or at least one of $R_1'$, $R_2'$ are hydrophobic in structure 3.

In another embodiment the hydrogen may or may not be present in structures 1-3 at the polymeric or oligomeric anti-microbial active unit end side.

In another embodiment, the anti-microbial particles are presented by the following structure:

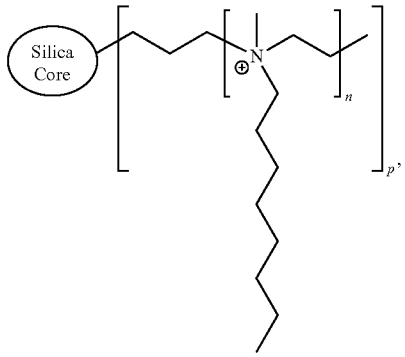

where n=2-200; and p defines the surface density of the oligomeric/polymeric anti-microbial active units per one sq nm ($nm^2$) of the core surface, wherein the density is of between 0.01-30 anti-microbial active units per one sq nm ($nm^2$) of the core surface of the particle. In another embodiment, n=2-3. In another embodiment, n=3-20. In another embodiment, n=20-50. In another embodiment, n=50-100. In another embodiment, n=100-200.

In another embodiment, the term "anti-microbial active group" and the term "monomeric anti-microbial active group" refer to the same and comprise a protonated tertiary amine, a tertiary amine or a quaternary ammonium, as represented by the following formulas:

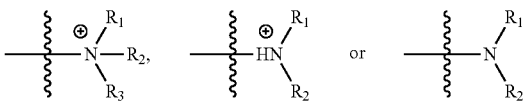

wherein:
$R_1$ is alkyl, terpenoid, cycloalkyl, aryl, heterocycle, alkenyl, alkynyl or any combination thereof;
$R_2$ is alkyl, terpenoid, cycloalkyl, aryl, heterocycle, alkenyl, alkynyl or any combination thereof;
$R_3$ is nothing, hydrogen, alkyl, terpenoid moiety, cycloalkyl, aryl, heterocycle, a conjugated alkyl, alkenyl, alkynyl or any combination thereof; wherein if $R_3$ is nothing, the nitrogen is not charged.

In another embodiment, at least one of $R_1$, $R_2$ or $R_3$ is hydrophobic.

The anti-microbial active groups of this invention are chemically bound to the core at a surface density of at least one anti-microbial active group per 10 sq. nm of the core surface. In another embodiment at least 1 anti-microbial group per 1 sq nm of the core surface. In another embodiment between 0.001-400 anti-microbial groups per sq nm of the core surface. In another embodiment between 0.001-300 anti-microbial groups per sq nm of the core surface. In another embodiment between 0.01-300 anti-microbial groups per sq nm of the core surface. In another embodiment between 0.001-250 anti-microbial groups per sq nm of the core surface. In another embodiment between 0.001-200 anti-microbial groups per sq nm of the core surface. In another embodiment between 0.001-150 anti-microbial groups per sq nm of the core surface. In another embodiment between 0.001-100 anti-microbial groups per sq nm of the core surface. In another embodiment between 0.001-50 anti-microbial groups per sq nm of the core surface. In another embodiment between 0.001-20 anti-microbial groups per sq nm of the core surface. In another embodiment between 0.001-17 anti-microbial groups per sq nm of the core surface. In another embodiment between 0.001-15 anti-microbial groups per sq nm of the core surface. In another embodiment between 0.001-10 anti-microbial groups per sq nm of the core surface. In another embodiment between 0.001-4 anti-microbial groups per sq nm of the core surface. In another embodiment between 0.001-1 anti-microbial groups per sq nm of the core surface. In another embodiment between 50-400 anti-microbial groups per sq nm of the core surface. In another embodiment between 100-400 anti-microbial groups per sq nm of the core surface. In another embodiment between 50-100 anti-microbial groups per sq nm of the core surface. In another embodiment between 100-150 anti-microbial groups per sq nm of the core surface. In another embodiment between 150-200 anti-microbial groups per sq nm of the core surface. In another embodiment between 200-250 anti-microbial groups per sq nm of the core surface. In another embodiment between 250-300 anti-microbial groups per sq nm of the core surface. In another embodiment between 1-4 anti-microbial groups per sq nm of the core surface. In another embodiment between 1-6 anti-microbial groups per sq nm of the core surface. In another embodiment between 1-20 anti-microbial groups per sq nm of the core surface. In another embodiment between 1-10 anti-microbial groups per sq nm of the core surface. In another embodiment between 1-15 anti-microbial groups per sq nm of the core surface.

In some embodiments, the number of the anti-microbial active groups per each oligomeric or polymeric anti-microbial active unit is between 2-200. In another embodiment, the number of the anti-microbial active groups per each oligomeric or polymeric anti-microbial active unit is between 2-150. In another embodiment, the number of the anti-microbial active groups per each oligomeric or polymeric anti-microbial active unit is between 2-100. In another embodiment, the number of the anti-microbial active groups per each oligomeric or polymeric anti-microbial active unit is between 2-50. In another embodiment, the number of the anti-microbial active groups per each oligomeric or polymeric anti-microbial active unit is between 2-30. In another embodiment, the number of the anti-microbial active groups per each oligomeric or polymeric anti-microbial active unit is between 2-20. In another embodiment, the number of the anti-microbial active groups per each oligomeric or polymeric anti-microbial active unit is between 2-10. In another embodiment, the number of the anti-microbial active groups per each oligomeric or polymeric anti-microbial active unit is between 50-100. In another embodiment, the number of the anti-microbial active groups per each oligomeric or polymeric anti-microbial active unit is between 100-150. In another embodiment, the number of the anti-microbial active groups per each oligomeric or polymeric anti-microbial active unit is between 150-200.

In some embodiments, the number of the monomeric units per each oligomeric or polymeric anti-microbial active unit is between 2-200. In another embodiment, the number of the monomeric units per each oligomeric or polymeric anti-microbial active unit is between 2-150. In another embodiment, the number of the monomeric units per each oligomeric or polymeric anti-microbial active unit is between 2-100. In another embodiment, the number of the monomeric units per each oligomeric or polymeric anti-microbial active unit is between 2-50. In another embodiment, the number of the monomeric units per each oligomeric or polymeric anti-microbial active unit is between 2-30. In another embodiment, the number of monomeric units per each oligomeric or polymeric anti-microbial active unit is between 2-20. In another embodiment, the number of the monomeric units per each oligomeric or polymeric anti-microbial active unit is between 2-10. In another embodiment, the number of the monomeric units per each oligomeric or polymeric anti-microbial active unit is between 50-100. In another embodiment, the number of the monomeric units per each oligomeric or polymeric anti-microbial active unit is between 100-150. In another embodiment, the number of the monomeric units per each oligomeric or polymeric anti-microbial active unit is between 150-200.

In another embodiment, the particle of structures (1) to (3) has an inorganic core. In another embodiment, the particle of structure (1) to (3) has an organic core. In another embodiment, the organic core is a polymeric organic core. In another embodiment, the core is inert. In one embodiment, the particles of this invention represented by structures (1)-(3) comprise an anti-microbial active group of —$^+N(R_1)(R_2)(R_3)$, —$^+NH(R_1)(R_2)$, —$N(R_1)(R_2)$ —$^+N(R_1')(R_2')(R_3')$, —$^+NH(R_1')(R_2')$ or —$N(R_1')(R_2')$. In one embodiment $R_1$ and/or $R_1'$, $R_2$ and/or $R_2'$ and $R_3$ and/or $R_3'$ are the same or different and are independently alkyl, terpenoid, cycloalkyl, aryl, heterocycle a conjugated alkyl, alkenyl, alkynyl or any combination thereof. In another embodiment, $R_1$, $R_2$ and $R_3$ are independently an alkyl. In another embodiment, $R_1$ and/or $R_1'$, $R_2$ and/or $R_2'$ and $R_3$ and/or $R_3'$ are independently a terpenoid. In another embodiment, $R_1$ and/or $R_1'$, $R_2$ and/or $R_2'$ and $R_3$ and/or $R_3'$ are independently a cycloalkyl. In another embodiment, $R_1$ and/or $R_1'$, $R_2$ and/or $R_2'$ and $R_3$ and/or $R_3'$ are independently an aryl. In another embodiment, $R_1$ and/or $R_1'$, $R_2$ and/or $R_2'$ and $R_3$ and/or $R_3'$ are independently a heterocycle. In another embodiment, $R_1$ and/or $R_1'$, $R_2$ and/or $R_2'$ and $R_3$ and/or $R_3'$ are independently a conjugated alkyl. In another embodiment, $R_1$ and/or $R_1'$, $R_2$ and/or $R_2'$ and $R_3$ and/or $R_3'$ are independently an alkenyl. In another embodiment, $R_1$ and/or $R_1'$, $R_2$ and/or $R_2'$ and $R_3$ and/or $R_3'$ are independently an alkynyl. In another embodiment, $R_3$ is nothing. In another embodiment, $R_3$ and/or $R_3'$ is hydrogen. In another embodiment at least one of $R_1$ and/or $R_1'$, $R_2$ and/or $R_2'$ and $R_3$ and/or $R_3'$ is hydrophobic alkyl, terpenoid, cycloalkyl, aryl, heterocycle, a conjugated alkyl, alkenyl, alkynyl or any combination thereof. Each represents a separate embodiment of this invention.

In another embodiment $R_1$ and $R_1'$ are the same. In another embodiment $R_2$ and $R_2'$ are the same. In another embodiment $R_3$ and $R_3'$ are the same. In another embodiment $R_1$ and $R_1'$ are different. In another embodiment $R_2$ and $R_2'$ are different. In another embodiment $R_3$ and $R_3'$ are different.

As used herein, the term "alkyl" or "alkylene" refer to linear- or branched-chain alkyl group containing up to about 24 carbons unless otherwise specified. In one embodiment, an alkyl includes $C_1$-$C_3$ carbons. In one embodiment, an alkyl includes $C_1$-$C_4$ carbons. In one embodiment, an alkyl includes $C_1$-$C_5$ carbons. In another embodiment, an alkyl includes $C_1$-$C_6$ carbons. In another embodiment, an alkyl includes $C_1$-$C_8$ carbons. In another embodiment, an alkyl includes $C_1$-$C_{10}$ carbons. In another embodiment, an alkyl includes $C_1$-$C_{12}$ carbons. In another embodiment, an alkyl includes $C_4$-$C_8$ carbons. In another embodiment, an alkyl includes $C_4$-$C_{10}$ carbons. In another embodiment, an alkyl include $C_4$-$C_{18}$ carbons. In another embodiment, an alkyl include $C_4$-$C_{24}$ carbons. In another embodiment, an alkyl includes $C_1$-$C_{18}$ carbons. In another embodiment, an alkyl includes $C_2$-$C_{18}$ carbons. In another embodiment, branched alkyl is an alkyl substituted by alkyl side chains of 1 to 5 carbons. In one embodiment, the alkyl group may be unsubstituted. In another embodiment, the alkyl group may be substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment hydrophobic alkyl refers to an alkyl having at least four carbons. In another embodiment hydrophobic alkyl refers to a $C_4$-$C_{24}$ alkyl. In another embodiment hydrophobic alkyl refers to a $C_4$-$C_8$ alkyl. In another embodiment hydrophobic alkyl refers to a $C_4$ alkyl. In another embodiment hydrophobic alkyl refers to a $C_5$ alkyl. In another embodiment hydrophobic alkyl refers to a $C_6$ alkyl. In another embodiment hydrophobic alkyl refers to a $C_7$ alkyl. In another embodiment hydrophobic alkyl refers to a $C_8$ alkyl.

A "conjugated alkyl" refers to alkyl as defined above having alternative single and double or triple bonds. In another embodiment hydrophobic conjugated alkyl refers to conjugated alkyl having at least four carbons. In another embodiment hydrophobic conjugated alkyl refers to a conjugated alkyl having a $C_4$-$C_8$ alkyl.

As used herein, the term "aryl" refers to any aromatic ring that is directly bonded to another group and can be either substituted or unsubstituted. The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc. Substitutions include but are not limited to: F, Cl, Br, I, $C_1$-$C_5$ linear or branched alkyl, $C_1$-$C_5$ linear or branched haloalkyl, $C_1$-$C_5$ linear or branched alkoxy, $C_1$-$C_5$ linear or branched haloalkoxy, $CF_3$, CN, $NO_2$, —$CH_2CN$, $NH_2$, NH-alkyl, N(alkyl)$_2$, hydroxyl, —OC(O)$CF_3$, —OCH$_2$Ph, —NHCO-alkyl, COOH, —C(O)Ph, C(O)O-alkyl, C(O)H, or —C(O)$NH_2$. In another embodiment hydrophobic aryl refers to aryl having at least six carbons.

The term "alkenyl" or "alkenylene" refers to a substance that includes at least two carbon atoms and at least one double bond. In one embodiment, the alkenyl has 2-7 carbon atoms. In another embodiment, the alkenyl has 2-12 carbon atoms. In another embodiment, the alkenyl has 2-10 carbon atoms. In another embodiment, the alkenyl has 3-6 carbon atoms. In another embodiment, the alkenyl has 2-4 carbon atoms. In another embodiment, the alkenyl has 4-8 carbon atoms. In another embodiment hydrophobic alkenyl refers to alkenyl having at least four carbons. In another embodiment hydrophobic alkenyl refers to a $C_4$-$C_8$ alkenyl.

The term "alkynyl" or "alkynylene" refers to a substance that includes at least two carbon atoms and at least one triple bond. In one embodiment, the alkynyl has 2-7 carbon atoms. In another embodiment, the alkynyl has 2-12 carbon atoms. In another embodiment, the alkynyl has 2-10 carbon atoms. In another embodiment, the alkynyl has 3-6 carbon atoms. In another embodiment, the alkynyl has 2-4 carbon atoms. In another embodiment, the alkynyl has 3-6 carbon atoms. In another embodiment, the alkynyl has 4-8 carbon atoms. In another embodiment hydrophobic alkynyl refers to alkynyl having at least four carbons. In another embodiment hydrophobic alkynyl refers to a $C_4$-$C_8$ alkenyl.

The term "alkoxy" refers in one embodiment to an alky as defined above bonded to an oxygen. Non-limiting examples of alkoxy groups include: methoxy, ethoxy and isopropoxy.

A "cycloalkyl" group refers, in one embodiment, to a ring structure comprising carbon atoms as ring atoms, which may be either saturated or unsaturated, substituted or unsubstituted. In another embodiment the cycloalkyl is a 3-12 membered ring. In another embodiment the cycloalkyl is a 6 membered ring. In another embodiment the cycloalkyl is a 5-7 membered ring. In another embodiment the cycloalkyl is a 3-8 membered ring. In another embodiment, the cycloalkyl group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the cycloalkyl ring may be fused to another saturated or unsaturated cycloalkyl or heterocyclic 3-8 membered ring. In another embodiment, the cycloalkyl ring is a saturated ring. In another embodiment, the cycloalkyl ring is an unsaturated ring. Non-limiting examples of a cycloalkyl group comprise cyclohexyl, cyclohexenyl, cyclopropyl, cyclopropenyl, cyclopentyl, cyclopentenyl, cyclobutyl, cyclobutenyl, cyclooctyl, cyclooctadienyl (COD), cyclooctaene (COE) etc. In another embodiment hydrophobic cycloalkyl refers to a cycloalkyl having at least six carbons.

A "heterocycle" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 3-8 membered ring. In another embodiment, the heterocycle group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. Non-limiting examples of a heterocyclic rings comprise pyridine, piperidine, morpholine, piperazine, thiophene, pyrrole, benzodioxole, or indole. In another embodiment hydrophobic heterocyclic group refers to a heterocycle having at least six carbons.

In one embodiment, at least one of $R_1$, $R_2$ and $R_3$ and/or at least one of $R_1'$, $R_2'$ and $R_3'$ of structure (1) is hydrophobic. In one embodiment, at least one of $R_1$ and $R_2$ and/or at least one of $R_1'$ and $R_2'$ of structures (2) and (3) is hydrophobic.

The term "hydrophobic" refers to an alkyl, alkenyl or alkynyl having at least four carbons, or the term hydrophobic refers to terpenoid, to cycloalkyl, aryl or heterocycle having at least six carbons. Each possibility represents a separate embodiment of this invention In one embodiment, at least one of $R_1$, $R_2$ and $R_3$ and/or at least one of $R_1'$, $R_2'$ and $R_3'$ of structure (1) is a $C_4$-$C_{24}$ alkyl, $C_4$-$C_{24}$ alkenyl, $C_4$-$C_{24}$ alkynyl or a terpenoid. In one embodiment, at least one of $R_1$ and $R_2$ and/or at least one of $R_1'$ and $R_2'$ of structures (2) and (3) is a $C_4$-$C_{24}$ alkyl, $C_4$-$C_{24}$ alkenyl, $C_4$-$C_{24}$ alkynyl or a terpenoid. Each possibility represents a separate embodiment of this invention.

In one embodiment, at least one of $R_1$, $R_2$ and $R_3$ and/or at least one of $R_1'$, $R_2'$ and $R_3'$ of structure (1) is a $C_4$-$C_8$ alkyl, $C_4$-$C_8$ alkenyl, $C_4$-$C_8$ alkynyl or a terpenoid. In one embodiment, at least one of $R_1$ and $R_2$ and/or at least one of $R_1'$ and $R_2'$ of structures (2) and (3) is a $C_4$-$C_8$ alkyl, $C_4$-$C_8$ alkenyl, $C_4$-$C_8$ alkynyl or a terpenoid. Each possibility represents a separate embodiment of this invention.

In one embodiment, $R_1$ and/or $R_1'$ of structures (1) to (3) is a terpenoid. In another embodiment, $R_1$ and/or $R_1'$ is a terpenoid and $R_2$ and/or $R_2'$ is a $C_1$-$C_4$ alkyl. In another embodiment, the core is an organic polymeric core, $R_3$ and/or $R_3'$ is nothing and $R_1$ and/or $R_1'$ is a terpenoid. In another embodiment, the core is an organic polymeric core, $R_3$ and/or $R_3'$ is a hydrogen and $R_1$ and/or $R_1'$ is a terpenoid. In another embodiment, the core is an inorganic core, $R_3$ and/or $R_3'$ is nothing and $R_1$ and/or $R_1'$ is a terpenoid. In another embodiment, the core is an inorganic core, $R_3$ and/or $R_3'$ is a hydrogen and $R_1$ and/or $R_1'$ is a terpenoid. In another embodiment, the core is an inorganic core, $R_3$ and/or $R_3'$ is a $C_1$-$C_{24}$ alkyl, terpenoid, cycloalkyl, aryl, heterocycle, a conjugated $C_1$-$C_{24}$ alkyl, $C_1$-$C_{24}$ alkenyl, $C_1$-$C_{24}$ alkynyl or any combination thereof and $R_1$ and/or $R_1'$ is a terpenoid.

In one embodiment "p" of structures (1) to (3) defines the surface density of the anti-microbial active units per 1 sq nm of the core surface. In another embodiment "p" is, between 0.01-30 anti-microbial active units per 1 sq nm of the core surface. In another embodiment "p" is, between 0.01-20 anti-microbial active units per 1 sq nm of the core surface.

In another embodiment "p" is, between 0.01-10 anti-microbial active units per 1 sq nm of the core surface. In another embodiment "p" is, between 0.01-15 anti-microbial active units per 1 sq nm of the core surface. In another embodiment "p" is, between 0.01-5 anti-microbial active units per 1 sq nm of the core surface.

In one embodiment, $n_1$ of structures (1) to (3) is between 0-200. In another embodiment, $n_1$ is between 0-10. In another embodiment, $n_1$ is between 10-20. In another embodiment, $n_1$ is between 20-30. In another embodiment, $n_1$ is between 30-40. In another embodiment, $n_1$ is between 40-50. In another embodiment, $n_1$ is between 50-60. In another embodiment, $n_1$ is between 60-70. In another embodiment, $n_1$ is between 70-80. In another embodiment, $n_1$ is between 80-90. In another embodiment, $n_1$ is between 90-100. In another embodiment, $n_1$ is between 100-110. In another embodiment, $n_1$ is between 110-120. In another embodiment, $n_1$ is between 120-130. In another embodiment, $n_1$ is between 130-140. In another embodiment, $n_1$ is between 140-150. In another embodiment, $n_1$ is between 150-160. In another embodiment, $n_1$ is between 160-170. In another embodiment, $n_1$ is between 170-180. In another embodiment, $n_1$ is between 180-190. In another embodiment, $n_1$ is between 190-200.

In one embodiment, $n_2$ of structures (1) to (3) is between 0-200. In another embodiment, $n_2$ is between 0-10. In another embodiment, $n_2$ is between 10-20. In another embodiment, $n_2$ is between 20-30. In another embodiment, $n_2$ is between 30-40.

In another embodiment, $n_2$ is between 40-50. In another embodiment, $n_2$ is between 50-60. In another embodiment, $n_2$ is between 60-70. In another embodiment, $n_2$ is between 70-80. In another embodiment, $n_2$ is between 80-90. In another embodiment, $n_2$ is between 90-100. In another embodiment, $n_2$ is between 100-110. In another embodiment, $n_2$ is between 110-120. In another embodiment, $n_2$ is between 120-130. In another embodiment, $n_2$ is between 130-140. In another embodiment, $n_2$ is between 140-150. In another embodiment, $n_2$ is between 150-160. In another embodiment, $n_2$ is between 160-170. In another embodiment, $n_2$ is between 170-180. In another embodiment, $n_2$ is between 180-190. In another embodiment, $n_2$ is between 190-200.

In one embodiment, m of structures (1) to (3) is between 1-200. In another embodiment, m is between 1-10. In another embodiment, m is between 10-20. In another embodiment, m is between 20-30. In another embodiment, m is between 30-40. In another embodiment, m is between 40-50. In another embodiment, m is between 50-60. In another embodiment, m is between 60-70. In another embodiment, m is between 70-80. In another embodiment, m is between 80-90. In another embodiment, m is between 90-100. In another embodiment, m is between 100-110. In another embodiment, m is between 110-120. In another embodiment, m is between 120-130. In another embodiment, m is between 130-140. In another embodiment, m is between 140-150. In another embodiment, m is between 150-160. In another embodiment, m is between 160-170. In another embodiment, m is between 170-180. In another embodiment, m is between 180-190. In another embodiment, m is between 190-200.

In one embodiment, the anti-microbial active group of this invention may be selected from: (a) a tertiary amine (i.e. $R_3$ and/or $R_3'$ is nothing) or tertiary ammonium (i.e. $R_3$ and/or $R_3'$ is hydrogen) comprising at least one terpenoid moiety (b) a quaternary ammonium group comprising at least one terpenoid moiety (c) a quaternary ammonium group, comprising at least one alkyl group having from 4 to 24 carbon atoms; and (d) a tertiary amine (i.e. $R_3$ and/or $R_3'$ is nothing) or tertiary ammonium (i.e. $R_3$ and/or $R_3'$ is hydrogen) comprising at least one alkyl group having from 4 to 24 carbon atoms. Each possibility represents a separate embodiment of the invention.

In one embodiment, the particles of this invention represented by structures (1)-(3) comprise a polymeric or oligomeric anti-microbial active group and an inert core, wherein the polymeric or oligomeric anti-microbial active group and the core are linked indirectly.

In some embodiments $L_1$, $L_2$ or $L_3$ is each independently the same or a different linker. In some embodiments, $L_1$, $L_2$ and $L_3$ are connected to each other, in any possible way. In some embodiment, $L_3$ is nothing and $L_1$ or $L_2$ is connected to the core covalently. In another embodiment, $L_3$ is connected to the core covalently and $L_1$ or $L_2$ is connected to $L_3$. In another embodiment, a "linker" comprises any possible chemical moiety capable of connecting at least two other chemical moieties which are adjacent to such linker. In another embodiment, the polymeric or oligomeric anti-microbial active group and the core are linked to the core via the third linker ($L_3$). In another embodiment, the monomeric unit of the polymeric or oligomeric group comprises a first linker ($L_1$) and an anti-microbial group. In another embodiment, the first linker ($L_1$), and/or second linker ($L_2$) are the backbone of the polymeric/oligomeric group. In some embodiments, the linker comprises a functional group. In another embodiment, the linker comprises two (same or different) functional groups. In another embodiment, the functional group comprises phosphate, phosphonate, carboxyl, siloxane, silane, ether acetal, amide, amine, anhydride, ester, ketone, or aromatic ring or rings functionalized with any of the preceding moieties. Each possibility represents a separate embodiment of this invention.

In some embodiments, the first second or third linkers ($L_1$, $L_2$ or $L_3$) are independently a C1 to C18 alkylene, alkenylene, alkynelene, arylene or conjugated alkylene. In other embodiments the linkers are substituted with one or more functional groups including phosphate, phosphonate, carboxyl, siloxane, silane, ether acetal, amide, amine, anhydride, ester, ketone, or aromatic ring.

In other embodiments, the linker ($L_1$, $L_2$ or $L_3$) is a $C_1$ to $C_{18}$ alkylene, alkenylene, alkynelene, arylene or conjugated alkylene, substituted with at least one carboxyl moiety, wherein the carboxyl end is attached to the core. This linker may be derived from a C1 to C18 alkylene, alkenylene, alkynelene, arylene or conjugated alkylene substituted with at least one carboxyl moiety and having an amino end which is modified to antibacterial active group [—$^+N(R_1)(R_2)(R_3)$, —$^+NH(R_1)(R_2)$, —$N(R_1)(R_2)$—$^+N(R_1')(R_2')(R_3')$, —$^+NH(R_1')(R_2')$ or —$N(R_1')(R_2')$ (defined in structures (1) to (3))]. This linker may be derived from an amino acid of natural or synthetic source having a chain length of between 2 and 18 carbon atoms (polypeptide), or an acyl halide of said amino acid. Non-limiting examples for such amino acids are 18-amino octadecanoic acid and 18-amino stearic acid. In another embodiment, the linker ($L_1$, $L_2$ or $L_3$) is a Cl to C18 alkylene substituted with at least one amine or amide moiety.

In other embodiments, the linker ($L_1$, $L_2$ or $L_3$) is alkylene, alkenylene, alkynelene, arylene or conjugated alkylene, derived from a di-halo alkylene, alkenylene, alkynelene, arylene or conjugated alkylene, which is functionalized at each end with the core and anti-microbial active group, respectively, by replacement of the halogen moiety to a functional group that will bind to the core and replacement of the halogen moiety to obtain [—$^+N(R_1)(R_2)(R_3)$, —$^+NH$ $(R_1)(R_2)$, $-N(R_1)(R_2)-^+N(R_1')(R_2')(R_3')$, $-^+NH(R_1')(R_2')$ or $-N(R_1')(R_2')$ (defined in structures (1) to (3))]

In other embodiments, the linker ($L_1$, $L_2$ or $L_3$) is an arylene derived from non-limiting examples of 4,4-biphenol, dibenzoic acid, dibenzoic halides, dibenzoic sulphonates, terephthalic acid, tetrphthalic halides, and terephthalic sulphonates. This linker is functionalized with the core and anti-microbial active group, respectively, through the functional group thereof (i.e., hydroxyl, carboxy or sulfonate). In another embodiment, this linker is directly attached to the core at one end or indirectly, via a third linker ($L_3$) and is modified at the other end to anti-microbial active group $[-^+N(R_1)(R_2)(R_3)$, $-^+NH(R_1)(R_2)$, $-N(R_1)(R_2)$ $-^+N(R_1')(R_2')(R_3')$, $-^+NH(R_1')(R_2')$ or $-N(R_1')(R_2')$ (defined in structures (1) to (3))].

In another embodiment, $L_1$, $L_2$, $L_3$ or any combination thereof, is a siloxane or silane group derived and/or selected from non-limiting examples of trialkoxyalkylsilane, trialkoxyarylsilane, trihaloalkylsilane, trihaloarylsilane, 3-aminopropyltriethoxysilane (APTES) and N-2-aminoethyl-3-aminopropyl trimethoxysilane.

In another embodiment, the third linker ($L_3$) is linked to the core and to the anti-microbial active group, respectively, via the functional group thereof (i.e., hydroxyl, siloxane, carboxy, amide or sulfonate). In another embodiment, the first ($L_1$) and/or second linkers (L2) is directly attached to the core at one end or indirectly, via a third linker ($L_3$) and is modified at the other end to anti-microbial active group $[-^+N(R_1)(R_2)(R_3)$, $-^+NH(R_1)(R_2)$, $-N(R_1)(R_2)$ $-^+N(R_1')(R_2')(R_3')$, $-^+NH(R_1')(R_2')$ or $-N(R_1')(R_2')$ (defined in structures (1) to (3))].

In another embodiment, a monomeric unit within the polymeric/oligomeric anti-microbial active unit is represented by the structure of formula IA:

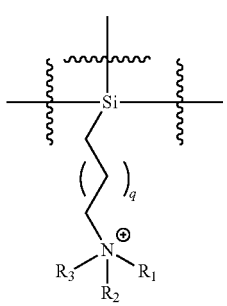

(IA)

wherein $R_1$ and $R_2$ are independently linear or branched alkyl, terpenoid, cycloalkyl, aryl, heteroaryl, alkenyl, alkynyl or any combination thereof; and $R_3$ is nothing, linear or branched alkyl, terpenoid, cycloalkyl, aryl, heteroaryl, alkenyl, alkynyl or any combination thereof; wherein if $R_3$ is nothing, the nitrogen is not charged;

q is an integer between 0 and 16;

wherein said monomeric unit is chemically bound to the surface of an inorganic core directly or via a third linker ($L_3$).

In another embodiment, a monomeric unit within the polymeric/oligomeric anti-microbial active unit is represented by the structure of formula IB:

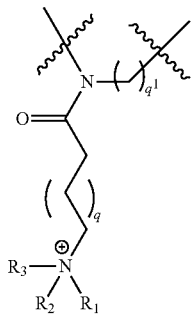

(IB)

wherein $R_1$ and $R_2$ are independently linear or branched alkyl, terpenoid, cycloalkyl, aryl, heteroaryl, alkenyl, alkynyl or any combination thereof; and $R_3$ is not present, linear or branched alkyl, terpenoid, cycloalkyl, aryl, heteroaryl, alkenyl, alkynyl or any combination thereof; wherein if $R_3$ is not present, the nitrogen is not charged;

q and $q^1$ are independently an integer between 0 and 16;

wherein said monomeric unit is chemically bound to the surface of an inorganic core directly or via a third linker ($L_3$).

The particles of this invention demonstrate an enhanced anti-bacterial activity. Without being bound by any theory or mechanism, it can be postulated that such activity originates from the presence of closely packed anti-bacterial groups on a given core's surface, as well as high density of particles packed on the surface of a host matrix. This density increases as each polymeric or oligomeric anti-microbial active unit in the particles of this invention comprise increasing number of anti-microbial active groups and it yields a high local concentration of active functional groups, which results in high effective concentration of the antibacterial active groups and enables the use of a relatively small amount of particles to achieve effective bacterial annihilation. The close packing of the antibacterial groups is due to at least two main features of this invention:

numerous oligomeric or polymeric anti-microbial active units protruding from each particle surface; and at least two anti-microbial groups per each such oligomeric or polymeric unit.

Accordingly, the anti-bacterial groups cover large fraction of the particle's available surface area (width dimension covering the surface) and further—each particle has on its surface more than one layer of antibacterial groups (height dimension on top of the surface). The surface density of the anti-microbial group results in high effective concentration promoting anti-bacterial inhibitory effect. According to the principles of this invention, high surface density dictates high anti-microbial efficiency.

The term "nanoparticle" as used herein refers to a particle having a diameter of less than about 1,000 nm. The term "microparticle" as used herein refers to a particle having a diameter of about 1,000 nm or larger.

The particles of this invention are characterized by having a diameter between about 5 to about 100,000 nm, and thus encompass both nanoparticulate and microparticulate compositions. Preferred are particles between about 10 to about 50,000 nm. In other embodiments, the particles are more than 1,000 nm in diameter. In other embodiments, the particles are more than 10,000 nm in diameter. In other embodiment, the particles are between 1,000 and 50,000 nm in diameter. In other embodiment, the particles are between 5 and 250 nm in diameter. In other embodiment, the particles are between 5 and 500 nm in diameter. In another embodiment, the particles are between 5 and 1000 nm in diameter. It is apparent to a person of skill in the art that other particles size ranges are applicable and are encompassed within the scope of this invention.

Anti-Microbial Active Groups Comprising Terpenoid Groups

In one embodiment, the anti-microbial active group of this invention contains at least one terpenoid group, and is selected from: (a) a tertiary amine ($R_3$ and/or $R_3'$ is nothing) or tertiary ammonium ($R_3$ and/or $R_3'$ is H) comprising at least one terpenoid moiety; and (b) a quaternary ammonium group comprising at least one terpenoid moiety.

In some embodiments, the anti-microbial active group of formula (1) to (3) is selected from: (a) a tertiary amine ($R_3$ and/or $R_3'$ is nothing) or tertiary ammonium ($R_3$ and/or $R_3'$ is H), wherein the nitrogen atom of each tertiary amine/ammonium having at least one bond to $X_1$ or $X_2$ and one bond to a terpenoid moiety;(b) a tertiary amine ($R_3$ and/or $R_3'$ is nothing), or tertiary ammonium ($R_3$ and/or $R_3'$ is H), the nitrogen atom of each tertiary amine/ammonium having one bond to $X_1$ or $X_2$ and two bonds to terpenoid moieties which may be the same or different from each other, or a salt of said tertiary amine; (c) a quaternary ammonium group the nitrogen atom of each quaternary ammonium group having at least one bond to $X_1$ or $X_2$ and one or two bonds to terpenoid moieties which may be the same or different from each other; Each possibility represents a separate embodiment of this invention.

The term "terpenoid", also known as "isoprenoid" refers to a large class of naturally occurring compounds that are derived from five-carbon isoprene units.

In one embodiment, the at least one terpenoid moiety is a cinammyl group derived from cinnamaldehyde, cinnamic acid, curcumin, viscidone or cinnamyl alcohol. In another embodiment, the at least one terpenoid moiety is a bornyl group derived from camphor, bornyl halide or bornyl alcohol. In another embodiment, the at least one terpenoid moiety is derived from citral. In another embodiment, the at least one terpenoid moiety is derived from perilaldehyde. Each possibility represents a separate embodiment of this invention.

Cinnamaldehyde is a natural aldehyde extracted from the genus *Cinnamomum*. It is known for its low toxicity and its effectiveness against various bacteria and fungi.

Camphor is found in the wood of the camphor laurel (*Cinnamomum camphora*), and also of the kapur tree. It also occurs in some other related trees in the laurel family, for example *Ocotea usambarensis*, as well as other natural sources. Camphor can also be synthetically produced from oil of turpentine. Camphor can be found as an R or S enantiomer, a mixture of enantiomers and a racemic mixture. Each possibility represents a separate embodiment of this invention.

Citral, or 3,7-dimethyl-2,6-octadienal or lemonal, is a mixture of two diastereomeric terpenoids. The two compounds are double bond isomers. The E-isomer is known as geranial or citral A. The Z-isomer is known as neral or citral B. Citral is known to have anti-bacterial activity.

Perillaldehyde, also known as perilla aldehyde, is a natural terpenoid found most in the annual herb perilla, as well as in a wide variety of other plants and essential oils.

Other examples of terpenoids include, but are not limited to: curcuminoids found in turmeric and mustard seed, and citronellal found in Cymbopogon (lemon grass) and carvacrol, found in *Origanum vulgare* (oregano), thyme, pepperwort, wild bergamot and Lippia graveolens. Each possibility represents a separate embodiment of this invention.

In accordance with the above embodiment, the anti-microbial active terpenoid moieties are selected from the group consisting of:

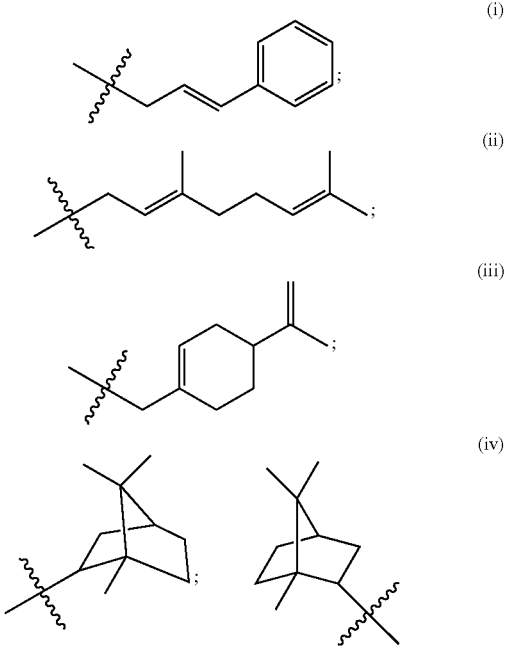

or any combination thereof;

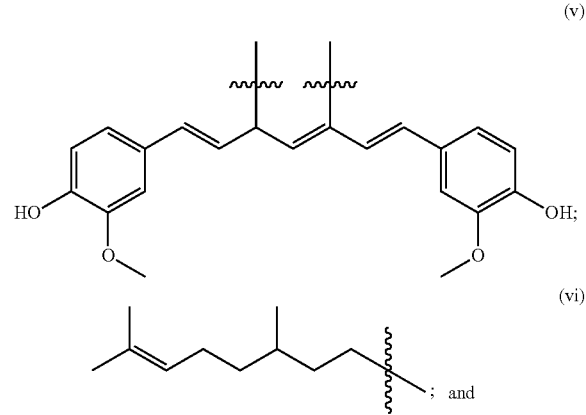

Each possibility represents a separate embodiment of this invention.

Non-limiting examples of functional anti-microbial active tertiary amine groups or its protonated form in accordance with the principles of this invention are:

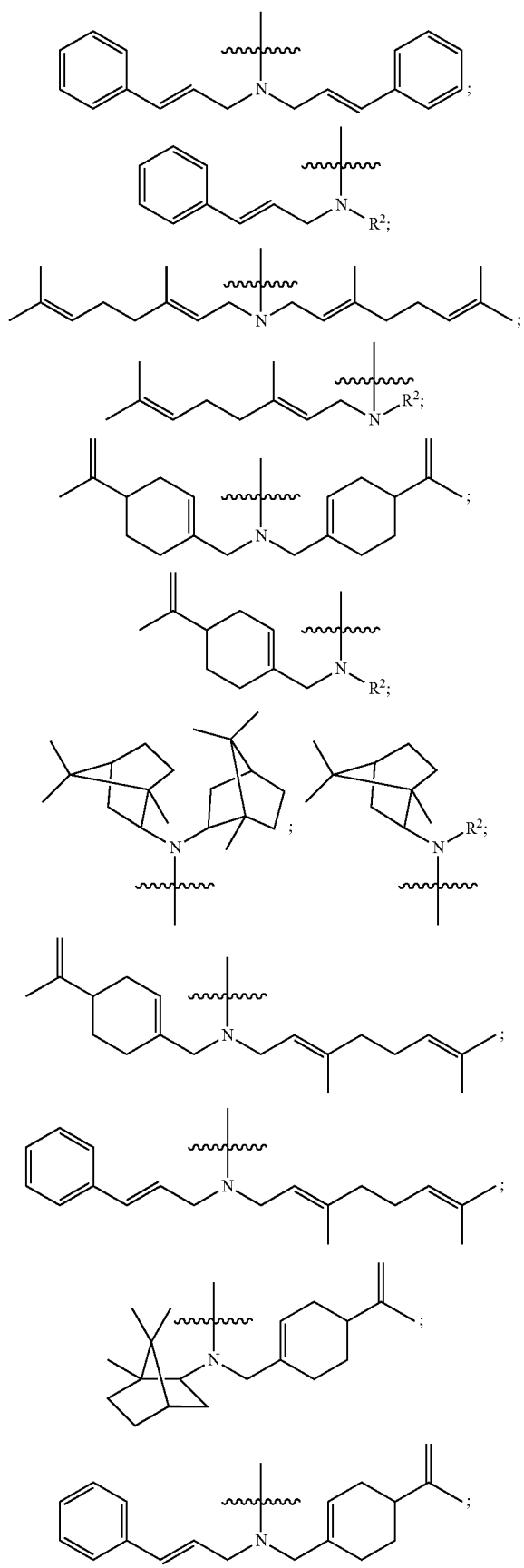
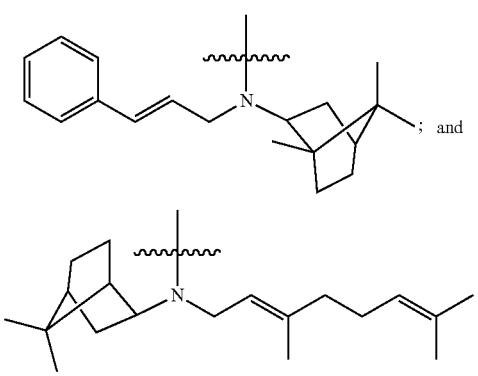
wherein R² is alkyl, terpenoid, cycloalkyl, aryl, heterocycle, alkenyl, alkynyl or any combination thereof.
Non-limiting examples of anti-microbial active quaternary ammonium groups in accordance with the principles of this invention are:
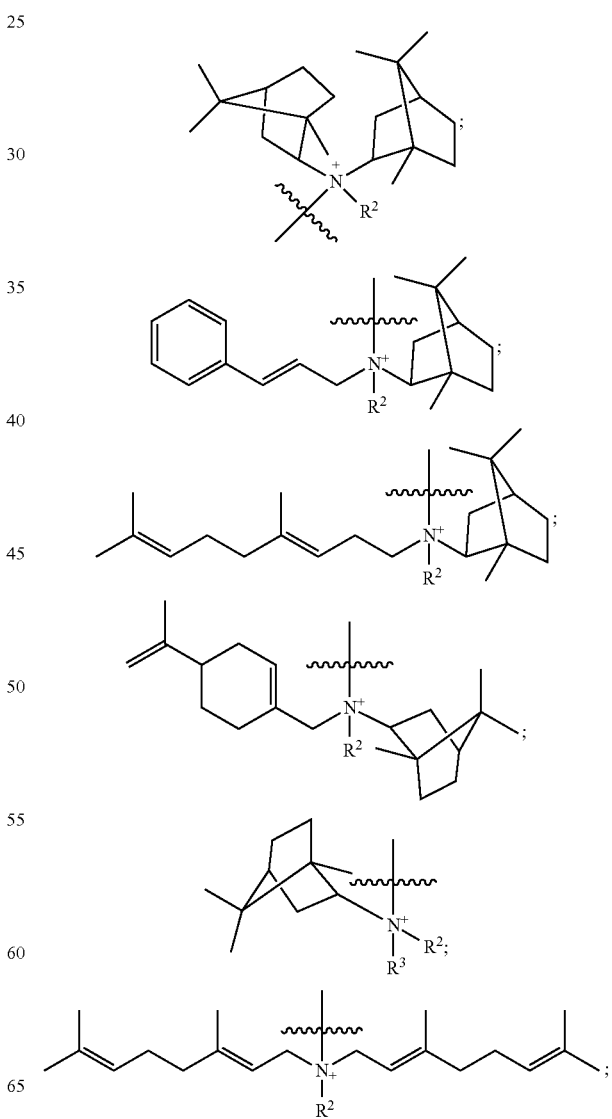

-continued

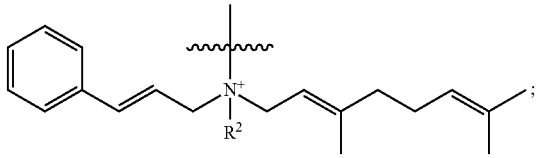

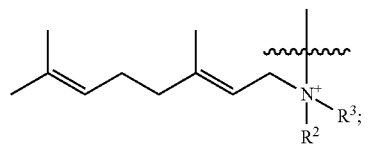

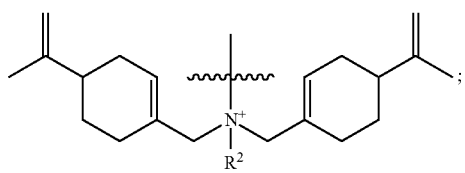

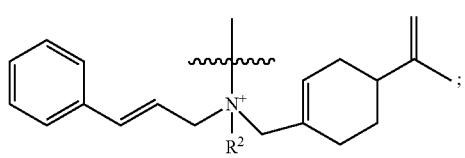

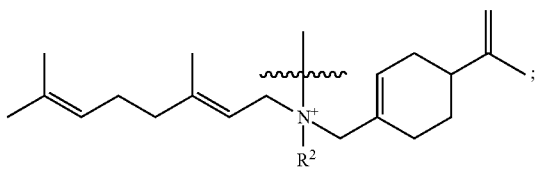

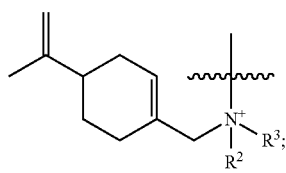

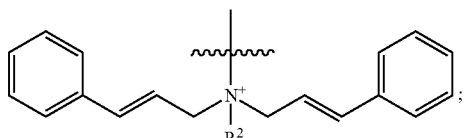

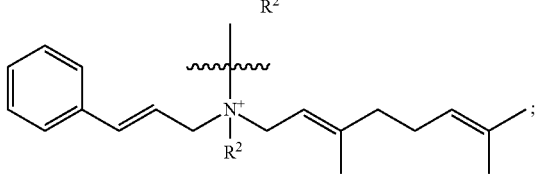

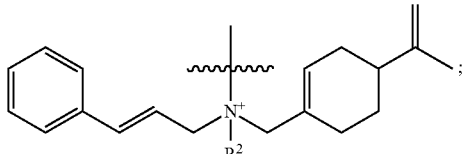

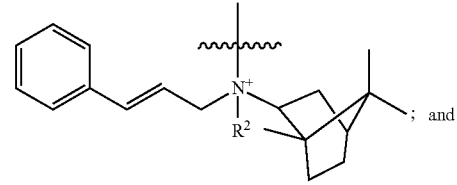
; and

-continued

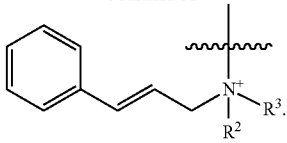

wherein $R^2$ is alkyl, terpenoid, cycloalkyl, aryl, heterocycle, a conjugated alkyl, alkenyl, alkynyl or any combination thereof;

$R^3$ is nothing, alkyl, terpenoid moiety, cycloalkyl, aryl, heterocycle, a conjugated alkyl, alkenyl, alkynyl or any combination thereof; wherein if $R^3$ is nothing, the nitrogen is not charged.

The anti-microbial active group of this invention may be in the form of a tertiary amine, or in the form of a protonated said tertiary amine, or in the form of a quaternary ammonium salt, as described hereinabove. Since an ammonium group is positively charged, its charge is balanced with an anion. Preferably, in a particle according to the invention this anion is a halide, e.g. fluoride, chloride, bromide or iodide, and fluoride is most preferred. Other possible anions include, but are not limited to, bicarbonate, nitrate, phosphate, acetate, fumarate, succinate and sulfate. Each possibility represents a separate embodiment of this invention.

Anti-Microbial Active Groups Comprising One Long Alkyl Group.

In accordance with another embodiment, the anti-microbial active group of this invention [—$^+N(R_1)(R_2)(R_3)$, —$^+NH(R_1)(R_2)$, —$N(R_1)(R_2)$ —$^+N(R_1')(R_2')(R_3')$, —$^+NH(R_1')(R_2')$ or —$N(R_1')(R_2')$ (defined in structures (1) to (3))] is a quaternary ammonium group, a tertiary amine or a tertiary ammonium, the nitrogen atom of each amine/ammonium group having at least one bond $X_1$ or $X_2$, at least one bond to an alkyl group having from 4 to 24 carbon atoms ($R_1$ and/or $R_1'$). In another embodiment, the nitrogen atom of each amine/ammonium group having one bond to the core, one bond to an alkyl group having from 4 to 24 carbon atoms ($R_1$ and/or $R_1'$).

Since an ammonium group is positively charged, its charge should be balanced with an anion. Any of the counter-ions described above may be used to counter-balance the quaternary ammonium group.

In some embodiments, the nitrogen atom of each quaternary ammonium or tertiary ammonium group has (i) at least one bond to $X_1$ or $X_2$; and (ii) at least one bond to the alkyl group having from 4 to 24 carbon atoms.

In some embodiments, the anti-microbial active group of formula (1) to (3) is selected from: (a) a tertiary amine ($R_3$ and/or $R_3'$ is nothing) or tertiary ammonium ($R_3$ and/or $R_3'$ is H), wherein the nitrogen atom of each tertiary amine/ammonium having at least one bond to $X_1$ or $X_2$ and one bond to the alkyl group having from 4 to 24 carbon atoms; (b) a tertiary amine ($R_3$ and/or $R_3'$ is nothing), or tertiary ammonium ($R_3$ and/or $R_3'$ is H), wherein the nitrogen atom of each tertiary amine/ammonium having one bond to $X_1$ or $X_2$ and two bonds to alkyl groups having from 4 to 24 carbon atoms which may be the same or different from each other, or a salt of said tertiary amine; (c) a quaternary ammonium group wherein the nitrogen atom of each quaternary ammonium group having at least one bond to $X_1$ or $X_2$ and one or two bonds to the alkyl groups having from 4 to 24 carbon atoms which may be the same or different from each other. Each possibility represents a separate embodiment of this invention.

The term "quaternary ammonium group" refers to a group of atoms consisting of a nitrogen atom with four substituents (different than hydrogen) attached thereto. In another embodiment, a "quaternary ammonium group" refers to a group of atoms consisting of a nitrogen atom with four groups wherein each of the group is attached to the nitrogen through a carbon atom. The term "long alkyl group" or chain refers to such an alkyl group or chain which is substituted on the nitrogen atom of the quaternary ammonium group and which has between 4 and 24 carbon atoms. In some currently preferred embodiments, the alkyl group is an alkyl group having 4 to 18 carbon atoms. In some currently preferred embodiments, the alkyl group is an alkyl group having 4 to 8 carbon atoms. In some currently preferred embodiments, the alkyl group is an alkyl group having 4 to 10 carbon atoms. In other currently preferred embodiments, the alkyl group is an alkyl group having 6, 7, or 8 carbon atoms, with each possibility representing a separate embodiment of this invention.

Organic polymeric Cores

In some embodiments, the core of the particles is an organic polymeric core. In one embodiment, the organic core comprises at least one aliphatic polymer. An "aliphatic polymer" as used within the scope of this invention refers to a polymer made of aliphatic monomers that may be substituted with various side groups, including (but not restricted to) aromatic side groups. Aliphatic polymers that may be included in particles according to this invention comprise nitrogen atoms (as well as other heteroatoms) as part of the polymeric backbone. In one embodiment, the core of the particles is an organic polymeric core including an amine which can be substituted with $R_1$, $R_2$ and/or $R_3$ as defined for the structure of formula 1; or including an imine which is chemically modified to amine and then substituted with $R_1$, $R_2$ and/or $R_3$ as defined for the structure of formula 1. Non-limiting examples of aliphatic polymers are polystyrene (PS), polyvinylchloride (PVC), polyethylene imine (PEI), polyvinyl amine (PVA), poly(allyl amine) (PAA), poly(aminoethyl acrylate), polypeptides with pending alkylamino groups, and chitosan. Each possibility represents a separate embodiment of this invention. In one currently preferred embodiment, the polymer is polyethylene imine (PEI).

In another embodiment, the organic core comprises at least one aromatic polymer selected from the following group: polystyrene, aminomethylated styrene polymers, aromatic polyesters, preferably polyethylene terephthalate, and polyvinyl pyridine.

The polymeric core may be linked to the oligomeric or polymeric anti-microbial active group directly (i.e. in formulas (1)-(3): $L_3$ is a bond) or via a linker. Each possibility represents a separate embodiment of this invention.

In one embodiment, the organic polymeric core includes a combination of two or more different organic polymers. In another embodiment, the organic polymeric core includes a copolymer.

In some embodiments, polymeric/oligomeric group is linked to the organic polymeric core directly ($L_3$ is a bond) or via a linker ($L_3$). In these embodiments, the linker may be selected from:
(a) a C1 to C18 alkylene substituted with at least one carboxyl moiety. This linker may be derived from an alkylene substituted with at least one carboxyl moiety and at least one amino moiety, wherein the carboxyl end is attached to the core and the amino end is modified to antibacterial active group [—$^+$N($R_1$)($R_2$)($R_3$), —$^+$NH($R_1$)($R_2$), —N($R_1$)($R_2$)—$^+$N($R_1$')($R_2$')($R_3$'), —$^+$NH($R_1$')($R_2$') or —N($R_1$')($R_2$') (defined in structures (1) to (3))] This linker may be derived from an amino acid of natural or synthetic source having a chain length of between 2 and 18 carbon atoms, or an acyl halide of said amino acid. Non-limiting examples for such amino acids are 18-amino octadecanoic acid and 18-amino stearic acid;
(b) a C1 to C18 alkylene. This linker may be derived from a di-halo alkylene, which is functionalized at each end with the core and anti-microbial active group, respectively, by replacement of the halogen moiety to a functional group that will bind to the core and replacement of the halogen moiety to obtain [—$^+$N($R_1$)($R_2$)($R_3$), —$^+$NH($R_1$)($R_2$), —N($R_1$)($R_2$)—$^+$N($R_1$')($R_2$')($R_3$'),—$^+$NH($R_1$')($R_2$') or —N($R_1$')($R_2$') (defined in structures (1) to (3))]; and
(c) an arylene. This linker may be. derived from 4,4-biphenol, dibenzoic acid, dibenzoic halides, dibenzoic sulphonates, terephthalic acid, tetrphthalic halides, and terephthalic sulphonates. This linker is functionalized with the core and anti-microbial active group, respectively, through the functional group thereof (i.e., hydroxyl, carboxy or sulfonate). In another embodiment, this linker is attached to the core at one end and is modified at the other end to anti-microbial active group [—$^+$N($R_1$)($R_2$)($R_3$), —$^+$NH($R_1$)($R_2$), —N($R_1$)($R_2$)—$^+$N($R_1$')($R_2$')($R_3$'),—$^+$NH($R_1$')($R_2$') or —N($R_1$')($R_2$') (defined in structures (1) to (3))] In another embodiment, the linker comprises functional groups such as alkyl, alkenyl, alkyl phosphate, alkyl siloxanes, carboxylate, epoxy, acylhalides, anhydrides, or combination thereof, wherein the functional group is attached to the core. Each possibility represents a separate embodiment of this invention.

Various polymeric chains may provide a range of properties that themselves may be an accumulation of the various polymer properties, and may even provide unexpected synergistic properties. Examples of such mixed polyamine particles include: crosslinking of aliphatic and aromatic polyamines such as polyethyleneimine and poly(4-vinyl pyridine) via a dihaloalkane; mixture of linear short chain and branched high molecular weight polyethyleneimines; interpenetrating compositions of polyamine within a polyamine scaffold such as polyethyleneimine embedded within crosslinked polyvinyl pyridine particles, or even interpenetrating a polyamine into a low density non-amine scaffold such as polystyrene particles. In other words, the use of polyamine combinations for the purpose of forming particles, either by chemical crosslinking or physical crosslinking (interpenetrating networks) may afford structures of varying properties (such as being able to better kill one bacteria vs. another type of bacteria). Such properties may be additive or synergistic in nature.

In one specific embodiment, the organic polymeric core is cross-linked with a cross-linking agent. The preferred degree of cross-linking is from 1% to 20%, when crosslinking of from about 2% to about 5% is preferable. The crosslinking may prevent unfolding of the polymer and separation of the various polymeric chains that form the particle.

Crosslinking, as may be known to a person skilled in the art of organic synthesis and polymer science, may be affected by various agents and reactions that are per se known in the art. For example, crosslinking may be affected by alkylating the polymer chains with dihaloalkane such as dibromoethane, dibromocyclohexane, or bis-bromomethylbenzene. Alternatively, crosslinking by reductive amination may be used. In this method a polyamine with primary amines is reacted with a diketone or with an alkane dialdehyde to form an imine crosslinker which is then farther hydrogenated to the corresponding amine This amine may be further reacted to form an antimicrobial effective quaternary ammonium group. In such a method, instead of dihaloalkanes or dialdehydes one may use a tri or polyhaloalkanes or polyaldehydes or polyketones.

The preferred polymers useful for making particles according to the invention are those having chains made of 30 monomer units, preferably 100 monomer units that may be crosslinked using less than 10% of crosslinking agent. The longer the polymers are, the fewer crosslinking bonds are needed to afford an insoluble particle. Branched polymers are preferred for crosslinking as small amount of crosslinking is required to form insoluble particles.

In some embodiments, at least about 10% of the amine groups in the organic polymeric core are derivatized to an anti-microbial active tertiary amine/ammonium or quaternary ammonium groups or salts thereof, as described herein.

In a preferred embodiment, the particles according to the invention have functional groups that are capable of reacting with a host polymer or with monomers thereof. Such functional groups are designed to allow the particles to be bound chemically to a hosting matrix.

Inorganic Cores

In some embodiments, the core of the particles of this invention is an inorganic core comprising one or more inorganic materials. Inorganic cores have a few advantages over organic polymeric cores: 1) higher stability at elevated temperature; 2) higher chemical stability towards various solvent and reagents; 3) improved mechanical strength; 4) better handling qualities in matrices due to their amphipathic nature; and 5) lower cost.

An additional advantage of inorganic cores relates to the insertion of the functionalized particles into a polymeric matrix. In the case where matrix polymerization involves radical polymerization (e.g. acrylate resins), inorganic cores do not interfere with the polymerization process and hence do not jeopardize the mechanical properties of the finalized substrate, as opposed to organic polymeric cores which tend to interfere with the polymerization reaction.

In one embodiment, the inorganic core comprises silica, metal, metal oxide or a zeolite. Each possibility represents a separate embodiment of this invention.

In one embodiment, the core of the particles of this invention comprises silica ($SiO_2$). The silica may be in any form known in the art, non-limiting examples of which include polyhedral oligomeric silsesquioxane (POSS), amorphous silica, dense silica, aerogel silica, porous silica, mesoporous silica and fumed silica.

The surface density of active groups onto particle surface have proportional impact on its antibacterial activity. This is applicable both to organic and inorganic particles in same manner In another embodiment, the core of the particles of this invention comprises glasses or ceramics of silicate ($SiO_4^{-4}$). Non-limiting examples of silicates include aluminosilicate, borosilicate, barium silicate, barium borosilicate and strontium borosilicate.

In another embodiment, the core of the particles of this invention comprises surface activated metals selected from the group of: silver, gold, platinum, palladium, copper, zinc and iron.

In another embodiment, the core of the particles of this invention comprises metal oxides selected from the group of: zirconium dioxide, titanium dioxide, vanadium dioxide, zinc oxide, copper oxide and magnetite.

The inorganic core typically has a solid uniform morphology with low porosity or a porous morphology having pore size diameter of between about 1 to about 30 nm.

In another embodiment, the core of the particles of this invention comprises natural or artificial Zeolites.

In one embodiment, the core may be attached to the polymeric/oligomeric group directly (i.e. in formulas (1)-(3): $L_3$ is a bond), or via a linker ($L_3$). Preferably a silica ($SiO_2$) based inorganic core may be attached to the polymeric/oligomeric group through a linker (L3), while glasses or ceramicas of silicate ($SiO_4^{-4}$), metals or metal oxides may be attached to the polymeric/oligomeric group directly (i.e. in formulas (1)-(3): $L_3$ is a bond).

In some embodiments, the inorganic core is directly (i.e. in formulas (1)-(3): $L_3$ is a bond) attached to the oligomeric/polymeric group. In other embodiments, the inorganic core is attached to the oligomeric/polymeric group through a linker. In some embodiments, the linker is selected from the following groups: a C1 to C18 alkylene; a C1 to C18 alkylene substituted with at least one silane or alkoxysliane moiety; a C1 to C18 alkylene substituted with at least one phosphate moiety; a C1 to C18 alkylene substituted with at least one anhydride moiety; a C1 to C18 alkylene substituted with at least one carboxylate moiety; and a C1 to C18 alkylene substituted with at least one glycidyl moiety. Each possibility represents a separate embodiment of this invention.

The inorganic core of the particle as described above may generally be in a form selected from a sphere, amorphous polygonal, shallow flake-like and a rod. In some representative embodiments, the inorganic core is spherical and has a diameter between about 5 to about 100,000 nm. In some representative embodiments, the inorganic core is spherical and has a diameter between about 1000-100,000 nm. In some representative embodiments, the inorganic core is spherical and has a diameter between about 100-1000 nm with pore diameter of about 1 to about 100 nm. In another embodiment, the inorganic spherical core has a pore diameter of about 1 to about 50 nm. In another embodiment, the inorganic spherical core has a pore diameter of about 1 to about 30 nm. In another embodiment, the inorganic particle is in a form of a rod, having a diameter of between about 5 to about 1,000 nm and length between about 10 to about 1,000,000 nm. In another embodiment, a length of between 50 to 100,000 nm. In another embodiment, a length of between 100 to 250,000 nm. In another embodiment, a length of between 200 to 500,000 and a pore diameter of about 1 to about 50 nm. Each possibility represents a separate embodiment of this invention.

Preparation of Particles

In some embodiments, the particles of this invention are prepared in accordance with a variety of processes, depending on the nature of the core, the anti-microbial active group/part, and the presence or absence of linkers. Some non-limiting examples of preparation methods are provided below.

Preparation of the Core of the Particles

In some embodiments, porous silica materials are prepared by reaction of $SiCh_4$ with alcohol or water, followed by drying using centrifugation and/or heating utilizing airflow or under vacuum conditions. Dense fumed silica particles (pyrogenic) are prepared by pyrolysis of $SiCl_4$.

In another embodiment, silica core material is prepared by the hydrolysis of tetraethylorthosilicate (TEOS) or tetramethyl orthosilicate (TMS) in the presence of alcohol or water solution and under basic (Stober) or acidic catalytic conditions.

In another embodiment, mesoporous silica particles are prepared by hydrolysis of TEOS or TMS at low temperatures, preferably in a temperature not exceeding 60° C., followed by dehydration by centrifugation and/or evaporation under airflow or vacuum conditions.

In another embodiment, dense particles are prepared utilizing intense heating in a process called calcination. Typically, such process takes place at high temperatures at about 250° C.

Figure 2A:
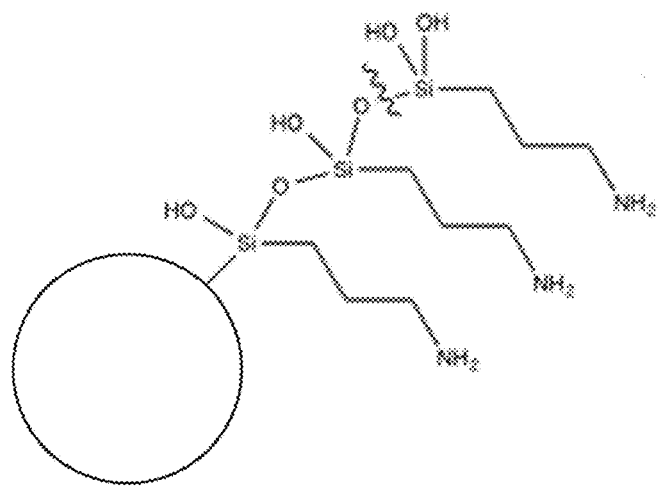
FIGS. 2A-2C depict self-polymerization of trialkoxysilane linker molecule.
Figure 2B:
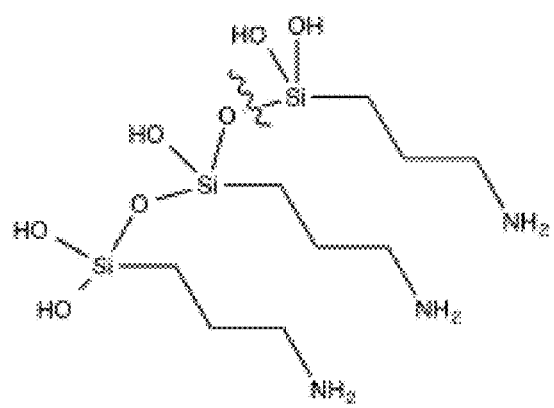

Functionalization of Core Particles (i) Methods for the Preparation of Anti-Microbial Particles Using Self-Polymerized of Silane Linker In one embodiment, silane linker is used in a high concentration (≥10%) and it initially self-polymerizes (FIGS. 2A-2B) under basic catalysis. Functionalization of the linker (usually through an amine, $NH_2$, moiety) progresses as shall be described below.

Figure 3:
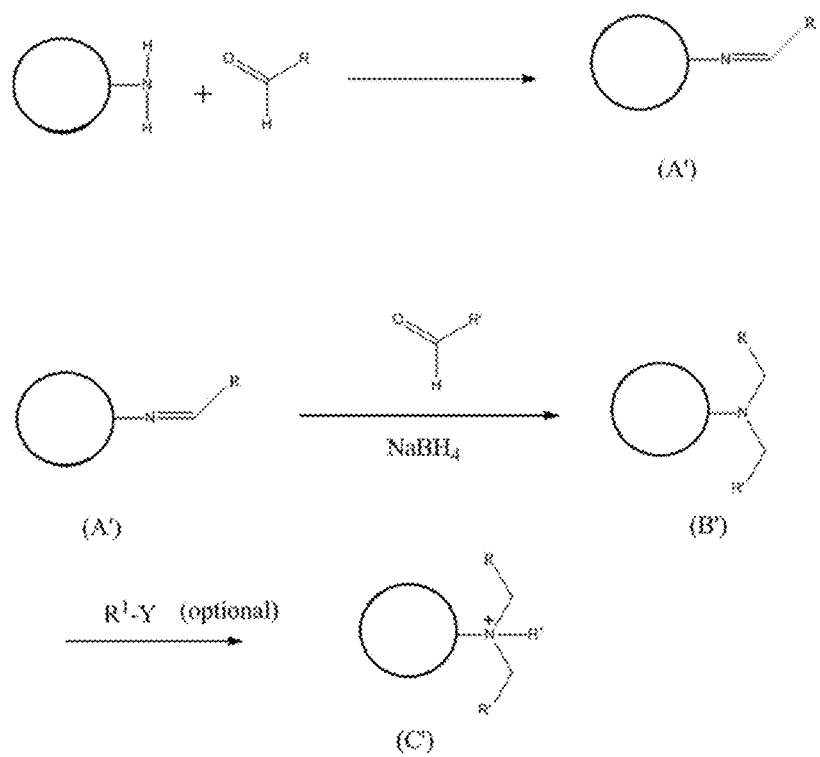
FIG. 3 depicts a representative scheme for the preparation of particles according to this invention wherein the anti-microbial active group is a tertiary amine or a quaternary ammonium group comprising at least one terpenoid moiety and the anti-microbial unit has one monomeric unit (a monomeric backbone, as presented in FIG. 1B); the circles represent the organic or inorganic core; and $R^1$—Y—$R^1$ is a $C_1$-$C_4$ alkyl and Y is a leaving group such as halogen or sulfonate.

A representative method for preparing particles with polymerized siloxane linker according to this invention, wherein the anti-microbial active group is a tertiary amine or a quaternary ammonium group comprising at least one terpenoid moiety—is represented in FIG. 3. In accordance with FIG. 3, a core as defined herein is functionalized with a primary amine The primary amine reacts with an aldehyde to yield initially an imine (Schiff base) intermediate of formula (A'), which is then reacted with a second aldehyde under reductive amination conditions to yield a tertiary amine of formula (B'). RC(=O)H and R'C(=O)H each represent an aldehyde which is a terpenoid or which is derived from a terpenoid. RC(=O)H and R'C(=O)H may be the same or different from each other. Conversion of the tertiary amine to the quaternary ammonium group (C') is optional, and involves reaction of the tertiary amine with a group $R^1$—Y wherein $R^1$ is a $C_1$-$C_4$ alkyl and Y is a leaving group such as halogen or sulfonate.

It is understood that that the group

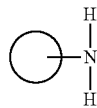

may represent any one or more of the following:
1. An organic core directly bound to $NH_2$.
2. An organic core bound to $NH_2$ through a linker as described herein.
3. An inorganic core directly bound to $NH_2$.
4. An inorganic core bound to $NH_2$ through a linker as described herein.
5. Any one of the above, wherein more than one $NH_2$ is bound as described above and more than one reacts as presented in the scheme (FIGS. 3-4).

The exemplified reaction may be a "one pot synthesis", or it may include two sequential reactions with isolation of an intermediate formed in the first step. The first step is the formation of intermediate (A'), which is an imine (Schiff base), by reacting an amine functionalized core with a terpenoid moiety in the presence of a reducing agent, in this case cinnamyl in the presence of $NaBH_4$. The imine functionalized core can be isolated at this stage if desired. Alternatively, further reacting intermediate (A') with a terpenoid moiety in the presence of a reducing agent yields a tertiary amine comprising two terpenoid moieties (B'). In order to obtain the quaternary ammonium, additional alkylation step is performed as described in FIG. 3.

Figure 4:
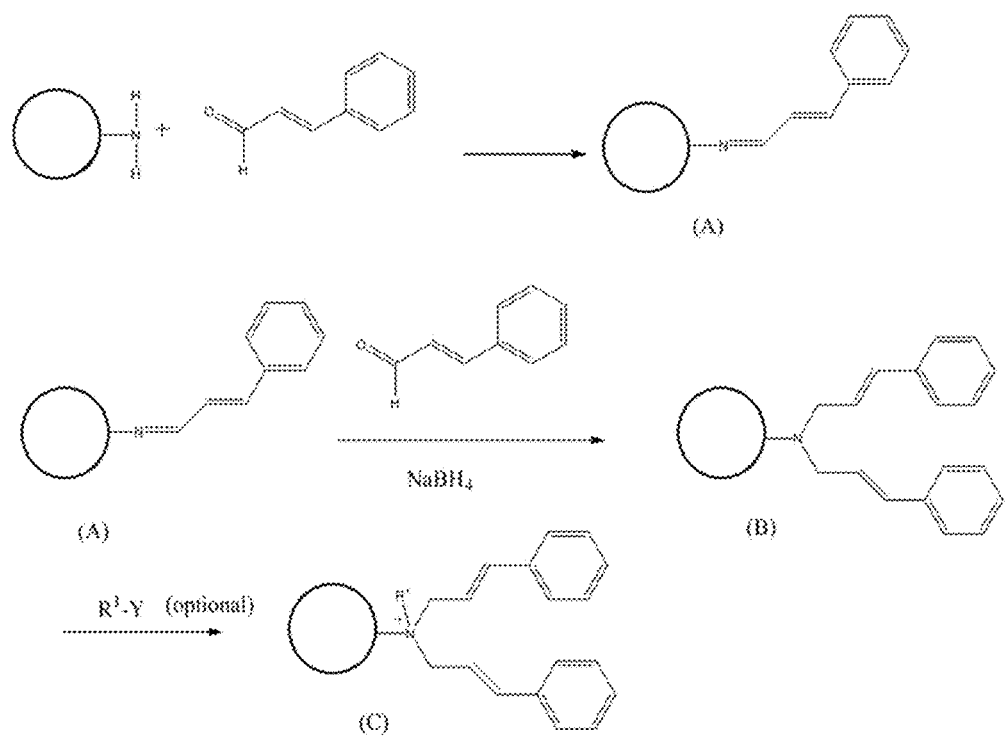
FIG. 4 depicts a representative scheme for the preparation of a particle of this invention having cinnamyl groups with a core (represented by a circle) via amino-functional linker wherein the anti-microbial unit has one monomeric unit (a monomeric backbone, as presented in FIG. 1B). Conversion of the tertiary amine to the quaternary ammonium group is optional, and involves reaction of the tertiary amine with a group $R^1$—Y wherein $R^1$ is a $C_1$-$C_4$ alkyl and Y is a leaving group such as halogen or sulfonate.

This process is exemplified in FIG. 4 for cinnamaldehyde, but is applicable to other aldehydes.

The imine particle which is an intermediate in the process for preparing the anti-microbial active particles, is new, and represents a separate embodiment of this invention. Thus, in some embodiments, this invention provides a particle comprising (i) an inorganic core or an organic polymeric core; and (ii) an imine moiety chemically bound to the core, preferably at a surface density of at least one imine group per 10 sq. nm, wherein the imine group comprises a terpenoid moiety. The imine moiety is generally represented by the structure of formula (B') in FIG. 3. A more specific embodiment is the structure of formula (B) in FIG. 4. It is understood by a person of skill in the art that other imine intermediate compounds comprising other terpenoids groups as described herein, are also encompassed by this invention.

Figure 5A:
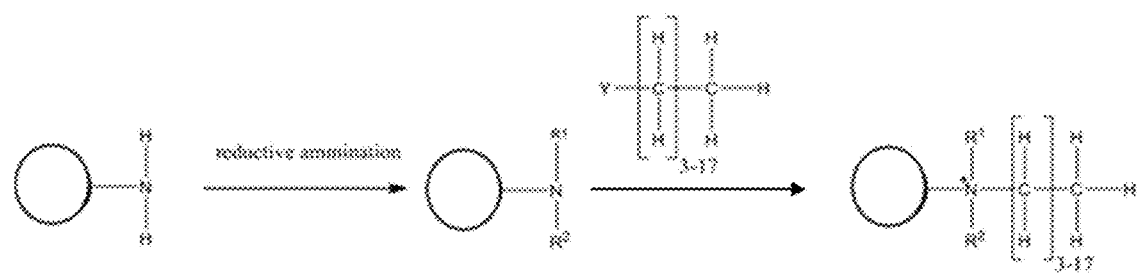
FIGS. 5A-5C: depict a representative scheme of three pathways for the preparation of quaternary ammonium salts (QAS) functionalized particle wherein the anti-microbial unit has one monomeric unit (a monomeric backbone, as presented in FIG. 1B); the circles represents organic or inorganic core.
Figure 5B:
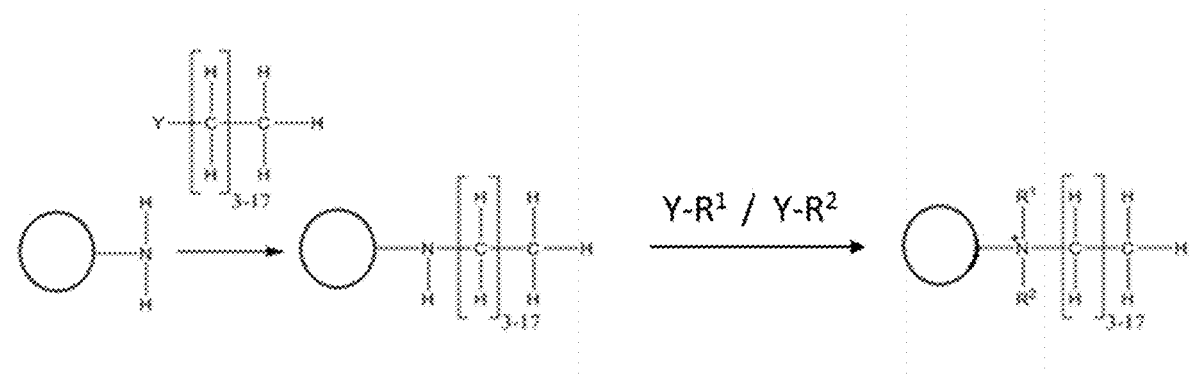
Figure 5C:
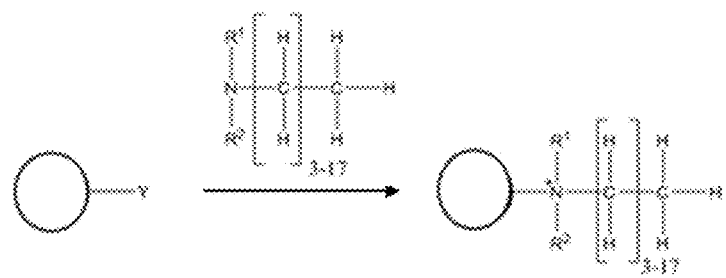

In one embodiment, a representative method for preparing particles according to this invention wherein the anti-microbial active group is a quaternary ammonium group containing one alkyl group having 4 to 18 carbon atoms is presented in FIGS. 5A-5C. The method includes three pathways to prepare quaternary ammonium salts (QAS) functionalized particle. FIG. 5A) by first utilizing reductive amination to achieve tertiary amine, followed by an alkylation reaction, FIG. 5B) by stepwise alkylation reactions; and FIG. 5C) by reacting a linker functionalized with a leaving group (e.g., Cl or other halogen) with tertiary amine $R^1$ and $R^2$ represent $C_1$-$C_3$ alkyls such as methyl, ethyl, propyl or isopropyl. $R^1$ and $R^2$ may be different or the same group. Y represents any leaving group, for example Cl, Br or I, or a sulfonate (e.g., mesyl, tosyl).

It is understood that that the group

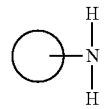

has any one of the meanings as described above for FIGS. 3 and 4.

It is understood that that the group

may represents any one or more of the following:
1. An organic core directly bound to Y.
2. An organic core bound to Y through a linker as described herein.
3. An inorganic core directly bound to Y.
4. An inorganic core bound to Y through a linker as described herein.

In some embodiments, core functionalization of self-polymerized trialkoxysilane linker is performed by a solid support method, or a solution method (FIGS. 3-7).

Figure 6:
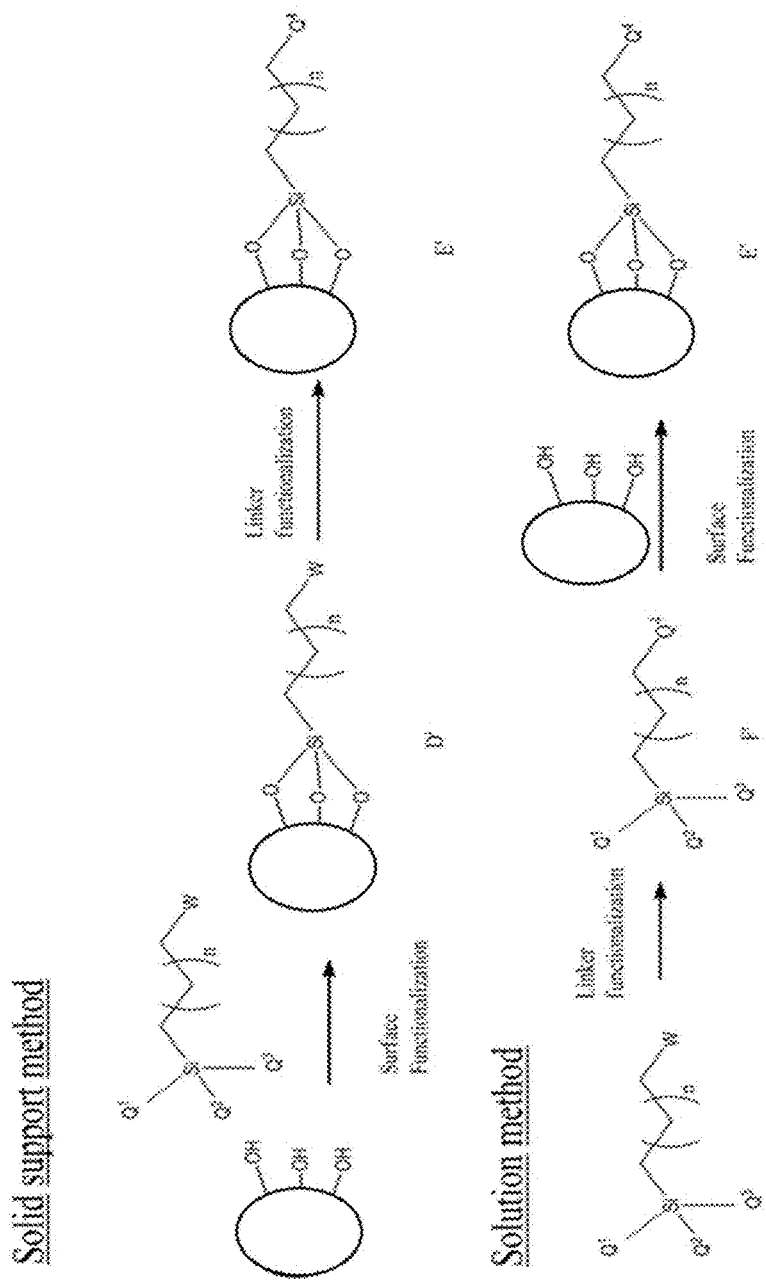
FIG. 6 depicts schemes of solid support and solution methods for the preparation of particles of this invention wherein the anti-microbial unit has one monomeric unit (a monomeric backbone, as presented in FIG. 1B). The circles represent an organic or inorganic core. $Q^1$, $Q^2$ and $Q^3$ are independently selected from the group consisting of ethoxy, methoxy, methyl, ethyl, hydrogen, sulfonate and halide, wherein at least one of $Q^1$, $Q^2$ and $Q^3$ is a leaving group selected from ethoxy, methoxy, sulfonate (e.g., mesyl, tosyl) and halide. For the sake of clarity the scheme presents a case where $Q^1$, $Q^2$ and $Q^3$ represent leaving groups; $Q^4$ represents an anti-microbial group; W is selected from the group consisting of $NH_2$, halide, sulfonate and hydroxyl; and n is an integer between 1 and 16.

Solid Support Method for the Preparation of Anti-Microbial Particles using Self-Polymerized Silane Linker Preparation of functionalized particles is conducted in two general steps. First, the linker molecule is allowed to condense onto particles surface (surface functionalization) via hydrolysis of leaving groups to give an intermediate of formula (FIG. 6, D'). Second, functional sites of the linker molecule undergo further functionalization (linker functionalization) as mentioned in any ones of (FIGS. 3-5) to give a functionalized particle of formula (E').

Solution Method for the Preparation of Anti-Microbial Particles using Self-Polymerized Silane Linker In the solution method for the preparation of anti-microbial particles comprising self-polymerized silane linker, the linker is first functionalized with anti-microbial active group to give an intermediate of formula (FIG. 6, F'). In the second step intermediate (F') is allowed to settle onto particle's solid surface (surface functionalization) to give a functionalized particle of formula (FIG. 6, E').

Figure 7:
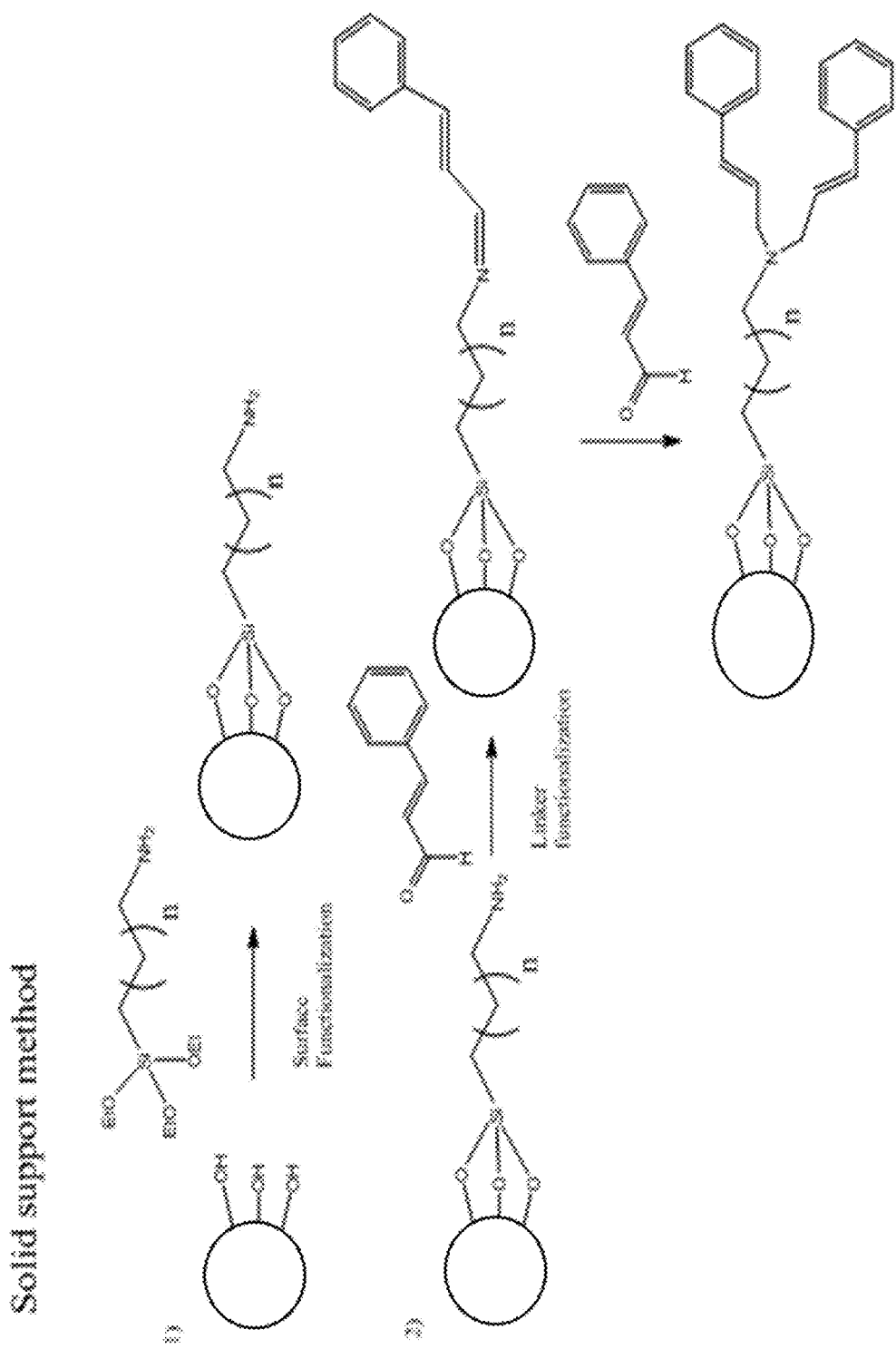
FIG. 7 depicts a representative scheme for the preparation of di-cinnamyl groups with core particle (represented as a circle) functionalized utilizing a 12-(triethoxysilyl)-dodecan-1-amine linker by both solid support method and solution method, wherein the anti-microbial part has one monomeric unit (a monomeric backbone, as presented in FIG. 1B). n is an integer of 1 to 16.

This process is exemplified in FIG. 7 for cinnamaldehyde, but is applicable to other aldehydes.

It is understood that that the group

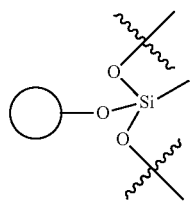

(FIGS. 6-7) represents a self-polymerized, solid supported trialkoxysilane linker molecule.

It is understood that that the group

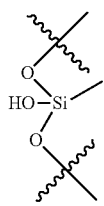

(FIGS. 6-7) represents a self-polymerized trialkoxysilane linker molecule, non-bound to the core.

ii) Solid Support Method for the Preparation of Anti-Microbial Particles using Non-Self-Polymerized Silane Linker In some embodiment, a solid support method comprises few stages. First, the linker molecule (dilute solutions of a few percent) is allowed to condense onto particles surface (surface functionalization) via (acid catalyzed) hydrolysis of leaving groups, resulting in the attachments of the linker to the core (FIG. 8, step 1). Second, the attached linker is elongated. In another embodiment, this stage is achieved synthetically via one step or more. In another embodiment, elongation is achieved by consecutive addition of difunctionalized alkane and diaminoalkane, wherein amines (of attached linker and diaminoalkane) attack electrophilic centers of the difunctionalized alkane (FIG. 8, steps 2 and 3). In another embodiment, such consecutive addition is optionally repeated for 1-10 times. Finally, the anti-microbial active group (usually attached to an alkylene chain) is grafted to resulting attached and elongated linker. In another embodiment, grafting is accomplished when amines on the attached and elongated linker attack acyl halide moiety of the molecule of the anti-microbial active group which is grafted (FIG. 8, step 4).

iii) Solution Method for the Preparation of Anti-Microbial Particles using Non-Self-Polymerized Silane Linker The solution method for the preparation anti-microbial particles using non-self-polymerized silane linker comprises few steps. The first step involves elongation of the linker molecule. In another embodiment, this step is achieved synthetically via one step or more. In another embodiment, elongation is achieved by consecutive addition of difunctionalized alkane and diaminoalkane wherein amines (of linker and diaminoalkane) attack electrophilic centers of the difunctionalized alkane (FIG. 9, steps 1 and 2). In another embodiment, such consecutive addition is optionally repeated for 1-10 times. In the second step, the anti-microbial active group (usually attached to an alkylene chain) is grafted to resulting elongated linker. In another embodiment, grafting is accomplished when amines on the elongated linker attack acyl halide moiety of the molecule of the anti-microbial active group which is grafted (FIG. 9, step 3). Finally, the elongated, anti-microbial active linker is attached to the core via functionalization thereof. In this stage, the linker molecule is allowed to condense onto particles surface (surface functionalization) via hydrolysis of leaving groups, resulting in the attachments of the linker to the core (FIG. 9, step 4).

Figure 10:
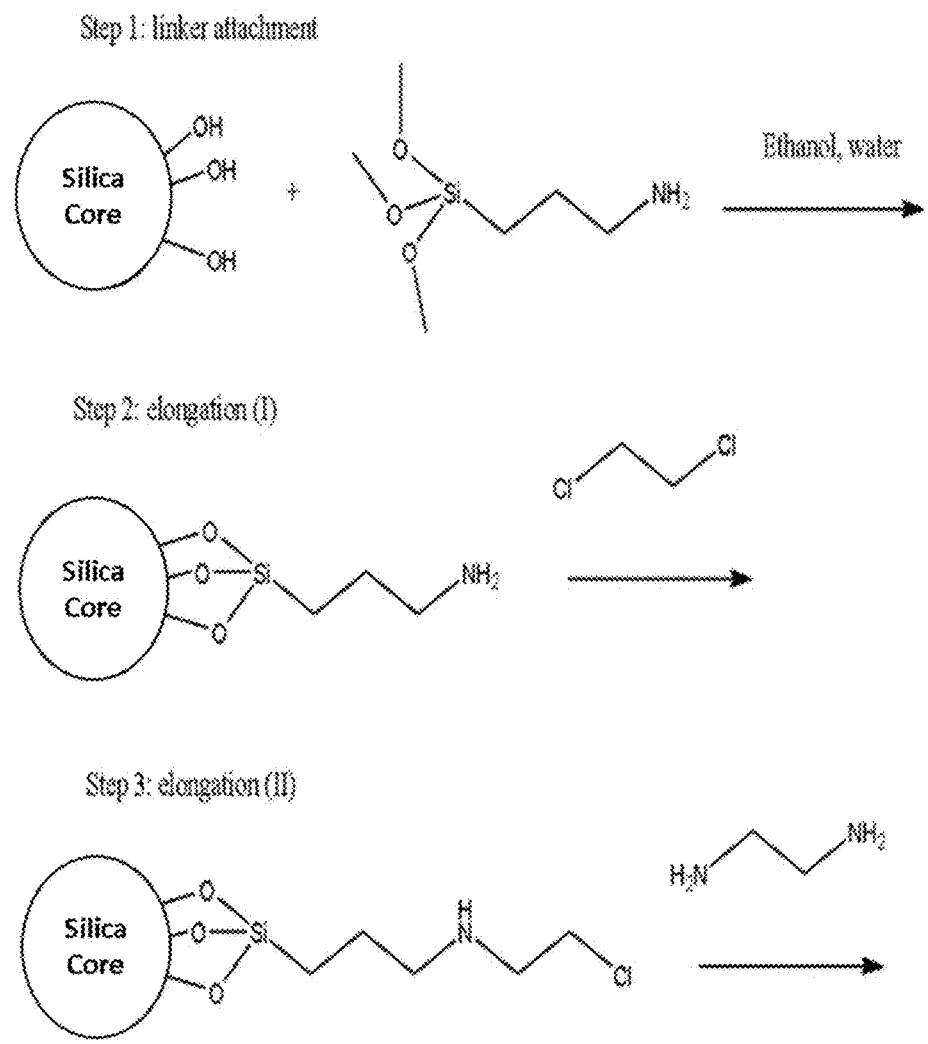
FIG. 10 depicts a scheme for the preparation of silica based anti-microbial particles according to this invention comprising dimethylethylammonium as the anti-microbial active group, in a solid support method, wherein the anti-microbial unit has more than one monomeric unit (i.e has an oligomeric or polymeric backbone).

The process for the preparation of anti-bacterial particles using non-self-polymerized silane is also exemplified in FIGS. 10-11 for silica functionalized with dimethylethylammonium, but is applicable to other hydroxyl-terminated cores, silanes and anti-microbial active groups.

Compositions

Particles Embedded in a Hosting Matrix or in Raw Materials

According to another aspect, this invention provides a composition having a liquid or solid matrix embedding a plurality of particles as described above, wherein the particles are embedded in the matrix through covalent or non-covalent interactions.

The matrix is preferably a polymeric matrix comprising a hydrogel and/or a thermoplastic polymer selected from the group consisting of polyvinylchloride (PVC), polyurethane, polyethylene, polypropylene, silicone, epoxy resin, composite materials and acrylic polymers such as poly methyl methacrylate or any combination thereof. In another embodiment, the hydrogel is poloxamer or alginate. In another embodiment, the commercial poloxamer is used or it is formed by a reaction between a polymer and other reagent. In another embodiment, the polymer is poly(ethylene glycol) (PEG) with reactive end groups (such as epoxides in PEG-diglycidyl ether) and the reagent has multiple reactive sites (e.g. diethylenetriamine)

Other types of substances that may serve as hosts are ceramics, composite materials of polymeric material and inorganic solids, plant powders and particles compressed into a solid article, and organic and inorganic glues. Other substances may be selected from metal coatings and other solid, semisolid or gel-like materials.

In another embodiment, the composition is in a form selected from the group consisting of a cream, an ointment, a paste, a dressing and a gel.

Another polymer matrix to be used in this invention is a resin used in dental, surgical, chirurgical or orthopedic composite materials. In such applications, antibacterial particles are first dispersed within the resin part or added simultaneously with filler or any other solid ingredients (if any). In other embodiments, the resins are acrylic or epoxy type monomers that undergo polymerization in-vivo.

In some embodiments, embedding functionalized particles into polymeric matrices may be achieved by a variety of methodologies. For example, embedding functionalized microparticles into a polypropylene host matrix was obtained by two methodologies: A) Extrusion technology: the particles are added into molten polymer, preferably into twin-coned extruder. B) Polypropylene is heated in xylene, toluene or their derivatives under reflux conditions to achieve the complete dissolution of the polymer. The antibacterial particles are then dispersed in the same solvent as used for the polymer and the mixture is added to the dissolved polymer using overhead stirrer or homogenizer. After complete dispersion of particles within the polymer, the solvent is evaporated using conventional distillation or evaporation method.

Thus, according to some embodiments, this invention provides a method for preparing a composition comprising embedding a plurality of particles in a matrix or in a raw material as described above, wherein the particles are embedded in the matrix or in the raw material, the method comprising step of adding the particles as described above, into a molten polymer matrix utilizing extrusion or to a polymer solution in solvent.

In some embodiment, the particles are added to raw material during the production for example of medical devices (e.g. stents and catheters). Thus, the medical device has anti-microbial activity.

The embedment of anti-bacterial particles is mainly due to mechanical forces. These particles are "locked" between the polymer chains in a three-dimensional matrix, preventing them from migrating out from the complex network. The strong hydrophobic nature of these particles also plays a role in preventing the particles from moving into the hydrophilic surrounds such as in the case of dental, orthopedic or other medical and dental applications.

In some embodiments, particles according to the invention are homogeneously distributed on the outer surface of the matrix in a surface concentration of between about 0.1 to about 100 particles per sq. micrometer. In another embodiment, particles according to the invention are homogeneously distributed on the outer surface of the matrix in a surface concentration of between about 1 to about 100 particles per sq. micrometer The term "homogeneous distribution" is used to denote a distribution, characterized in that the standard deviation of the number of particles per sq. um is no more than the average number of particles per sq. micrometer. A homogeneous distribution is preferred for reproducibility and product specifications. If the distribution is not even, the product may exhibit different properties at different areas. The distribution of the particles away from the outer surface, that is, their bulk concentration, may be similar to that on the outer surface. As a general rule, the total surface of the particles preferably occupies at most about 20% of the surface of the matrix, preferably between 1% to 15%, more preferably between 1% and 5% and most about between 1% and 3% of the surface of the matrix.

According to some embodiments, on the average, every sq. micrometer of the outer surface of matrix has at least one particle of this invention.

The polymeric particles may be physically entrapped within the matrix, chemically bound thereto, or both. In case the particles are to be chemically bound to the host, the particles have functional groups that are capable of reacting with the host matrix (e.g., host polymer, or with monomers thereof. Thus, in some embodiments, the particles of this invention have functional groups that are capable of reacting with a host polymer or matrix. Such functional groups are designed to allow the particles to be chemically bound to the hosting matrix.

Polymeric particles of this invention may also include tertiary amines, tertiary ammonium or quaternary ammonium groups that are not anti-microbial active.

However, the more anti-microbial active groups there are, the more preferred is the polymer, and a particle including an organic core according to the invention is characterized by having at least one anti-microbial active group per 10 sq. nm.

Composition-Uses Thereof

In one embodiment, the invention is directed to a packaging composition comprising a thermoplastic polymer and/or a hydrogel embedded with particles of this invention. In another embodiment, the thermoplastic polymer is embedded with a mixture of two or more different particles of this invention. In another embodiment, the packaging composition is used in the packaging of food, beverage, pharmaceutical ingredients, medical devices, surgical equipment before operation, pre operation equipment, cosmetics, and sterilized equipment/materials.

In one embodiment the packaging composition comprises a thermoplastic polymer and/or a hydrogel embedded with the particles of this invention. In another embodiment, the thermoplastic polymer is polyvinylchloride (PVC), polyethylene, polypropylene, silicone, epoxy resin or acrylic polymers. In another embodiment, the thermoplastic polymer is poly methylmethacrylate or polyurethane.

In another embodiment, the packaging composition further comprises binders, coatings, lubricants and disintegrants. In another embodiment, non-limiting examples of binders include saccharides, gelatin, polyvinylpyrolidone (PVP) and polyethylene glycol (PEG). In another embodiment, non-limiting examples of coatings include hydroxypropylmethylcellulose, polysaccharides and gelatin. In another embodiment, non-limiting examples of lubricants include talc, stearin, silica and magnesium stearate. In another embodiment, non-limiting examples of disintegrants include crosslinked polyvinylpyrolidone, crosslinked sodium carboxymethyl cellulose (croscarmellose sodium) and modified starch sodium starch glycolate.

In one embodiment, the packaging composition is used for packaging pharmaceutical ingredients. In another embodiment, non-limiting examples of pharmaceutical ingredients include analgesics, antibiotics, anticoagulants, antidepressants, anti-cancers, antiepileptics, antipsychotics, antivirals, Sedatives and antidiabetics. In another embodiment, non-limiting examples of analgesics include paracetamol, non-steroidal anti-inflammatory drugs (NSAIDs), morphine and oxycodone. In another embodiment, non-limiting examples of antibiotics include penicillin, cephalosporin, ciprofloxacin and erythromycin. In another embodiment, non-limiting examples of anticoagulants include warfarin, dabigatran, apixaban and rivaroxaban. In another embodiment, non-limiting examples of Antidepressants include sertraline, fluoxetine, citalopram and paroxetine. In another embodiment, non-limiting examples of anti-cancers include Capecitabine, Mitomycin, Etoposide and Pembrolizumab. In another embodiment, non-limiting examples of antiepileptics include Acetazolamide, Clobazam, Ethosuximide and lacosamide. In another embodiment, non-limiting examples of antipsychotics include Risperidone, Ziprasidone, Paliperidone and Lurasidone. In another embodiment, non-limiting examples of antivirals include amantadine, rimantadine, oseltamivir and zanamivir. In another embodiment, non-limiting examples of sedatives include Alprazolam, Clorazepate, Diazepam and Estazolam. In another embodiment, non-limiting examples of antidiabetics include glimepiride, gliclazide, glyburide and glipizide.

In one embodiment, the packaging composition is used in the packaging of food ingredients. In another embodiment, non-limiting examples of food ingredients packaged with the packaging material of the invention include fresh food, preservatives, sweeteners, color additives, flavors and spices, nutrients, emulsifiers, binders and thickeners. In another embodiment, non-limiting examples of fresh food include: meat, poultry, fish, dairy products, fruits and vegetables. In another embodiment, non-limiting examples of preservatives include Ascorbic acid, citric acid, sodium benzoate, calcium propionate, and sodium erythorbate and sodium nitrite. In another embodiment, non-limiting examples of sweeteners include Sucrose (sugar), glucose, fructose, sorbitol, mannitol and corn syrup. In another embodiment, non-limiting examples of color additives include Orange B, Citrus Red No. 2, annatto extract, beta-carotene, grape skin extract, cochineal extract or carmine and paprika oleoresin. In another embodiment, non-limiting examples of flavors and spices include monosodium glutamate, glycine slats, inosinic acid, isoamyl acetate, and limonene and allyl hexanoate. In another embodiment, non-limiting examples of nutrients include Thiamine hydrochloride, riboflavin (Vitamin $B_2$), niacin, niacinamide, folate or folic acid. In another embodiment, non-limiting examples of emulsifiers include Soy lecithin, mono- and diglycerides, egg yolks, polysorbates and sorbitan monostearate. In another embodiment, non-limiting examples of binders and thickeners include Gelatin, pectin, guar gum, carrageenan, xanthan gum and whey.

In one embodiment, this invention is directed to a pharmaceutical composition comprising anti-microbial particles of this invention and at least one of: a pharmaceutical ingredient, an excipient and a liquid or solid matrix embedding such anti-microbial particles. In another embodiment, the composition is in a form selected from the group consisting of a cream, an ointment, a paste, a dressing and a gel, more preferably, wherein the composition is formulated for topical application or administration.

In one embodiment, the composition of this invention comprising the anti-microbial particles is used for paints for ships, that prevent growth of biofilm or treats, breaks down and/or kills biofilm or bacteria within, paints for bathrooms, paint for hospitals and clean rooms; water filtration media and many others. Each possibility represents a separate embodiment of this invention.

Medical Devices

Accordingly, compositions according to the invention may find utility in a broad range of applications, where decontamination or growth prevention of bacteria is required. In some embodiments, this invention provides medical devices comprising the compositions or pharmaceutical compositions as described hereinabove, selected from the following non-limiting group: medicine artificial replacement of tissues such as bone, bone cements and joints (orthopedic), surgical mesh, breast implants, lenses (ophthalmology), blood vessels and stents, artificial heart valves (cardiology), artificial skin, implants (plastic surgery), intra uterine devices (gynecology), neurosurgical shunts, catheters, stents, urethral stents coating for subcutaneous implants: insulin pumps, contraceptives, pacemakers. tubing and cannula used for intra venous infusion, tubing and cannula used for dialysis, surgical drainage tubing, urinary catheters, endotracheal tubes, wound covering (dressing and adhesive bandage) and treatment (e.g. gels, ointments, pastes and creams for wound care which reduce biofilm and bacteria to aid wound healing) materials, sutures, catheters of all kinds that are inserted temporarily or permanently in blood vessels as well as the urinary system, shunt for use in brain applications, surgical gloves, tips for ear examination, statoscope ends and other elements used by the medical personnel; tooth pastes, tooth brushes, tooth pick, dental floss, and interdental and tongue brushes, lotions, hand-sanitizers, ointments and creams used for dermatology or in the cosmetic industry, plastic wear for medical and research laboratories.

In some embodiments, the particles or composition comprising thereof are used for dental and orthopedic resin based cements, sealers, composite materials, adhesives and cements; for dental and orthopedic metal implants and wires; for surgical sutures; for catheters, metal surgical tools, non-surgical medical devices. Each possibility represents a separate embodiment of this invention.

In one embodiment, this invention further provides a medical device comprising an endoscope (rigid and flexible), including, and not limited to a colonoscope, gastroscope, duodenoscope, bronchoscope, cystoscope, ENT scopes, laparoscope, laryngoscope and similar instruments for examination or treatment the inside of the patient's body, including any parts thereof, as well as accessories and other devices used in the procedure which either come in contact with body tissue or fluids; tubes, pumps, containers and connectors (used inside or outside the body) through which fluids, air or gas may be pumped into or suctioned out from the patient and could become contaminated by the patient or transfer contaminants from other patients; items such as brushes, trays, covers, tubes, connectors cabinets and bags used for reprocessing, cleaning, transporting and storing such equipment and can transmit or host biological contaminants.

Dental

One preferred use of the compositions of this invention is in dentistry: dental adhesives, dental restorative materials such as all types of composite based materials for filling tooth-decay cavities, endodontic filling materials (cements and fillers) for filling the root canal space in root canal treatment, materials used for provisional and final tooth restorations or tooth replacement, including but not restricted to inlays, onlays, crowns, partial dentures (fixed or removable) dental implants, and permanent and temporary cements used in dentistry for various known purposes, dental and orthopedic resin based cements, sealers, composite materials, adhesives and cements, dental restorative composites, bone cements, tooth pastes.

In one embodiment, this invention further provides a medical device comprising a dental appliance. In one embodiment, this invention further provides a medical device comprising an orthodontic appliance. The dental appliance and the orthodontal appliance comprise the particles and composite of this invention. In some embodiments, the orthodontal appliance include an aligner for accelerating the tooth aligning, a bracket, a dental attachment, a bracket auxiliary, a ligature tie, a pin, a bracket slot cap, a wire, a screw, a micro-staple, cements for bracket and attachments and other orthodontic appliances, a denture, a partial denture, a dental implant, a periodontal probe, a periodontal chip, a film, or a space between teeth. In some embodiments, the dental appliance includes a mouth guard, used to prevent tooth grinding (bruxer, Bruxism), night guard, an oral device used for treatment/prevention sleep apnea, teeth guard used in sport activities.

In one embodiment the composition of this invention is a varnish or glaze which is applied to the tooth surface, a restoration of tooth or a crown comprising the particles of this invention. In another embodiment the varnish or glaze provide a protective coating, lacquer; superficially polished appearance to the tooth surface, restoration or crown of the tooth. In another embodiment, the varnish is a fluoride varnish which is a highly concentrated form of fluoride which is applied to the tooth's surface, as a type of topical fluoride therapy. In another embodiment, the aim of glazing is to seal the open pores in the surface of a fired porcelain. Dental glazes are composed of colorless glass powder, applied to the fired crown surface, so as to produce a glossy surface. Unglazed or trimmed porcelain may also lead to inflammation of the soft tissues it contacts.

In one particular embodiment, the composition of this invention is intended for administration into an oral cavity. The composition may be formulated as a tooth paste, and/or may be applied to a surface or medical device selected from the group consisting of: a denture cleaner, post hygienic treatment dressing or gel, mucosal adhesive paste, a dental adhesive, a dental restorative composite based material for filling tooth, decay cavities, a dental restorative endodontic filling material for filling root canal space in root canal treatment, a dental restorative material used for provisional and final tooth restorations or tooth replacement, a dental inlay, a dental onlay, a crown, a partial denture, a complete denture, a dental implant and a dental implant abutment.

The anti-microbial property may protect the patient and the medical staff from cross contamination from patient to patient or from patient to the examiner Self-sterilizing packaging for medicines and items that enter the operation room are also beneficial. Applications out of the medical field may for example be in clothing (e.g. for sports or outdoor activity; to prevent bacteria-induced sweat odor), athlete shoes or the inner part of a shoe wherein bacteria tend to collect, tooth brushes and any brush that comes in contact with the human body, pet cages as well as other veterinary items, etc.

In one embodiment, this invention provides raw materials comprising the particles of this invention for the preparation of medical devices such as stents or catheters, specifically stents made of polymeric materials, wherein the particles are embedded in the raw material through covalent or non-covalent interactions.

Methods of Inhibition of Bacteria

According to another aspect of the invention there is provided a method for inhibition of bacteria, by contacting the bacteria with the particle of this invention, or a composition comprising the particle(s) of this invention. The term "inhibition" is used to denote destruction, i.e. annihilation, of at least 99% of the bacteria, preferably 99.9%, most preferably 99.99% of the bacteria; reduction in the growth rate of the bacteria; reduction in the size of the population of the bacteria; prevention of growth of the bacteria; causing irreparable damage to the bacteria; destruction of a biofilm of such bacteria; inducing damage, short term or long term, to a part or a whole existing biofilm; preventing formation of such biofilm; inducing biofilm management; or bringing about any other type of consequence which may affect such population or biofilm and impose thereto an immediate or long term damage (partial or complete).

The term "biofilm" refers to a population of biological species (bacteria) attached to a solid surface.

The terms "anti-microbial" and "anti-bacterial" are used herein interchangeably. The quaternary ammonium and the tertiary amine groups of this invention [—$^+$N($R_1$)($R_2$)($R_3$), —$^+$NH($R_1$)($R_2$), —N($R_1$)($R_2$) —$^+$N($R_1'$)($R_2'$)($R_3'$), —$^+$NH ($R_1'$)($R_2'$) or —N($R_1'$)($R_2'$) (defined in structures (1) to (3))] provide the anti-microbial activity. The quaternary ammonium's activity remains strong at any pH. Tertiary amines have high pKa values, therefore are active at almost all pH levels (up to 10, but not higher). The tertiary amine as well as the tertiary ammonium functional groups is less likely to cause undesirable side effects such as irritation of soft tissue, if used in contact with skin or mucosa or if used as a pharmaceutical composition.

In a preferred embodiment, the inhibition is achieved by contacting the bacteria with a matrix containing up to 5% w/w, more preferably up to 1% particles according to this invention, or compositions comprising them.

In one embodiment, this invention provides a method for inhibiting or preventing biofilm formation or growth, comprising applying onto a susceptible or infected surface or a medical device an anti-microbial particle, combination of particles or a composition comprising thereof.

In another embodiment, this invention provides a medical device of this invention for use in inhibiting or preventing biofilm formation or growth.

In one embodiment, this invention provides a method for inhibition of bacteria growth, the method comprising the step of contacting the bacteria with the anti-microbial particle or combination of particles of this invention, or a composition comprising such particle.

In one embodiment, this invention provides a method for treating, breaking down or killing biofilm or bacteria within, comprising applying onto a susceptible or infected surface or a medical device an anti-microbial particle or combination of particles of this invention, or a composition comprising such particle.

In some embodiments, the anti-bacterial compositions of this invention affect annihilation of at least about 99% of the contacted bacteria, preferably, at least about 99.99% of the contacted bacteria.

It was further surprisingly discovered that the particles of this invention maintain high anti-microbial properties over time without leaching out and with no alteration of the properties of the hosting matrix.

The particles of this invention demonstrate enhanced anti-bacterial activity originating from the presence of closely packed anti-bacterial groups on a given particle's surface.

The following non-limiting examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Preparation of Core Particles of Amorphous $SiO_2$ (Silica)

Silica dioxide core particles were prepared by hydrolysis of tetraalkoxy silicate under alkaline conditions. The reaction solution was prepared by mixing 9 parts by weight of ethanol, 0.4 parts of deionized water and 0.1 part of ammonia, keeping the pH within the range of 10-14. Controlling the particle size and the reaction rate is achieved by adjusting the concentration of water and ammonia in the reaction solution. 0.5 parts of tetraethyl orthosilicate (TEOS) was added to the solution in one portion with stirring at 1,000 RPM for 1 hour. The reaction mixture first turned opaque, followed by a white solid precipitation, indicating the reaction endpoint and agglomerates formation of primary particles. The particles were recovered by centrifugation filtration, rinsing with 20 parts of deionized water and drying using freeze drying or heating. Optionally, further surface activation may be performed by shortly rinsing particles in sulfuric acid/hydrogen peroxide solution commonly known as "piranha solution". This last step converts most of the particles' surface into hydroxyl form and promotes an efficient surface functionalization.

Example 2

Morphological Characterization of Silica Particles

Nitrogen adsorption method was used to determine the morphology of porous silica dioxide particles by utilizing Barrett-Joyner_Halenda (BJH) model. Non-functionalized mesoporous silica dioxide particles were rinsed in Milli-Q water, dried and then degassed. Pore size was obtained from the adsorption/desorption isotherm by applying BJH model. Average particle size measured using dynamic light scattering method. Therefore, said particles are of 186 nm in diameter and having pore size of 5.0 mm.

Example 3

Preparation of Magnetite Core Particles

Magnetite ($Fe_3O_4$) particles were prepared by co-precipitation of $Fe^{2+}$ and $Fe^{3+}$ ions, from $FeCl_2$ (1 mol eq) and $FeCl_3$ (0.5 mol eq) in aqueous solution in basic condition utilizing $NH_4OH$ (pH~12). After precipitation, the particles recovered under constant magnetic field. Prior to functionalization, particles were rinsed in Mili-Q water followed by vacuum drying. Surface activation of the obtained magnetite particles was performed by a short rinse of the particles in nitric acid or sulfuric acid and hydrogen peroxide solution. The last step converted most of particles' surface into hydroxyl form allowing further functionalization of the core.

Example 4

Surface Functionalization of Inorganic Core Particles

Solid Support Method
Within the solid support method, few steps were employed. First, the linker 3-aminopropyltrimethoxysilane was allowed to condense onto particles surface (surface functionalization) via hydrolysis of methoxy groups, resulting in the attachment of the linker to the silica core (FIG. 10, step 1). Second, the attached linker was elongated, by consecutive addition of 1,2-dichloroethane and 1,2-diaminoethane (FIG. 10, steps 2 and 3). In some cases such consecutive addition was repeated for a few times, depending on the desired number of antimicrobial groups. Finally, the anti-microbial active group, was grafted to resulting attached and elongated linker, via the acyl bromide moiety (FIG. 10, step 4).
Solution Method
Within the solution method, few steps were employed. In the first step the linker molecule was elongated by consecutive addition of 1,2-dichloroethane and 1,2-diaminoethane (FIG. 11, steps 1 and 2). In some cases such consecutive addition was repeated for a few times, depending on the desired number of antimicrobial groups. In the second step, the anti-microbial active group was grafted to resulting attached and elongated linker, via the acyl bromide moiety (FIG. 11, step 3). Finally, the elongated, anti-microbial active linker was attached to the silica core via functionalization thereof. In this step, the linker molecule was allowed to condense onto particles surface (surface functionalization) via hydrolysis of methoxy groups, resulting in the attachment of the linker to the core (FIG. 11, step 4).

Functionalization of silica particles was performed in two stages. Initially, primary amine-functionalized silica particles were prepared. The primary amine was the functionalized by reductive amination to yield a tertiary amine comprising terpenoid groups, or alternatively a quaternary ammonium group comprising one elongated alkyl chain of 8 carbons.

Figure 2C:
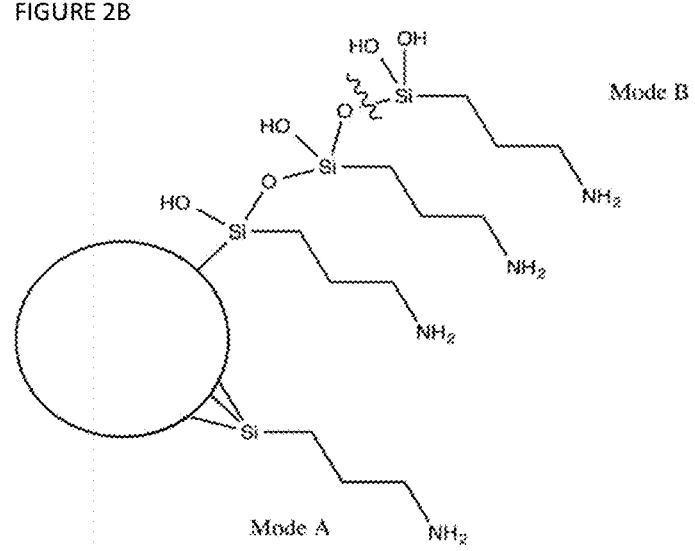

The silica particles were functionalized according to mode A or mode B as presented in FIG. 2C. Preferable surface densities of the functionalized silica particles are in the range of 2-100 active groups per 1 sq. nm in accordance with FIG. 2C (mode B).

A pretreatment of inorganic cores (for example $SiO_2$, $Fe_3O4$) was essential for removing any of residual organic material such as solvent or other ligands and converts the surface to active hydroxyl group that are ready to undergo functionalization (silanization). The pretreatment included rinsing the particle in 20 to 40% solution of hydrogen peroxide in sulfuric acid or alternatively in 20 to 40% of $NH_4$ solution in sulfuric acid for at least 5 minutes at ambient conditions or at elevated temperature, preferable at least for 30 minutes at 60° C.

Polymerization of the silane groups (FIG. 2C, Mode B) versus simple silanization (FIG. 2C, Mode A) was conducted by immersion of dry particles in dry toluene (1 to 10 g of particles; 50 ml toluene). Excess of silane coupling agent (for example APTES) was added at ratio of at least 10 mmol per 1 g of particles in the presence of catalytic acid (preferable acetic or hydrochloric acid). The coupling/polymerization was conducted at 60° C. for 1 h, then heated to 120° C. and stirred under reflux for at least 3 h. Concentrations of silane coupling agent, acid, temperature and time during the reaction determine the mode of functionalization (Mode A vs. Mode B) and the overall degree of surface density.

Example 5

Anti-Microbial Activity of Matrix Comprising Functionalized Silica Particles

Anti-Microbial Test Conditions—Direct Contact Test

Direct contact between bacteria and the tested materials was achieved by applying 10 μl of bacterial suspension on each tested material sample in a set of 8 wells. The plate was incubated at a vertical position for 1 h at 37° C. During this incubation period, the suspension's liquid evaporated and a thin layer of bacteria was obtained, ensuring direct contact between the bacteria and the tested material. The plate was then placed horizontally and 220 μl of brain-heart infusion broth were added to each well containing the material. All tests were done using *Stapilococcus aureus* (*S. aureus*) and *Enterococcus faecalis* (*E. faecalis*) as representative for Graham positive bacteria and *Pseudomonas aeruginosa* (*P. aeruginosa*) as representative for Graham negative bacteria.

The kinetic measurement of bacterial growth was done utilizing temperature controlled microplate spectrophotometer (VERS Amax, Molecular Devices Corporation, Menlo Oaks Corporate Centre, and Menlo Park, Calif., USA). The microtiter plate was placed in the spectrophotometer, at 37° C. with 5 sec vortex prior to every reading. Bacterial growth was estimated by the OD changes in each well at 650 nm every 20 minutes for 24 hours.

Sample Preparation

Preparing particles in polypropylene matrices was achieved by hot molding of polypropylene and the anti-microbial particles.

Preparing particles in polymethylmetacrylate matrices was achieved by embedding the particles in dental polymerizable methylmethacrylate (Unifast Trad, GC America inc) at concentration of few % wt/wt. Then the methylmethacrylate was mixed in a silicone crucible at a liquid/powder ratio of a few g/ml respectively, in accordance to manufacturer's instructions and then allowed to polymerize onto sidewalls of microtiter wells at 37° C. for 24 hours prior to the anti-microbial test.

Example 6

Figure 12:
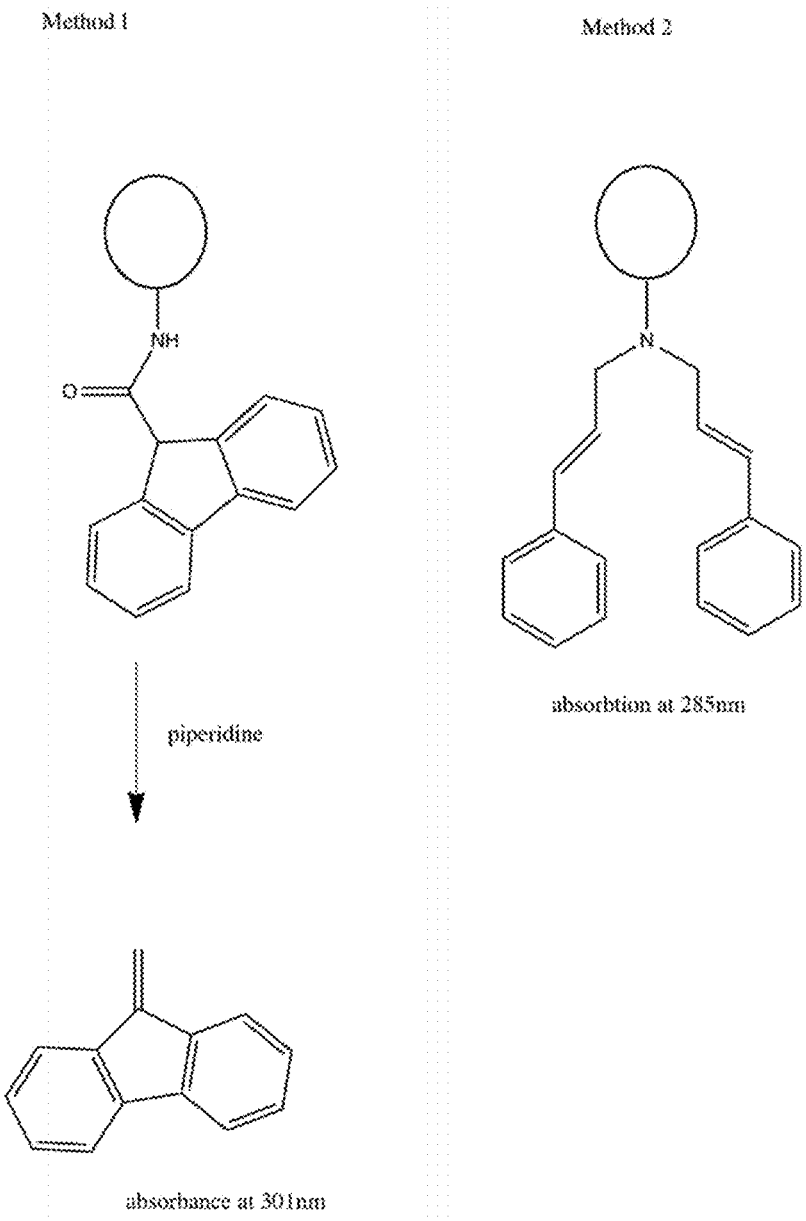
FIG. 12 depicts a scheme, showing methods to determine the load concentration of the anti-microbial group onto the core (represented by a circle).

Determination of the Loading Degree of Anti-Bacterial Active Groups onto the Core FIG. 12 presents a scheme of the different methods to determine the load concentration of the anti-microbial group onto the core.

Method 1—degree of amine loading onto particle's surface.

In one example, 1.0 g of powder of dry amine-functionalized silica particles comprising one anti-microbial active group per one oligomeric or polymeric anti-microbial active group having 180 nm diameter was immersed in 20 ml of dry toluene. Then 0.1 g (1.9 mmol) of Fluorenylmethyloxycarbonyl (Fmoc) chloride was added. The mixture was reacted at 60° C. under continuous stirring for 12 hours. Resulting particles were filtered and rinsed 3 times with 5 ml of N-Methyl-2-pyrrolidone (NMP), then 3 times with 5 ml of diethyl ether and then dried in-vacuum. Detachment of Fmoc was performed by immersing 0.01 g of Fmoc-labeled particles in 2 ml of 20% by volume solution of piperidine in NMP and shaked for 30 min followed by filtration of solvent. This procedure repeated once more and both solutions were combined (to a total of 4 ml solution). Concentration of Fmoc in solution was determined using light absorbance in spectrophotometer at 301 nm and calculated in accordance to Beer's law A=EbC, where A is absorbance, E is molar absorption constant (6300 cm$^{-1}$M$^{-1}$), b is pathway length (1 cm) and C is molar concentration. Prior to spectrometry readings, solution was diluted at 1:100 ratio in NMP.

Results: A=1.1, therefore C=100×(1.7×10$^{-4}$)M=0.017M. Therefore, N(moles)=0.017M×0.004L=6.98×10$^{-5}$ moles. Total loading is therefore 6.98×10$^{-5}$ mol/0.01 g=0.007 moles/gr. Assuming perfect sphere geometry of particles, the shell surface area of single particles is 102000 nm$^2$ and particle average volume is 3050000 nm$^3$. Particles density calculated using Archimedes method is 2.5 g/(1×10$^{21}$ nm$^3$), giving a single particle's mass of 7.6×10$^{-16}$ g. Therefore, the loading of functional groups is ((7.6×10$^{-16}$ g)×(0.007 moles/g))/102000 nm$^2$=5.2×10$^{-23}$ moles/nm$^2$, which is approximately 31 amine/ammonium per nm$^2$.

Method 2—degree of functional tertiary amines substituted with two cinnamyl groups. 0.001 g of 186 nm silica particles functionalized with di-cinnamyl amines were immersed in 100 ml of absolute ethanol. Spectrophotometric reading were taken at the wavelength of 327 nm. E(cinnamaldehyde)=25118 cm$^{-1}$M$^{-1}$. All calculations were performed as described in Method 1.

Results: A=1.5, therefore total tertiary amines count is 6.0×10$^{-6}$ moles, which is 3.0×10$^{-3}$ moles/g.

Therefore the functional groups loading is approximately 13 amine/ammonium per nm$^2$.

Similar calculations with the two methods were accomplished also for particles comprising more than one anti-microbial active group per one oligomeric or polymeric anti-microbial active group. Examples for resulting, calculated number of anti-microbial groups per sq nm, are presented in Table 1.

Both methods are applicable for all kinds of inorganic and organic core particles, whereas for organic particles (polymeric particles) the Fmoc functionalization is performed after the cross-linking step.

TABLE 1

Antibacterial activity dependency of polmethylmethacrylate modified particles of the invention as a function of functional groups density loaded onto particle surface.
All experiments were performed as in Examples 4 and 6.

| Particle | number of anti-microbial groups per sq nm (units/nm$^2$) | Inhibition of P. aerginosa (in Logs) | Inhibition of S. aureus (in Logs) |
|---|---|---|---|
| SiO$_2$ core | 13 | 4 | 5 |
| Quaternary ammonium (octyl dimethyl ammonium) func. | 31 | 6 | 6 |
| | 174 | 6 | 6 |
| SiO$_2$ core | 13 | 3 | 3 |
| di-cinnamylamine func. | 31 | 3 | 5 |
| | 174 | 5 | 6 |
| Fe$_3$O$_4$ core | 13 | 2 | 3 |
| Quaternary ammonium (octyl dimethyl ammonium) func. | 60 | 3 | 4 |
| | 130 | 5 | 5 |
| Fe$_3$O$_4$ core | 13 | 0 | 2 |
| di-cinnamylamine func. | 60 | 3 | 4 |
| | 130 | 4 | 5 |
| PEI core | 12 | 4 | 5 |
| Quaternary ammonium (octyl dimethyl ammonium) func. | 120 | 5 | 6 |
| | 230 | 5 | 6 |
| PEI core | 12 | 3 | 4 |
| di-cinnamylamine func. | 120 | 5 | 5 |
| | 230 | 5 | 6 |

As shown in the above table, the polmethylmethacrylate modified particles of the invention showed antibacterial activity for both inorganic and organic cores. The denser functional groups are packed onto particle surface, the stronger antibacterial activity against both tested organisms, for both organic and inorganic cores and for both quaternary ammonium salts and tertiary amines (terpenoids). Such denser packing is found as the number of anti-microbial active groups per one oligomeric or polymeric anti-microbial active group increases; for example, first (top) entry in each inorganic core has a ratio of only one anti-microbial active group per one oligomeric or polymeric anti-microbial active group, whereas other entries for the inorganic cores comprise higher ratio and those first entries have the lowest exhibited anti-bacterial activity.

Example 10

Activity of Silica Based Particles of this Invention

Four types of SiO$_2$ based particles were added to soft paraffin at concentration of 2% wt and dispersed until homogeneous paste was formed, while using ceramic pestle and crucible. Samples prepared according to example 4 and were marked as 2% Silicadioxide-di-cinnamylamine for particles having tertiary amine functional groups with two cinnamyl substituents, 2% Silicadioxide-quaternary ammonium for particles having one octyl and two methyls attached to quaternary nitrogen, 2% QPEI for quaternary ammonium polyethyleneimine, 2% Silicadioxide dimethylamino for samples having tertiary amine of two methylenes on the nitrogen and "E. faecalis" for control of paraffin-only group. Direct contact test (DCT) was performed for treated gauze pads with each one of paraffin samples. The results (FIG. 13) demonstrate strong inhibition of bacteria growth for all test samples excluding the dimethylamino variation. Specifically, the activity of terpenoids substituent onto tertiary amine functionality is surprising, due to their immobilization unlike known antimicrobial activity of free terpenoids.

Example 11

An Antibacterial Toothpaste Comprising Silica Based Particles of this

Composition of antibacterial toothpaste: glycerol, water, sorbitol, sodium lauryl sarcosine, hydrated silica, titanium dioxide and antibacterial particles. The antibacterial particles comprise $SiO_2$ particles which is commonly used in commercial toothpaste, where some of the particles are modified by covalently binding antibacterial groups. The antibacterial groups may be quaternary ammonium and tertiary amine having two cinnamyl groups or having tertiary amines with two citral groups. Below are shown results of a toothpaste formulation containing 5% wt of antibacterial $SiO_2$ particles having tertiary amine with two cinnamyl groups.

Surface retention experiment: Herein are presented results of particles retention onto glass surfaces examined by simulation of tooth brushing procedure during 1 minute with three compositions of toothpaste: A: commercially available toothpaste (control); B: the toothpaste composition as presented above, without antibacterial particles (control) and C: proposed toothpaste with antibacterial particles retention onto glass slides. After brushing, slides rinsed with same amount of water in same manner Retention examined visually (FIG. 14). The commercial toothpaste (Colgate® total) and the toothpaste formulation (with the composition as described above) with non-functionalized $SiO_2$ particles show no visible retention to glass surface. The toothpaste formulation with 5% wt of antibacterial particles ($SiO_2$ with tertiary amine having two cinnamyl groups) of this invention exhibits significant and visible retention to glass surface.

Figure 15:
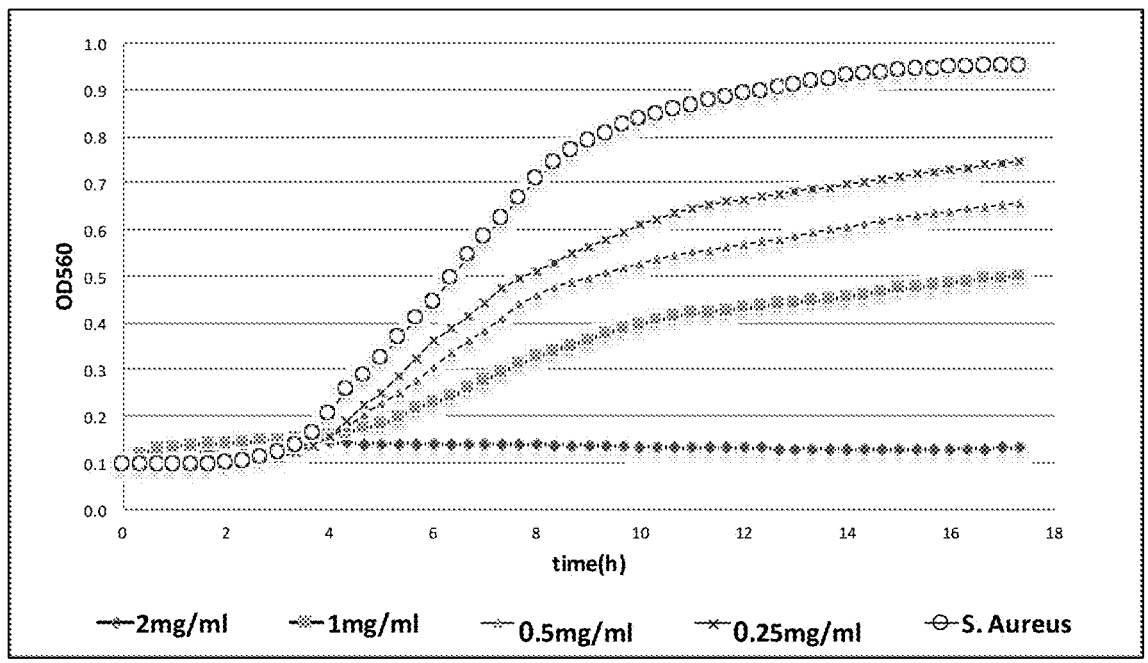
FIG. 15 depicts *S. Aureus* growth in the presence of toothpaste containing 0, 0.25, 0.5, 1, and 2% wt. $SiO_2$ particles having tertiary amine with two cinnamyl groups.

Antibacterial activity experiment: antibacterial activity of proposed toothpaste was examined by dispersing 10 µl of S.mutars (~$10^6$ viable cells) within total volume 220 µl of phosphate buffer saline (PBS) and proposed toothpaste. In this experiment, toothpaste formulation with antibacterial particles was tested, at the following final concentrations (% wt.): 0, 0.25, 0.5, 1 and 2. Each sample performed in 8 repetitions in 96 well plate. Bacteria growth monitored by reading optical density at 650 nm while incubating at 37° C. (FIG. 15). The antibacterial activity is proportional to particles concentration (dose-dependent effect). At concentration of 2% wt. there wasn't any single bacteria cell which survived out of the $10^6$ incubated viable bacteria cells.

Example 12

Contact Lenses Comprising Silica Based Particles of this Invention

A contact lenses composition comprising antibacterial $SiO_2$ particles with tertiary amine having two cinnamyl groups which are incorporated into polymethylmethacrylate at final concentration of 2% wt were prepared. The polymerization of the polymethylmethacrylate was done in the following method: 48 g of methyl methacrylate monomer were mixed with 1 g of benzoyl peroxide in glass beaker using overhead stirrer at 500 rpm. until complete dissolution of peroxide. In parallel, 50 g of methylmethacrylate were mixed with 1 g of dihydroxyethyl p-toluidine until complete dissolution. Into the methylmethacrylate/dihyhdroxyethyl and p-toluidine solution, 2 g of $SiO_2$ particles having tertiary amine with two cinnamyl groups were added and dispersed using high-shear homogenizer at 3000 rpm until homogeneous solution was obtained. Then both solutions were mixed and allowed to be polymerized onto sidewalls of 96 well plate.

Figure 16:
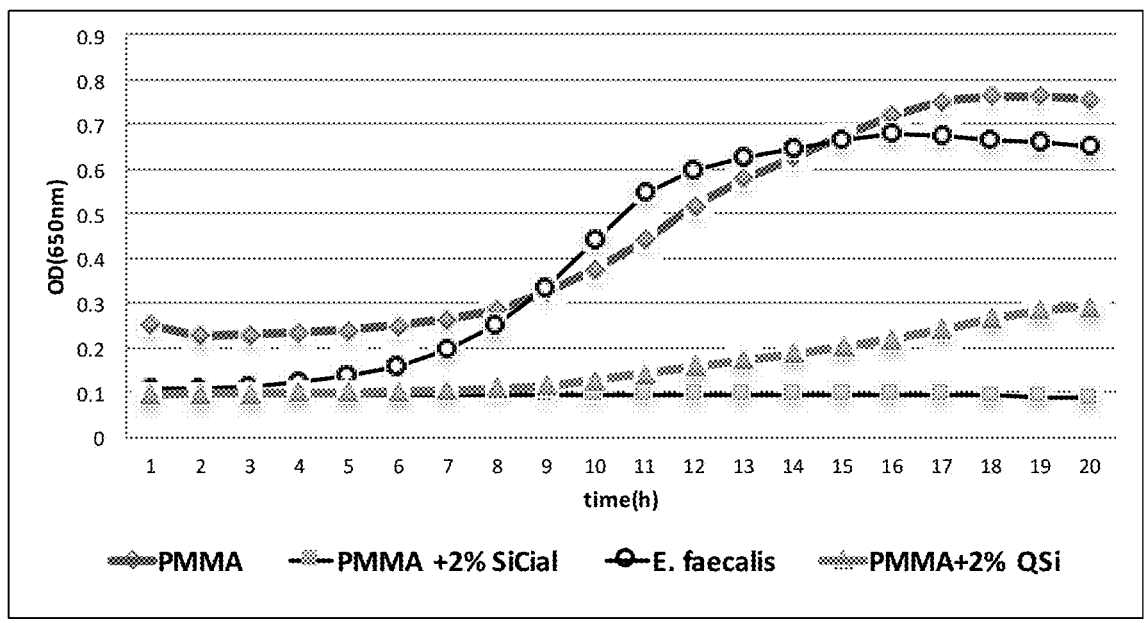
FIG. 16 depicts *E. faecalis* growth alone (control), on polymethylmethacrylate (PMMA, control), on polymethylmethacrylate incorporated with 2% $SiO_2$ particles having tertiary amine with two cinnamyl groups (Si-Cial) and on polymethylmethacrylate incorporated with 2% $SiO_2$ particles having quaternary ammonium (QSi). (QSi: silica particles functionalized with 170 dimethyl octyl ammonium groups per $nm^2$ (structure 1; $(m+n_1+n_2) \times m \times p=170$).

Antibacterial activity experiment: direct contact test (DCT) was performed using E. faecalis as test bacteria at 37° C. during 24 hours. FIG. 16 shows that in the present experiment the tertiary amine was more anti-bacterially active than quaternary ammonium when imbedded into polymethylmethacrylate in the same concentrations.

Example 13

Bone Cement Comprising Silica Based Particles of this Invention

Bone cement is used in orthopedics for fixation of implants during surgery operations. Bone cement composition: this cement composition is based on liquid monomer methylmethacrylate solution with initiators and solid prepolymerized polymethylmethacrylate with initiators as activators, as shown above for the contact lenses.

Figure 17:
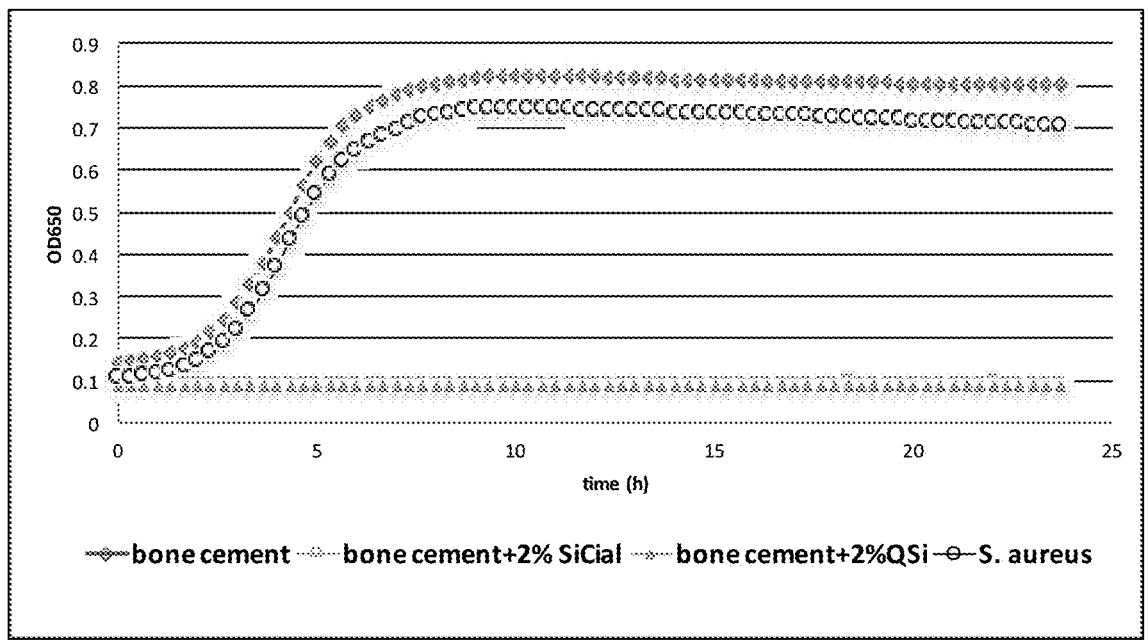
FIG. 17 depicts *S. aureus* growth alone (control), on bone cement (control), on bone cement incorporated with 2% $SiO_2$ particles having tertiary amine with two cinnamyl groups (Si-Cial) and on bone cement incorporated with 2% $SiO_2$ particles having quaternary ammonium (QSi: silica particles functionalized with 170 dimethyl octyl ammonium groups per $nm^2$ (structure 1; $(n_1+n_2) \times m \times p=170$).

Antibacterial activity experiment: the silica based antibacterial particles of this invention were added to a solid part of commercially available bone cement. Three samples have been tested for antibacterial activity: (I): $SiO_2$ particles having tertiary amine with two cinnamyl groups, (II): $SiO_2$ particles with quaternary ammonium, wherein the overall concentration of particles in each sample after mixing with liquid part of bone cement was 2% wt and (III) unmodified bone cement as control in this experiment. Samples of bond cement, unmodified and modified with antibacterial particles—were applied onto sidewalls of 96 wells plate and DCT protocol was performed with S. aureus as test bacteria. FIG. 17 shows that out of $10^6$ bacteria cells, there wasn't any single bacteria cell that grew on the surface of bone cement containing 2% wt. of silica based antibacterial particles of this invention.

Example 14

Antibacterial Activity of the Silica Based Antibacterial Particles of this Invention in a Water Filtration Media 1 g of chloromethyl-polystyrene beads (Merrifield resin) was dispersed within 50 ml of dichloromethane. 1 g of $SiO_2$ particles having tertiary amine with two citral groups was dispersed in 10 ml of dichloromethane using high shear homogenizer at 3000 rpm until homogeneous suspension was obtained. Both solutions were combined and stirred for 72 h at room temperature. Subsequently, modified beads with antibacterial particles were rinsed 5 times with 20 ml of DCM, then twice with 20 ml of diethyl ether and eventually were dried under vacuum overnight.

Figure 18:
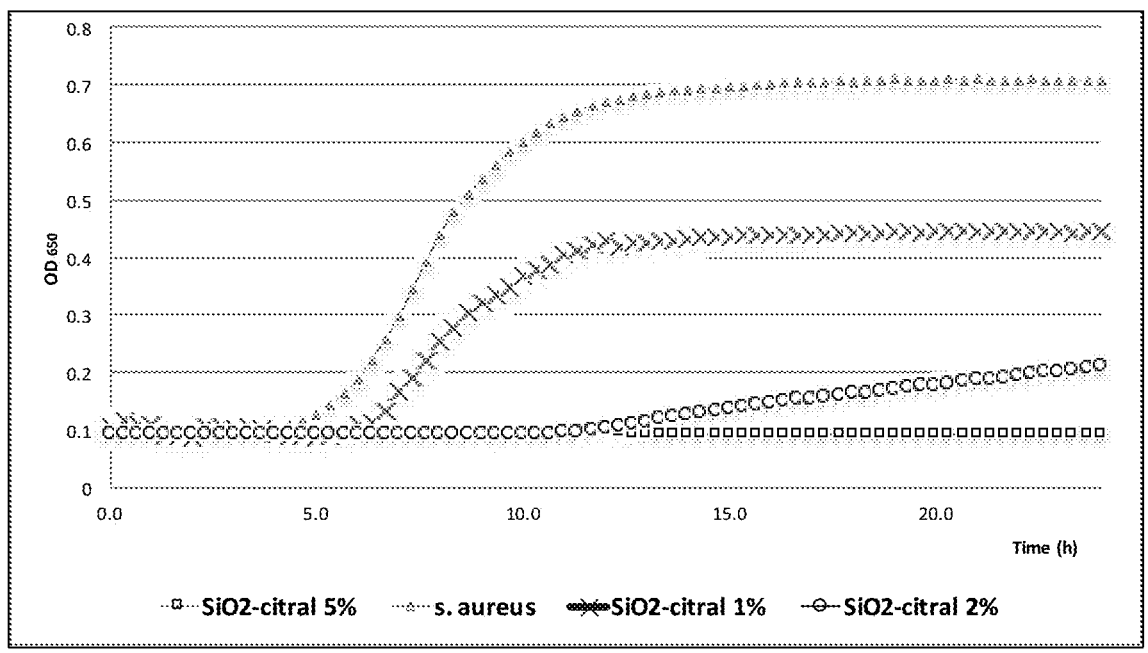
FIG. 18 depicts *S. aureus* growth alone (control) and on resin beads decorated with 1% $SiO_2$, 2% $SiO_2$ and 5% $SiO_2$ particles having tertiary amine with two citral groups ($SiO_2$-citral).

Antibacterial activity experiment: antibacterial test was performed in brain heart infusion (BHI) suspension of the modified beads to study the effect on *S. aureus* bacteria. 220 µl of BHI suspension with variable concentration of modified beads were poured into wells of 96 wells plate, with 8 wells for each concentration. Subsequently, 10ul of bacteria ($10^6$ viable cells) were added into each tested well and light absorbance was measured at 650 nm each 20 minutes for 24h. During the experiment, each plate with the sample was kept at 37° C. and shaked for 5 sec before each reading. As shown in FIG. 18, partial antibacterial activity is obtained for samples with 1% wt, followed by stronger effect for samples with 2% wt and complete bacteria inhibition at 5% wt.

Example 15

Antibacterial Activity of Silica Based Antibacterial Particles of this Invention with Tertiary Amine with 2 Cinnam 1 Groups or Quaternar Ammonium

TABLE 2 antibacterial activity of polymethylmethacrylate modified with $SiO_2$ particles having tertiary amine with two cinnamyl groups or with $SiO_2$ particles having quaternary ammonium groups.

| Entry | | Number of functional groups per square nanometer | *S. mutans* reduction in Direct Contact Test ($\log_{10}$) | *E. faecalis* reduction in Direct Contact Test ($\log_{10}$) |
|---|---|---|---|---|
| 1 | $SiO_2$ with quaternary ammonium | 0.1-0.4 | 3 | 4 |
| 2 | $SiO_2$ with quaternary ammonium | 6-10 | >6 | >6 |
| 3 | $SiO_2$ with tertiary amine with 2 cinnamyl groups | 0.1-0.4 | 2 | 4 |
| 4 | $SiO_2$ with tertiary amine with 2 cinnamyl groups | 6-10 | >4 | >6 |

Table 2 demonstrates the relation between the number of functional groups onto silica particle and the antibacterial activity against two selected bacteria. Entries 1 and 3 have a ratio of only one anti-microbial active group per one oligomeric or polymeric anti-microbial active group, whereas other comprise higher ratios. In addition, shown the differences between quaternary ammonium functionality and tertiary amines with two cinnamyl groups. It is concluded that (i) the number of functional groups is proportional to the ability of the particles to inhibit bacteria growth and (ii) quaternary ammonium functionality demonstrate strongest potency to inhibit bacteria growth than tertiary amines with 2 cinnamyl groups.

Example 18

Antibacterial Activity of Particles with Different Number of Monomeric Units

Figure 19:
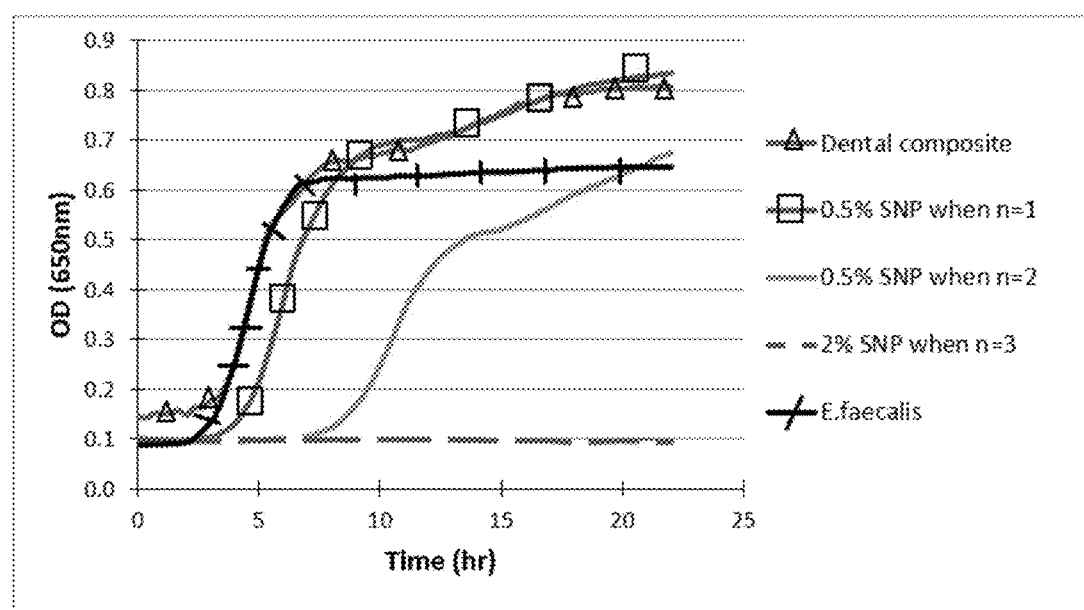
FIG. 19 presents the effect of chain length of active groups on antibacterial activity of quaternary ammonium functionalized particles. "SNP" refers silica based core functionalized with a dimethyl octyl ammonium quaternary ammonium groups, wherein the number of monomeric units per anti-microbial active unit is between 1 to 3 (referred in the Figure as n=1 to 3) and the number of anti-microbial active groups is 174 (structure 1; $(n_1+n_2) \times m \times p=174$) per one sq. nm ($nm^2$) of the core surface.

Silica core based nanoparticles (SNP) functionalized as seen in FIG. 19, with n=1-3, were embedded in commercially available dental polymerizable methylmethacrylate (Unifast Trad, GC America inc) at concentration of 0-2% wt/wt. The methylmethacrylate was mixed in a silicone crucible at a liquid/powder ratio of 2 g/ml respectively, in accordance to manufacturer's instructions and then allowed to polymerize onto sidewalls of microtiter wells at 37° C. for 24 hours prior to the anti-microbial test. The anti-bacterial test (direct contact test, see example 5) results (FIG. 19) demonstrated that increasing "n" leads to increased antibacterial activity (reduced OD of *E. faecalis*) and the most potent antibacterial effect was achieved when n=3.

Example 19

Poloxamer Hydrogel Compositions Comprising Silica Based Nanoparticles of this Invention The hydrogel was prepared by reacting poly(ethylene glycol) diglycidyl ether with diethylenetriamine Immediately after mixing of both reactants, 2QSi particles (FIG. 19, n=2) were introduced and mixed until uniform suspension obtained. This blend was poured onto flat mold and left to dry at 37° C. for 48 hours to complete polymerization. Subsequently, the thin film of the polymer was dipped in deionized water allowing it to absorb moisture.

The DCT protocol (Example 5) was used to evaluate the antibacterial activity of modified hydrogel with 2QSi, as presented in table 3.

TABLE 3 anti-bacterial activity of poloxamer hydrogel composites comprising 2QSi particles against *E. faecalis*

| Composition | Bacteria inhibition (Logs) |
|---|---|
| Poloxamer-based hydrogel + 1.5% 2QSi | >7 |
| Poloxamer-based hydrogel + 1.0% 2QSi | 3 |
| Poloxamer-based hydrogel + 0.5% 2QSi | 0.5 |
| Poloxamer-based hydrogel (control) | 0 |

As shown in the table, anti-bacterial activity (against *E. faecalis*) increased as the 2QSi particles concentration within the poloxamer composite was increased.

Example 20

Alginate Hydrogel Compositions Comprising Silica Nanoparticles of this Invention 2QSi particles (FIG. 19, n=2) were incorporated into alginate hydrogel by premixing dry alginate powder with 2QSi particles. Subsequently, sufficient amount of water was added and the compound was mixed until homogeneous paste was formed.

The hydrogel was allowed to dry onto sidewalls of DCT plates and antibacterial activity was evaluated in accordance to the DCT protocol (example 5), as presented in table 4.

TABLE 4 anti-bacterial activity of alginate hydrogel composites comprising 2QSi particles against *E. faecalis*

| Composition | Bacteria inhibition (Logs) |
|---|---|
| Alginate-based hydrogel + 2.0% 2QSi | >7 |
| Alginate-based hydrogel + 1.0% 2QSi | 5 |
| Alginate-based hydrogel (control) | 0 |

As shown in the table, anti-bacterial activity (against *E. faecalis*) increased as the 2QSi particles concentration within the alginate composite was increased.

Example 21

Activity in Sub-Cutaneous Implants In-Vivo

Design: The antibacterial activity of 2QSi-POSS particles [=POSS core functionalized with a methyl octyl ammonium quaternary ammonium groups, wherein the number of monomeric units per anti-microbial active unit is 2 [m=2; Structure 1)] incorporated in silicone implants at 2% w/w, implanted subcutaneous was tested. POSS particles having quaternary ammonium functionality with n=2 were incorporated into silicone rods that were implanted in the back of mice on one (right) side of the spine, and identical rods without particles were implanted on the opposite (left) side of the spine as controls. The implants were inoculated with 10 µl of $10^8$/ml *E faecalis* either one ex-vivo (before implantation) (Group A, n=10) or 8 times in 2-day intervals in-situ (starting 1 week after implantation, to allow for recovery, Group B, n=4). After explanation, the implants were vortexed and rinsed to remove free (planktonic) bacteria and then rolled on Agar plate to assess biofilm presence on the implant by CFU count (stamp test). \

Results: In group A (inoculated ex-vivo), among 9/10 animals available for explantation and analysis, none of the particle-containing implants had biofilm on the stamp test (zero CFU), compared to 6 control (no-particles) implants who had significant growth, 2 with minor growth and 1 with no growth. Similarly, no loosely bound bacteria were detected in the vortexed suspension from the test implants, vs. $1.5 \times 10^3$ recovered from the control implants. In group B (inoculated in-situ), stamp test showed no biofilm in 2 animals on both test and control implants, while in the 2 other animals there was extensive growth on the control implants vs. no growth on the test implant. Results are summarized in Table 5 below.

These results indicate that the antibacterial particles can prevent biofilm growth and significantly reduce overall number of bacteria on silicone subcutaneous implants.

The foregoing examples of specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The scope and concept of the invention will be more readily understood by references to the claims, which follow.

The invention claimed is:

1. A particle represented by the following structure (1):

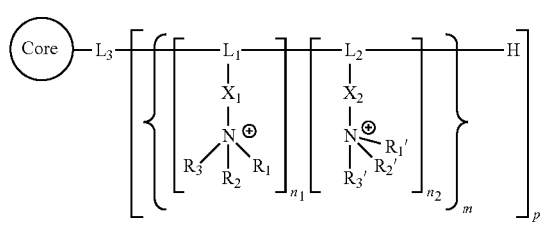

wherein
the core is an inorganic material;
$L_1$ is a first linker;
$L_2$ is a second linker;
$L_3$ is a bond or a third linker;
$R_1$ and $R_1'$ are each independently alkyl, terpenoid, cycloalkyl, aryl, heterocycle, alkenyl, alkynyl or any combination thereof;
$R_2$ and $R_2'$ are each independently alkyl, terpenoid, cycloalkyl, aryl, heterocycle, alkenyl, alkynyl or any combination thereof;
$R_3$ and $R_3'$ are each independently not present, hydrogen, alkyl, terpenoid moiety, cycloalkyl, aryl, heterocycle, alkenyl or alkynyl; wherein if $R_3$ or $R_3'$ is not present, then the nitrogen is not charged;
$X_1$ and $X_2$ is each independently a bond, alkylene, alkenylene, or alkynylene;
p defines the surface density of anti-microbial active units per square nanometer ($nm^2$) of the core surface, wherein said surface density is between 1-100 anti-microbial active groups per one square nanometer ($nm^2$) of the core surface of the particle;
$n_1$ is each independently an integer between 0 to 200;
$n_2$ is each independently an integer between 0 to 200;
wherein $n_1+n_2 \geq 2$;
m is an integer between 1 to 200 and the repeating unit is the same or different; and wherein the number of the anti-microbial active groups per each anti-microbial active unit is between 2-200.

2. The particle of claim 1, wherein said particle is represented by the following structure (2):

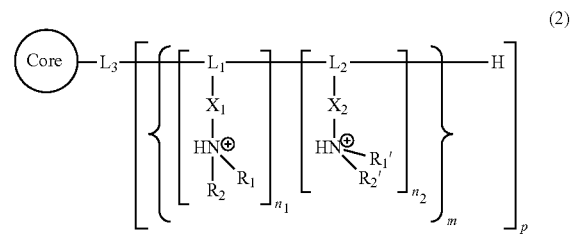

3. The particle of claim 1, wherein said particle is represented by the following structure (3):

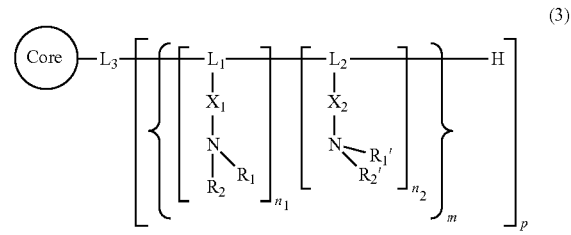

4. The particle of claim 1, wherein $R_1$ and $R_1'$ are terpenoids or $C_4$-$C_8$ alkyl.

5. The particle of claim 4, wherein $R_2$ and $R_2'$ are $C_1$-$C_4$ alkyl.

6. The particle of claim 5, wherein $R_3$ and $R_3'$ are not present.

7. The particle of claim 4, wherein $R_3$ and $R_3'$ are independently selected from alkyls, terpenoid moieties, cycloalkyls, aryl, heterocycle, alkenyl or alkynyl.

8. The particle of claim 1 wherein the inorganic core is selected from silica, glasses or ceramics of silicate, surface activated metal, metal, zeolite and metal oxide.

9. The particle of claim 8, wherein said inorganic core comprises:
(a) silica in a form selected from the group consisting of amorphous silica, dense silica, aerogel silica, porous silica, mesoporous silica and fumed silica;
(b) glasses or ceramics of silicate selected from the group consisting of aluminosilicate, borosilicate, barium silicate, barium borosilicate and strontium borosilicate;
(c) surface activated metals selected from the group consisting of silver, gold, platinum, palladium, copper, zinc and iron;
(d) metal oxides selected from the group consisting of zirconium dioxide, titanium dioxide, vanadium dioxide, zinc oxide, copper oxide and magnetite; or
(e) artificial or natural zeolite.

10. A composition comprising a liquid or solid matrix embedding a plurality of particles according to claim 1, wherein the particles are embedded in the matrix through covalent or non-covalent interactions.

11. The composition of claim 10, wherein the matrix is a polymeric matrix comprising a hydrogel, a thermoplastic polymer or a combination thereof.

12. A packaging composition comprising the composition of claim 10 wherein the packaging composition is for packaging a material selected from the group consisting of food, beverage, pharmaceutical ingredients, laboratory devices, medical devices, surgical equipment before operation, pre operation equipment, cosmetics, and sterilized equipment/materials used in industry and medicine.

13. The composition of claim 11, wherein the thermoplastic polymer is selected from the group consisting of polyvinylchloride (PVC), polyurethane, polyethylene, polypropylene, silicone, epoxy resin, composite materials and acrylic polymers.

14. The composition of claim 11, wherein said hydrogel comprises alginate or poloxamer.

15. The composition of claim 11, wherein the particles are homogeneously distributed on the outer surface of the matrix at a surface concentration of between about 0.1 to about 100 particles per sq. μm.

16. The composition of claim 10, wherein the composition is a cream, an ointment, a paste, a dressing or a gel.

17. The particle of claim 1, wherein the anti-microbial active groups have a surface density of 1-20 anti-microbial groups per 1 sq. nm of the core surface.

18. The particle of claim 1, wherein the anti-microbial active groups have a surface density of 50-100 anti-microbial groups per 1 sq. nm of the core surface.

19. The particle of claim 1, wherein the anti-microbial particles are represented by the following structure:

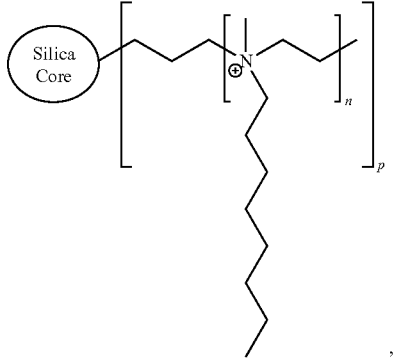

wherein n=2-200.

20. A medical device comprising the composition according to claim 10, wherein the medical device is selected from the group consisting of: an artificial heart valve, an intra uterine device, a catheter, a stent, an insulin pump, a pacemaker statoscope ends an endoscope, a colonoscope, a gastroscope, a duodenoscope, a bronchoscope, a cystoscope, an ENT (ear, nose and throat) scope, a laparoscope, a laryngoscope, parts and accessories of an endoscope, a pump, pumps a dental appliance, an orthodontic appliance, a tooth aligner, a bracket, a dental attachment, a bracket auxiliary, a ligature tie, a pin, a bracket slot cap, a denture, a partial denture, a periodontal probe, a periodontal chip, a film or a spacer between teeth, a mouth guard, a night guard, an oral device used for treatment or prevention of sleep apnea; and a teeth guard used in sport activities.

21. The composition of claim 10, wherein the composition is a varnish or glaze which is intended to be applied to a tooth surface, a restoration of a tooth, or a crown.

22. The composition of claim 21, wherein the varnish is a fluoride varnish.

23. The composition of claim 16, wherein the cream, ointment, paste, or gel is for wound care and treatment.

24. The composition of claim 10, wherein the composition is formulated as a dental adhesive, a dental restorative composite based material for filling tooth decay cavities, a dental restorative endodontic filling material for filling root canal space in root canal treatment, a dental restorative material used for provisional and final tooth restorations or tooth replacement, a dental inlay, a dental onlay, a crown, a partial denture, a complete denture, a dental implant, a dental implant abutment or a cement used to permanently cement crowns bridges, onlays, partial dentures or orthodontic appliances onto tooth enamel and dentin.

25. A product comprising the composition according to claim 10, wherein the product is selected from the group consisting of: tooth picks, tooth paste, dental floss, medicinal artificial replacement of tissues, surgical mesh, breast implants, lenses, stents, artificial skin, implants, neurosurgical shunts, urethral stents, coating for subcutaneous implants, contraceptives, tubing and cannula used for intra venous infusion, tubing and cannula used for dialysis, surgical drainage tubing, endotracheal tubes, wound coverings, sutures, shunts for use in brain applications, surgical gloves, tips for ear examination, interdental and tongue brushes, plastic wear for medical and research laboratories, tubes, containers and connectors, brushes, trays, covers, tubes, connectors, paint, cabinets, bags that can transmit or host biological contaminants, wires, screws, micro-staples, and cements for bracket attachments.

26. A method for inhibiting or preventing biofilm formation, comprising applying onto a susceptible or infected surface or a medical device a composition according to claim 10.

27. The method of claim 26, wherein the method is for inhibiting or preventing biofilm formation in a mouth and the composition is formulated as a tooth paste, mouthwash, tooth pick, dental floss, post hygienic treatment dressing or gel, mucosal adhesive paste toothbrush, and applied to oral hard and soft tissues and artificial surfaces.

28. The method of claim 26 wherein the method is for inhibiting or preventing biofilm formation in an oral cavity and the composition is formulated as a dental adhesive, a dental restorative composite based material for filling tooth decay cavities, a dental restorative endodontic filling material for filling root canal space in root canal treatment, a dental restorative material used for provisional and final tooth restorations or tooth replacement, a dental inlay, a dental onlay, a crown, a partial denture, a complete denture, a dental implant a dental implant abutment and a cement used to permanently cement crowns bridges, onlays, partial dentures and orthodontic appliances onto tooth enamel and dentin.

29. A method for treating, breaking down or killing biofilm or bacteria, comprising applying the composition of claim 10 onto an infected surface.

* * * * *